United States Patent
Moriya et al.

(10) Patent No.: US 7,541,477 B2
(45) Date of Patent: Jun. 2, 2009

(54) ANTAGONISTS TO MELANIN-CONCENTRATING HORMONE RECEPTOR COMPRISING BENZIMIDAZOLE DERIVATIVE AS ACTIVE INGREDIENT

(75) Inventors: Minoru Moriya, Tsukuba (JP); Akio Kanatani, Tsukuba (JP); Hisashi Iwaasa, Tsukuba (JP); Akane Ishihara, Tsukuba (JP); Takehiro Fukami, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 593 days.

(21) Appl. No.: 10/522,718

(22) PCT Filed: Jul. 29, 2003

(86) PCT No.: PCT/JP03/09610

§ 371 (c)(1),
(2), (4) Date: Jan. 28, 2005

(87) PCT Pub. No.: WO2004/011440

PCT Pub. Date: May 2, 2004

(65) Prior Publication Data

US 2005/0222161 A1    Oct. 6, 2005

(30) Foreign Application Priority Data

Jul. 30, 2002    (JP) ............... 2002-220905

(51) Int. Cl.
A61K 31/4184    (2006.01)
C07D 235/30    (2006.01)

(52) U.S. Cl. .................. 548/307.4; 514/388

(58) Field of Classification Search ............... 548/307.4
See application file for complete search history.

(56) References Cited

U.S. PATENT DOCUMENTS

| 2002/0107195 | A1 | 8/2002 | Gupta |
| 2003/0078252 | A1 | 4/2003 | Sanner et al. |
| 2004/0077628 | A1 | 4/2004 | Ishihara et al. |

FOREIGN PATENT DOCUMENTS

| EP | 0 419 210 | 3/1991 |
| EP | 1256578 | 11/2002 |
| JP | 03-109378 | 5/1991 |
| JP | 2001-139574 | 5/2001 |
| JP | 2003-64056 | 3/2003 |
| WO | 93/03714 | 3/1993 |
| WO | 95/32967 | 12/1995 |
| WO | 01/21577 | 3/2001 |
| WO | 01/82925 | 11/2001 |
| WO | 02/02744 | 1/2002 |
| WO | 02/28835 | 4/2002 |
| WO | 02/60374 | 8/2002 |
| WO | 03/15769 | 2/2003 |
| WO | 03/45313 | 6/2003 |

OTHER PUBLICATIONS

Keenan et al., CA 121:205342, 1994.*
Shigeyuki Chaki et al., "Recent advances in feeding suppressing agents: potential therapeutic strategy for the treatment of obesity", Expert Opinion on Therapeutic Patents, vol. 11, No. 11, pp. 1677-1692, XP002438303, ISSN: 1354-3776, 2001.

* cited by examiner

*Primary Examiner*—Laura L. Stockton
(74) *Attorney, Agent, or Firm*—Wenderoth, Lind & Ponack, L.L.P.

(57) ABSTRACT

This invention relates to a benzimidazole derivative of the general formula [I]

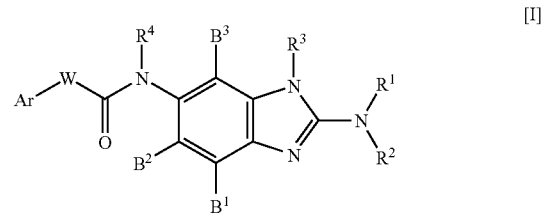

[wherein $B^1$, $B^2$, and $B^3$ represent hydrogen atom or lower alkyl; $R^1$ and $R^2$ are same or different and represent lower alkyl, etc.; $R^3$ and $R^4$ represent hydrogen atom, etc.; W represents a 3 to 8-membered aromatic or alphatic heterocycle, etc.; and Ar represents a substituted or unsubstituted aromatic heterocycle, etc.] This compound functions as an antagonist to melanin-concentrating hormone receptor and is useful as a drug for central diseases, circulatory diseases and metabolic diseases.

22 Claims, 1 Drawing Sheet

ANTAGONISTS TO MELANIN-CONCENTRATING HORMONE RECEPTOR COMPRISING BENZIMIDAZOLE DERIVATIVE AS ACTIVE INGREDIENT

TECHNICAL FIELD

This invention relates to benzimidazole derivatives which are useful in the filed of drugs. Said compounds act as antagonists to melanin concentrating hormone receptor, and are useful as preventing or treating agents of various diseases of cardiovascular system, nervous system, metabolic systems, reproductive system, respiratory system, digestive system and the like.

BACKGROUND ART

Melanin concentrating hormone (hereafter abbreviated as "MCH") is a cyclic peptide hormone/neuro-peptide, which was for the first time isolated by Kawauchi, et al. in 1983 from sermon hypophysis [Nature, Vol. 305, 321(1983)]. The hormone is known to functionally antagonize to melanin cell stimulating hormone in fishes, to cause concentration of melanin granules in melanophore and participate in body color change [International Review of Cytology, Vol. 126, 1(1991); Trends in Endocrinology and Metabolism, Vol. 5, 120 (1994)]. Also in mammals, MCH-containing neuron nerve cells are localized in the hypothalamus lateral field and uncertain zone, but their nerve fibers are projecting over a very wide scope in the brain [The Journal of Comparative Neurology, Vol. 319, 218(1992)], and MCH is considered to preside over various central functions in living bodies.

Hypothalamus lateral field is known of old as feeding center, and furthermore, recently molecular biological and pharmacological knowledges suggesting participation of MCH in controlling energetic homeostasis are being accumulated. That is, it has been reported that expression of mRNA, which is a MCH precursor, was accelerated in brains of ob/ob mouse, db/db mouse, $A^y$/a mouse, Zucker fatty rat or the like which are model animals of hereditary obesity, or in brains of fasted mice [Nature, Vol. 380, 243(1996); Diabetes, Vol. 47, 294 (1998); Biochemical and Biophysical Research Communications, Vol. 268, 88(2000); Molecular Brain Research, Vol. 92, 43(2000)].

Acute ventricular administration of MCH to rats was observed to induce accelerated feeding activity [Nature, Vol. 380, 243(1996)] and chronic administration invites obesity accompanied by polyphagy [Proceedings of the National Academy of Science of the United States of America, Vol. 99, 3240, (2002)]. Moreover, MCH precursor gene-deficient mouse shows reduced food ingestion or rise in oxygen consumption per body weight compared to wild type mice. Its low body weight due to decrease in body fat was observed [Nature, Vol. 396, 670(1998)].

On the contrary, transgenic mouse which expresses excessive MCH precursor develops obesity accompanied by polyphagy and insulin resistance [The Journal of Clinical Investigation, Vol. 107, 379 (2001)]. Consequently, it is suggested that MCH is an important factor for developing obesity and participates in diseases induced by metabolic disorder or respiratory diseases of which one of risk factors is obesity. Besides, MCH is known to participate also in anxiety-causing action, epilepsy, memory, learning, diuretic action, excretory action of sodium and potassium, oxytocin secreting action, reproduction and reproductive function [Peptides, Vol. 17, 171(1996); Peptides, Vol. 18, 1095(1997), Peptides, Vol, 15, 757(1994); Journal of Neuroendocrinology, Vol. 8, 57(1996); Critical Reviews in Neurobiology, Vol. 8, 221, (1994)].

MCH causes versatile pharmacological actions through MCH receptors which are present mainly in the central nervous system. As receptors of MCH, at least two types of type 1 receptors (MCH-1R or SLC-1) and type 2 receptors (MCH-2R or SLT) are known [Nature, Vol. 400, 261(1999); Nature, Vol. 400, 265(1999); Biochemical and Biophysical Research Communications, Vol. 261, 622(1999); Nature Cell Biology, Vol. 1, 267(1999); FEBS Letters, Vol. 457, 522(1999); Biochemical and Physical Research Communications, Vol. 283, 1013 (2001); The Journal of Biological Chemistry, Vol. 276, 20125(2001); Proceedings of the National Academy of Sciences of the United States of America, Vol. 98, 7564(2001); Proceedings of the National Academy of Sciences of the United States of America, Vol. 98, 7576(2001); The Journal of Biological Chemistry, Vol. 276, 34664(2001); and Molecular Pharmacology, Vol. 60, 632(2001)].

Of those, the pharmacological action observed on rodents is induced mainly via MCH-1R [Genomics, Vol. 79, 785 (2002)]. Because MCH-1R gene-deficient mice chronically administered with MCH do not develop polyphagy or obesity, it is known that controlling of energy exchange by MCH is induced via MCH-1R. Furthermore, deficiency of MCH-1R promotes activity amount of mouse [Proceedings of the National Academy of Sciences of the United States of America, Vol. 99, 3240(2002)], and its participation in central diseases accompanied by behavioral disorder, for example, attention-deficit hyperactivity disorder, schizophrenia and the like also is strongly suggested [Molecular Medicine Today, Vol. 6, 43 (2000); Trends in Neuroscience, Vol. 24, 527(2001)].

It is also reported that autoantibody to MCH-1R is present in serum of vitiligo vulgaris patient [The Journal of Clinical Investigation, Vol. 109, 923(2002)]. Furthermore, expression of MCH-1R in certain species of cancer cells was reported, and in vivo expression sites of MCH and MCH-1R also suggest their participation in cancer, sleep, vigil, drug dependence and digestive disorders [Biochemical and Biophysical Research Communications, Vol. 289, 44 (2001); Neuroendocrinology, Vol. 61, 348(1995); Endocrinology, Vol. 137, 561 (1996); The Journal of Comparative Neurology, Vol. 435, 26 (2001)].

Functions of MCH are expressed upon its binding to MCH receptors. Therefore, when its binding to MCH receptor is inhibited, expression of MCH action can be inhibited. In consequence, substances which are antagonists to binding of MCH with its receptor are useful as preventing or treating agent of those various diseases in which MCH participates, for example, metabolic disorders represented by obesity, diabetes, hormone disorder, hyperlipidemia, gout, fatty liver, hepatitis and cirrhosis; cardiovascular disorders, represented by stenocardia, acute or congestive heart failure, myocardial infarction, coronary atherosclerosis, hypertension, renal diseases and electrolyte abnormality; central nervous system or peripheral nervous system disorders represented by bulimia, emotional disturbance, depression, anxiety, epilepsy, delirium, dementia, schizophrenia, attention-deficit hyperactivity disorder, memory impairment, sleep disorders, cognitive failure, dyskinesia paresthesias, smell disorders, morphine tolerance, drug dependence and alcoholism; reproductive disorders represented by infertility, preterm labor and sexual dysfunction; digestive disorders; respiratory disorders; cancer or pigmentation.

As compounds analogous to those of the present invention are known from, for example, JP Hei 3(1991)-109378A or JP Hei 10(1998)-500960 (International Publication WO 95/32967 Pamphlet). Whereas, the compounds disclosed in JP Hei 3-109378A have amino groups at 6-position of benzimidazole, differently from the compounds of the present invention which have amido groups. The utilities also are different. (The utility disclosed in JP Hei 3-109378A is their action to inhibit agglutination of thrombocytes.) On the other hand, JP Hei 10-500960 discloses the following compounds:

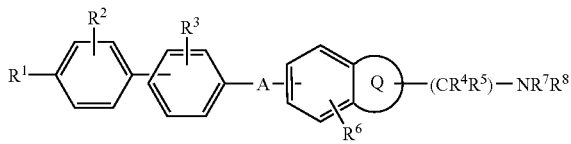

These compounds possess 5HT1D-antagonistic activity. Although they include benzimidazole skeletal structure, they differ from the compounds of the present invention in action mechanism and utility. The compounds of the present invention, furthermore, differ from the above compounds in their substituent moiety W.

Whereas, as heretofore known antagonists to melanin-concentrating hormone receptor, descriptions are found in, for example, International Publications WO 01/21577 Pamphlet, WO 01/82925 Pamphlet and WO 02/02744 Pamphlet; and in JP 2002-3370A. In particular, JP 2002-3370A discloses compounds represented by the following general formula as antagonists to melanin-concentrating hormone receptor.

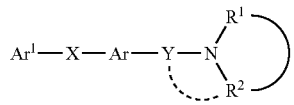

However, the essence of the invention of this prior art is to adopt as Ar a monocyclic aromatic ring which may condense with non-aromatic ring, and from which benzimidazole ring which is adopted by the present invention cannot be inferred. It is furthermore impossible to be led to the present invention in which the compounds exhibit excellent action due to specific substituent groups disposed at specific sites of benzimidazole ring.

We have engaged in concentrative studies with the view to develop compounds which inhibit binding of MCH to MCH-1R, to discover that benzimidazole derivatives characterized by having 1) alkylamino group at 2-position of the benzimidazole skeleton and 2) a specific substituent group at 6-position, via amido group, are novel substances not having been disclosed in any literature; and that specific compounds including said compounds are effective as MCH-1R antagonists; and come to complete the present invention based on those discoveries.

DISCLOSURE OF THE INVENTION

Namely, the present invention provides:

(1) an antagonist to melanin-concentrating hormone receptor comprising as the active ingredient a benzimidazole derivative represented by the following general formula [I]

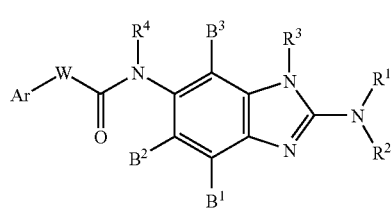

[in which $B^1$, $B^2$ and $B^3$ are same or different and each stands for hydrogen, halogen, lower alkyl or lower alkyloxy; $R^1$ and $R^2$ are same or different and each stands for
1) hydrogen,
2) a 3-10 membered aliphatic ring group of the formula [A]

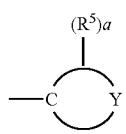

(in which $R^5$ either stands for a substituent selected from the later specified Group α, or two $R^5$'s together form oxo group; Y stands for —CH—, —$NR^6$— or —O—, $R^6$ standing for a substituent selected from a group consisting of hydrogen, optionally fluorine-substituted lower alkyl, lower alkylcarbonyl, lower alkyloxycarbonyl, lower alkylsulfonyl, carbamoyl, mono-lower alkylcarbamoyl and di-lower alkylcarbamoyl; and a is an integer of 0-4),
3) a lower alkyl group which optionally has substituent(s) selected from Group a given later or a 3-10 membered aliphatic ring group represented by the formula [A], or $R^1$ and $R^2$ together form, with the nitrogen atom to which they bind, a 3-10 membered aliphatic, nitrogen-containing heterocycle of the formula [B]

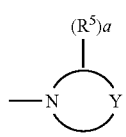

(in which $R^5$, Y and a are same as previously defined), provided $R^1$ and $R^2$ are not hydrogen atoms at the same time, $R^3$ stands for hydrogen or a lower alkyl which optionally has substituents selected from Group α, $R^4$ stands for hydrogen or a lower alkyl, W is a divalent group and stands for
1) linker,
2) mono- or bi-cyclic, 3-8 membered aromatic or aliphatic heterocycle,
3) mono- or bi-cyclic, 3-8 membered aromatic or aliphatic carbocycle, or
4) $C_2$-$C_4$ alkylene or alkenylene, whose carbon atom(s) in the main chain being optionally substituted with oxygen atom(s);

Ar stands for mono- or bi-cyclic, aromatic carbocycle or aromatic heterocycle, optionally having one, two or more substitutents selected from Group β;

[Group α]
halogen, hydroxyl, amino, mono-lower alkylamino, di-lower alkylamino, optionally fluorine-substituted lower alkyloxy, lower alkyloxycarbonyl, (lower alkyloxycarbonyl)amino, (lower alkyloxycarbonyl)lower alkylamino, lower alkylcarbonyl, lower alkylcarbonyloxy, (lower alkylcarbonyl) amino, (lower alkylcarbonyl) lower alkylamino, carbamoyl, mono-lower alkylcarbamoyl, di-lower alkylcarbamoyl, carbamoylamino, mono-lower alkylcarbamoylamino, di-lower alkylcarbamoylamino, (mono-lower alkylcarbamoyl)lower alkylamino, (di-lower alkylcarbamoyl)lower alkylamino, carbamoyloxy, mono-lower alkylcarbamoyloxy, di-lower alkylcarbamoyloxy, lower alkylsulfonyl, lower alkylsulfonylamino, sulfamoyl, mono-lower alkylsulfamoyl, di-lower alkylsulfamoyl, sulfamoylamino, (mono-lower alkylsulfamoyl)amino, (di-lower alkylsulfamoyl)amino, (mono-lower alkylsufamoyl)lower alkylamino and (di-lower alkylsulfamoyl)lower alkylamino.

[Group β]

halogen, hydroxyl, amino, cyano, mono-lower alkylamino, di-lower alkylamino, optionally fluorine-substituted lower alkyl, optionally fluorine-substituted lower alkyloxy, lower alkyloxycarbonyl, (lower alkyloxycarbonyl)amino, (lower alkyloxycarbonyl)lower alkylamino, carboxyl, lower alkylcarbonyl, lower alkylcarbonyloxy, (lower alkylcarbonyl)amino, (lower alkylcarbonyl)lower alkylamino, di-lower alkylcarbamoyl, di-lower alkylcarbamoylamino, (di-lower alkylcarbamoyl)lower alkylamino, di-lower alkylcarbamoyloxy, lower alkylsulfonyl, lower alkylsufonylamino, di-lower alkylsulfamoyl, sulfamoylamino, (di-lower alkylsulfamoyl) amino, (di-lower alkylsulfamoyl)lower alkylamino, and 5-6 membered aliphatic carbocycle or heterocycle which is optionally substituted with a group selected from group γ;

[Group γ]

Lower alkylcarbonyl, lower alkylsulfonyl and lower alkyloxycarbonyl]

or their pharmaceutically acceptable salts.

The invention furthermore provides (2) preventing or treating agents containing the antagonist as described in (1) as the active ingredient, for metabolic disorders represented by obesity, diabetes, hormone disorder, hyperlipidemia, gout, fatty liver, hepatitis and cirrhosis; cardiovascular disorders represented by stenocardia, acute or congestive heart failure, myocardial infarction, coronary atherosclerosis, hypertension, renal diseases and electrolyte abnormality; central nervous system or peripheral nervous system disorders represented by bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence and alcoholism; reproductive disorders represented by infertility, preterm labor and sexual dysfunction; digestive disorders; respiratory disorders; cancer or pigmentation.

(3) Compounds represented by the following general formula [I-1]

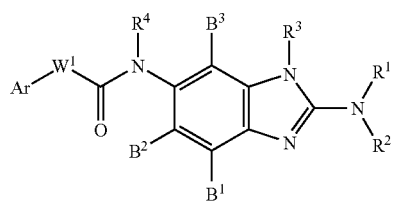

[in which
$W^1$ is a divalent group which stands for
1) linker,
2) mono- or bi-cyclic, 3-8 membered aromatic or aliphatic heterocycle,
3) mono- or bi-cycle, 3-8 membered aliphatic carbocycle, or 4) $C_2$-$C_4$ alkylene or alkenylene, whose carbon atom(s) being optionally substituted with oxygen atom(s);
$B^1$, $B^2$, $B^3$, $R^1$, $R^2$, $R^3$, $R^4$ and Ar are same as those defined in (1)]

or their pharmaceutically acceptable salts.

(4) Medical compositions comprising the compounds as described in (3) and pharmaceutically acceptable carriers.

(5) A process for producing a compound represented by the general formula [I], which comprises a step of condensing a compound of a general formula [II]

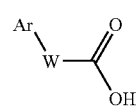

[in which Ar and W are same to those as previously defined] with a compound of a general formula [III]

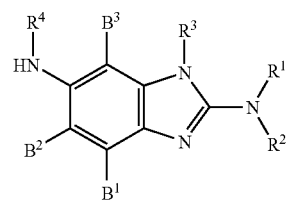

[in which $B^1$, $B^2$, $B^3$, $R^1$, $R^2$, $R^3$, $R^4$ are as previously defined].

Hereinafter the codes and terms used in the present specification are explained.

As "halogen", fluorine, chlorine, bromine and iodine can be named.

"Lower alkyl" includes $C_1$-$C_6$ alkyl, i.e., $C_1$-$C_6$ straight chain alkyl and $C_3$-$C_6$ branched alkyl, specific examples being methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl and the like.

"Lower cycloalkyl" includes $C_3$-$C_6$ cycloalkyl, specific examples being cyclopropyl, cyclobutyl, cyclopentyl and cyclohexyl.

"Oxo" signifies a group which, together with a carbon atom in an organic compound, forms carbonyl. For example, as to $R^5$, it refers to the case where two $R^5$'s and the carbon atom to which they bind form a carbonyl group.

"Optionally fluorine-substituted lower alkyl" includes lower alkyl and lower alkyl whose part or all of hydrogen atoms are substituted with fluorine atoms, examples of the latter fluorine-substituted lower alkyl being fluoromethyl, difuoromethyl, trifluoromethyl, 1,2-difluoroethyl and the like.

"Optionally fluorine-substituted lower alkyloxy" includes those groups in which lower alkyl or fluorine-substituted lower alkyl binds to oxygen, specific examples being: as lower alkyloxy, methoxy, ethoxy, n-propyloxy, isopropyloxy, n-butyloxy, isobutoxy, tert-butoxy, n-pentyloxy and the like;

and as fluorine-substituted lower alkyloxy, fluoromethoxy, difluoromethoxy, trifluoromethoxy, 1,2-difluoroethoxy and the like.

"Mono-lower alkylamino" is an amino in which one of its hydrogen atoms is mono-substituted with lower alkyl, specific examples being methylamino, ethylamino, n-propylamino, isopropylamino, n-butylamino, sec-butylamino, tert-butylamino and the like.

"Di-lower alkylamino" is an amino whose two hydrogen atoms are substituted with lower alkyl groups, specific examples being dimethylamino, diethylamino, ethylmethylamino, di(n-propyl)amino, methylpropylamino, diisopropylamino and the like.

"Lower alkyloxycarbonyl" is a carbonyl to which lower alkyloxy is bound, which includes $C_1$-$C_6$ alkyloxycarbonyl, specific examples being methoxycarbonyl, ethoxycarbonyl, n-propyloxycarbonyl, isopropyloxycarbonyl, n-butyloxycarbonyl, isobutoxycarbonyl, tert-butoxycarbonyl, n-pentyloxycarbonyl, and the like.

"(Lower alkyloxycarbonyl)amino" is an amino to which lower alkyloxycarbonyl is bound, which includes $C_1$-$C_6$ alkyloxycarbonylamino, specific examples being methoxycarbonylamino, ethoxycarbonylamino, n-propyloxycarbonylamino, isopropyloxycarbonylamino, n-butoxycarbonylamino, isobutoxycarbonylamino, tert-butoxycarbonylamino, n-pentyloxycarbonylamino and the like.

"(Lower alkyloxycarbonyl)lower alkylamino" is a mono-lower alkylamino whose hydrogen on the nitrogen atom is substituted with a lower alkyloxycarbonyl. As specific examples, (methoxycarbonyl)methylamino, (ethoxycarbonyl)methylamino, (n-propyloxycarbonyl)methylamino and the like can be named.

"Lower alkylcarbonyl" is a carbonyl to which lower alkyl is bound, which includes $C_1$-$C_6$ alkylcarbonyl, specific examples being acetyl, propionyl, butyryl, isobutyryl, valeryl, isovaleryl, pivaloyl and the like.

"Lower alkylcarbonylamino" is an amino one of whose hydrogen atoms is substituted with lower alkylcarbonyl, specific examples being acetamido, propionylamino, isobutyrylamino, valerylamino, isovalerylamino, pivaloylamino and the like.

"(Lower alkylcarbonyl)lower alkylamino" is a mono-lower alkylamino in which the hydrogen on its nitrogen atom is substituted with lower alkylcarbonyl, examples of which including (methylcarbonyl)methylamino, (ethylcarbonyl)methylamino, (n-propylcarbonyl)methylamino and the like.

"Lower alkylcarbonyloxy" is a group in which a lower alkylcarbonyl is bound to oxygen, specific examples including acetoxy, propionyloxy, valeryloxy, isovaleryloxy, pivaloyloxy and the like.

"Mono-lower alkylcarbamoyl" is a carbamoyl one of whose hydrogen atoms is substituted with lower alkyl, specific examples including methylcarbamoyl, ethylcarbamoyl, n-propylcarbamoyl, isopropylcarbamoyl, n-butylcarbamoyl, sec-butylcarbamoyl, tert-butylcarbamoyl and the like.

"Di-lower alkylcarbamoyl" is a carbamoyl whose two hydrogen atoms are substituted with lower alkyl groups, specific examples including dimethylcarbamoyl, diethylcarbamoyl, ethylmethylcarbamoyl, di(n-propyl)carbamoyl, methylpropylcarbamoyl, diisopropylcarbamoyl and the like.

"Mono-lower alkylcarbamoylamino" is an amino one of whose hydrogen atoms is substituted with mono-lower alkylcarbamoyl group, specific examples including methylcarbamoylamino, ethylcarbamoylamino, n-propylcarbamoylamino, isopropylcarbamoylamino, n-butylcarbamoylamino, sec-butylcarbamoylamino, tert-butylcarbamoylamino and the like.

"Di-lower alkylcarbamoylamino" is an amino one of whose hydrogen atoms is substituted with di-lower alkylcarbamoyl, specific examples including dimethylcarbamoylamino, diethylcarbamoylamino, di(n-propyl)carbamoylamino, diisopropylcarbamoylamino, di(n-butyl)carbamoylamino, di(sec-butyl)carbamoylamino, di(tert-butyl)carbamoylamino, and the like.

"(Mono-lower alkylcarbamoyl)lower alkylamino" is a mono-lower alkylamino whose hydrogen on the nitrogen atom is substituted with lower alkylcarbamoyl, specific examples including (monomethylcarbamoyl)methylcamino, (monoethylcarbamoyl)methylamino, [mono(n-propyl)carbamoyl]methylamino, and the like.

"(Di-lower alkylcarbamoyl)lower alkylamino" is a mono-lower alkylamino whose hydrogen on the nitrogen atom is substituted with di-lower alkylcarbamoyl, specific examples including (dimethylcarbamoyl)methylamino, (diethylcarbamoyl)methylamino, [di(n-propyl)carbamoyl]methylamino and the like.

"Mono-lower alkylcarbamoyloxy" is a group in which lower alkylcarbamoyl is bound to oxygen, specific examples including methylcarbamoyloxy, ethylcarbamoyloxy, n-propylcarbamoyloxy, isopropylcarbamoyloxy, n-butylcarbamoyloxy, sec-butylcarbamoyloxy, tert-butylcarbamoyloxy and the like.

"Di-lower alkylcarbamoyloxy" is a group in which di-lower alkylcarbamoyl is bound to oxygen, specific examples including dimethylcarbamoyloxy, diethylcarbamoyloxy, ethylmethylcarbamoyloxy, di(n-propyl)carbamoyloxy, methylpropylcarbamoyloxy, diisopropylcarbamoyloxy and the like.

"Lower alkylsulfonyl" is a group in which lower alkyl is bound to sulfonyl, specific examples including methylsulfonyl, ethylsulfonyl, n-propylsulfonyl, isopropylsulfonyl, n-butylsulfonyl, sec-butylsulfonyl, tert-butylsulfonyl and the like.

"Lower alkylsulfonylamino" is an amino one of whose hydrogen atoms is substituted with lower alkylsulfonyl, specific examples including methylsulfonylamino, ethylsulfonylamino, n-propylsulfonylamino, isopropylsulfonylamino, n-butylsulfonylamino, sec-butylsulfonylamino, tert-butylsulfonylamino and the like.

"Mono-lower alkylsulfamoyl" is a sulfamoyl one of whose hydrogen atoms is substituted with lower alkyl, specific examples including monomethylsulfamoyl, monoethylsulfamoyl, mono(n-propyl)sulfamoyl, monoisopropylsulfamoyl, mono(n-butyl)sulfamoyl, mono(sec-butyl)sulfamoyl, mono(tert-butyl)sulfamoyl and the like.

"Di-lower alkylsulfamoyl" is a sulfamoyl whose two hydrogen atoms are substituted with lower alkyl groups, specific examples including dimethylsulfamoyl, diethylsulfamoyl, di(n-propyl)sulfamoyl, diisopropylsulfamoyl, di(n-butyl)sulfamoyl, di(sec-butyl)sulfamoyl, di(tert-butyl)sulfamoyl and the like.

"(Mono-lower alkylsulfamoyl)amino" is an amino one of whose hydrogen atoms is substituted with mono-lower alkylsulfamoyl, specific examples including (monomethylsulfamoyl)amino, (monoethylsulfamoyl)amino, [mono(n-propyl)sulfamoyl]amino, (monoisopropylsulfamoyl)amino, [mono(n-butyl)sulfamoyl]amino, [mono(sec-butyl)sulfamoyl]amino, (tert-butylsulfamoyl)amino and the like.

"(Di-lower alkylsulfamoyl)amino" is an amino one of whose hydrogen atoms is substituted with di-lower alkylsulfamoyl, specific examples including (dimethylsulfamoyl)amino, (diethylsulfamoyl)amino, (ethylmethylsulfamoyl)amino, [di(n-propyl)sulfamoyl]amino, (methylpropylsulfamoyl)amino, (diisopropylsulfamoyl)amino and the like.

"(Mono-lower alkylsulfamoyl)lower alkylamino" is a "mono-lower alkylamino" whose hydrogen on the nitrogen atom is substituted with mono-lower alkylsulfamoyl, specific examples including (monomethylsulfamoyl)methylamino, (monoethylsulfamoyl) methylamino, [mono(n-propyl)sulfamoyl]methylamino and the like.

"(Di-lower alkylsulfamoyl)lower alkylamino" is a "mono-lower alkylamino" whose hydrogen on the nitrogen atom is substituted with di-lower alkylsulfamoyl, specific examples including (dimethylsulfamoyl)methylamino, (diethylsulfamoyl)methylamino, [di(n-propyl)sulfamoyl]methylamino and the like.

As "3-10 membered aliphatic ring groups" in the formula A, aliphatic carbocycles such as cyclopropyl, cyclobutyl, cyclopentyl, cyclohexyl, cycloheptyl, cyclooctyl, cycloheptenyl, cyclopentenyl, cyclohexenyl, and the like; aliphatic, nitrogen-containing heterocycles such as azetidinyl, pyrrolidinyl, piperidinyl, hexamethyleneiminyl, heptamethyleneiminyl, 1,4-diazepanyl, piperazinyl, morpholinyl and the like; and aliphatic oxygen-containing heterocycles such as tetrahydrofuranyl, tetrahydropyranyl and the like can be named.

As "3-10 membered aliphatic, nitrogen-containing heterocyclic groups" in the formula B, azetidin-1-yl, pyrrolidin-1-yl, piperidin-1-yl, hexamethyleneimin-1-yl, heptamethyleneimin-1-yl, piperazin-1-yl, 1,4-diazepan-1-yl, morpholin-1-yl and the like can be named.

As the substituent groups selected from the Group α, the following can be named:

[Group α]
halogen, hydroxyl, amino, mono-lower alkylamino, di-lower alkylamino, optionally fluorine-substituted lower alkyloxy, lower alkyloxycarbonyl, (lower alkyloxycarbonyl) amino, (lower alkyloxycarbonyl)lower alkylamino, carboxyl, lower alkylcarbonyl, lower alkylcarbonyloxy, (lower alkylcarbonyl)amino, (lower alkylcarbonyl)lower alkylamino, carbamoyl, mono-lower alkylcarbamoyl, di-lower alkylcarbamoyl, carbamoylamino, mono-lower alkylcarbamoylamino, di-lower alkylcarbamoylamino, (mono-lower alkylcarbamoyl)lower alkylamino, (di-lower alkylcarbamoyl) lower alkylamino, carbamoyloxy, mono-lower alkylcarbamoyloxy, di-lower alkylcarbamoyloxy, lower alkylsulfonyl, lower alkylsulfonylamino, sulfamoyl, mono-lower alkylsulfamoyl, di-lower alkylsulfamoyl, sulfamoylamino, (mono-lower alkylsulfamoyl)amino, (di-lower alkylsulfamoyl)amino, (mono-lower alkylsufamoyl)lower alkylamino and (di-lower alkylsufamoyl)lower alkylamino.

Also the substituent groups selected from Group β, the following can be named:

[Group β]
Halogen, hydroxyl, amino, cyano, mono-lower alkylamino, di-lower alkylamino, optionally fluorine-substitited lower alkyl, optioinally fluorine-substituted lower alkyloxy, lower alkyloxycarbonyl, (lower alkyloxycarbonyl)amino, (lower alkyloxycarbonyl)lower alkylamino, carboxyl, lower alkylcarbonyl, lower alkylcarbonyloxy, (lower alkylcarbonyl)amino, (lower alkylcarbonyl)lower alkylamion, di-lower alkylcarbamoyl, di-lower alkylcarbamoylamino, (di-lower alkylcarbamoyl)lower alkylamino, di-lower alkylcarbamoyloxy, lower alkylsulfonyl, lower alkylsulfonylamino, di-lower alkylsulfamoyl, sulfamoylamino, (di-lower alkylsulfamoyl)amino, (di-lower alkylsulfamoyl)lower alkylamino, and 5- or 6-membered aliphatic carbocycles or heterocycles optionally having a substituent selected from Group γ.

As examples of "5- or 6-membered aliphatic carbocycles or heterocycles" in Group β, cyclopentyl, cyclohexyl, pyrrolidine, piperazine, piperidine, morpholine and the like can be named.

As the substituent groups selected from Group γ, the following can be named:

[Group γ]
Lower alkylcarbonyl, lower alkylsulfonyl and lower alkyloxycarbonyl.

"Pharmaceutically acceptable salts" of the benzimidazole derivatives that are represented by the general formula [I] signify those customarily used salts which are permissible to be used in drug, specific examples including acid addition salts at amino or at nitrogen-containing heterocycle or, where the derivatives contain carboxyl, base addition salts at the carboxyl.

As such acid addition salts, inorganic acid salts such as hydrochloride, sulfate, nitrate, phosphate, perchlorate and the like; organic acid salts such as maleate, fumarate, tartarate, citrate, ascorbate, trifluoroacetate and the like; and sulfonic acid salts such as methanesulfonate, isethionate, benzenesulfonate, p-toluenesulfonate and the like can be named.

As the base addition salts, alkali metal salts such as sodium salt, potassium salt and the like; alkaline earth metal salts such as calcium salt, magnesium salt and the like; and organic amine salts such as ammonium salt, trimethylamine salt, triethylamine salt, dicyclohexylamine salt, ethanolamine salt, diethanolamine salt, triethanolamine salt, procaine salt, N,N'-dibenzylethylenediamine salt and the like can be named.

For still more specific disclosure of the benzimidazole derivatives of the present invention, symbols used in the formula [I] are explained in details, citing specific examples. The position numbers assigned to benzimidazole skeleton are as on the formula below:

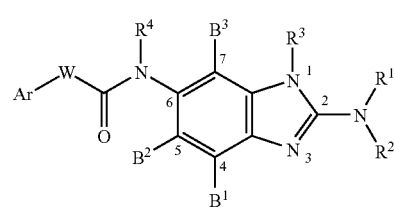

Compounds Represented by the General formula [I]

In the compounds represented by the general formula [I], $B^1$, $B^2$ and $B^3$ may be same or different, and each stands for, for example, hydrogen, halogen, lower alkyl or lower alkyloxy, preferably hydrogen or methyl, in particular, hydrogen.

$R^1$ and $R^2$ which may be same or different, each stands for
1) hydrogen,
2) 3-10 membered aliphatic ring group represented by the formula [A]

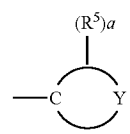

(in which $R^5$ either stands for a substituent selected from Group α, or two $R^5$'s together form an oxo; Y stands for —CH$_2$—, —NR$^6$— or —O—, R$^6$ being a substituent selected from a group consisting of hydrogen, optionally fluorine-substituted lower alkyl, lower alkylcarbonyl, lower alkyloxycarbonyl, lower alkylsulfonyl, carbamoyl, mono-lower alkylcarbamoyl and di-lower alkylcarbamoyl; and a stands for an integer of 0-4), 3) lower alkyl which may have substituent(s) selected from Group α or a 3-10 membered aliphatic ring group represented by the formula [A], or a group which forms, together with R$^1$ and R$^2$ and the nitrogen atom to which they bind, a 3-6 membered aliphatic, nitrogen-containing heterocycle represented by the formula [B]

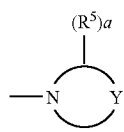

[B]

(in which R$^5$, Y and a are same to those as previously defined), with the proviso that R$^1$ and R are not hydrogen atoms at the same time.

In the groups represented by the formula [A] or [B], examples of preferred substituent groups selected from Group a are: fluoro, chloro, hydroxyl, amino, methoxy, ethoxy, trifluoromethoxy, methoxycarbonyl, ethoxycarbonyl, isopropyloxycarbonyl, tert-butyloxycarbonyl, methoxycarbonylamino, (methoxycarbonyl)methylamino, acetyl, ethylcarbonyl, n-propylcarbonyl, isopropylcarbonyl, acetoxy, acetamide, isopropylcarbonylamino, acetylmethylamino, (methylcarbonyl)methylamino, (isopropylcarbonyl)methylamino, carbamoyl, methylcarbamoyl, dimethylcarbamoyl, carbamoylamino, dimethylcarbamoylamino, (dimethylcarbamoyl)methylamino, carbamoyloxy, (dimethylcarbamoyl)oxy, methanesulfonyl, methanesulfonamide, sulfamoyl, dimethylsulfamoyl, sulfamoylamino, dimethylsulfamoylamino, (dimethylsulfamoyl)methylamino and the like. In particular, hydroxyl, amino, methoxy, ethoxy, acetyl, isopropyl carbonyl, acetoxy, tert-butyloxycarbonyl, methoxycarbonylamino, isopropylcarbonylamino and isopropylcarbonyl(methyl)amino are recommended.

As preferred R$^5$, hydrogen; lower alkylcarbonyl such as acetyl, ethylcarbonyl, n-propylcarbonyl, isopropylcarbonyl, and oxo are recommended. As preferred R$^6$ in Y, lower alkyl such as methyl, ethyl, isopropyl and the like; lower alkylcarbonyl such as acetyl, n-propylcarbonyl, isopropylcarbonyl and the like; lower alkyloxycarbonyl such as methoxycarbonyl, tert-butyloxycarbonyl and the like; and lower alkylsulfonyl such as methanesulfonyl and the like are recommended.

As specific examples of 3-10 membered aliphatic ring groups which are represented by the formula [A], cyclopropyl, cyclobutyl, cyclopentyl, cyclohexyl, pyrrolidin-3-yl, 1-methylpyrrolidin-3-yl, 1-acetylpyrrolidin-3-yl, 1-propionylpyrrolidin-3-yl, 1-(isopropylcarbonyl)pyrrolidin-3-yl, 1-methanesulfonylpyrrolidin-3-yl, piperidin-4-yl, 1-methylpiperidin-4-yl, 1-acetylpiperidin-4-yl, 1-(isopropylcarbonyl)piperidin-3-yl, 1-methanesulfonylpiperidin-3-yl, tetrahydrofuran-3-yl, 1-methylpyrrolidon-3-yl, 1-methylpyrrolidon-4-yl and the like can be named.

As specific examples of 3-10 membered aliphatic, nitrogen-containing heterocycles which are represented by the formula [B], azetidin-1-yl, pyrrolidin-1-yl, 2-hydroxymethylpyrrolidin-1-yl, 3-hydroxypyrrolidin-1-yl, 3-[acetyl(methyl)amino]pyrrolidinyl-yl, 3-[isopropylcarbonyl(methyl) amino]-pyrrolidin-1-yl, 3-[methanesulfonyl(methyl)amino]-pyrrolidin-1-yl, 3-(isopropylcarbonylamino)-pyrrolidin-1-yl, piperidin-1-yl, hexamethyleneimine-1-yl, heptamethyleneimine-1-yl, piperazin-1-yl, 4-acetylpiperazin-1-yl, 4-isopropylcarbonylpiperazin-1-yl, 1,4-diazepan-1-yl, morpholin-1-yl and the like can be named.

As specific R$^1$ or R$^2$, those preferred are hydrogen, methyl, ethyl, n-propyl, isopropyl, n-butyl, isobutyl, tert-butyl 1,1-dimethylpropyl, 2,2-dimethylpropyl, 1-ethylpropyl, 4-methylpentyl, 2-hydroxypropyl, 2-methoxypropyl, 2-hydroxy-2-methylpropyl, 2-methoxy-2-methylpropyl, 2-(methoxycarbonylamino)ethyl, 2-acetoxypropyl, 1-ethyl-2-hydroxy-2-methylpropyl, 2,2-dimethyl-1-oxopropyl, 2-hydroxy-1,2-dimethylpropyl, 2-methoxy-1,2-dimethylpropyl, 2-amino-2-methylpropyl, 2-hydroxyethyl, 1,3-dimethyl-3-hydroxybutyl, 1,3-dimethyl-3-methoxybutyl, 2-(methanesulfonamide)ethyl, methoxyethyl, cyclopropyl, cyclobutyl, cyclopentyl, cyclohexyl, pyrrolidin-3-yl, 1-methylpyrrolidin-3-yl, 1-acetylpyrrolidin-3-yl, 1-propionylpyrrolidin-3-yl, 1-(isopropylcarbonyl)pyrrolidin-3-yl, 1-methanesulfonylpyrrolidin-3-yl, 1-methylpiperidin-4-yl, 1-acetylpiperidin-4-yl, tetrahydrofuran-3-yl, 1-methylpyrrolidon-4-yl, 6-(N-acetylpyrrolidin-2-yl)methyl, (N-isopropylcarbonylpyrrolidin-2-yl)methyl and the like.

As preferred examples of 3-10 membered aliphatic, nitrogen-containing heterocyclic groups which are represented by the formula [B] which is formed by R$^1$ and R$^2$ together with the nitrogen atom to which they bind, azetidin-1-yl, pyrrolidin-1-yl, 3-hydroxypyrrolidin-1-yl, 3-[acetyl(methyl) amino]-pyrrolidin-1-yl, 3-[isopropylcarbonyl(methyl) amino]-pyrrolidin-1-yl, 3-[methanesulfonyl(methyl)amino]-pyrrolidin-1-yl, 3-(isopropylcarbonylamino)-pyrrolidin-1-yl, piperidin-1-yl, 2-hydroxymethylpyrrolidin-1-yl and the like can be named.

Of those, as more preferred R$^1$ or R$^2$, 1) lower alkyl which optionally has substituent(s) selected from Group α given later or 3-10 membered aliphatic ring group represented by the formula [A], for example, 2) those whose R$^1$ is methyl (or R$^2$ is methyl) are recommended; in particular, 3) those whose R$^1$ (or R$^2$) is methyl and R$^2$ (or R$^1$) is selected from the group consisting of isopropyl, cyclopropyl, cyclobutyl, cyclopentyl, cyclohexyl, N-methylpyrrolidin-3-yl, N-acetylpyrrolidin-3-yl, N-methylpiperidin-4-yl, tetrahydrofuran-2-yl, 1-methanesulfonylpyrrolidin-3-yl and 1-(isopropylcarbonyl)pyrrolidin-3-yl are recommended.

As examples of R$^3$, hydrogen or lower alkyl which may have substituents selected from Group a can be named, hydrogen or methyl being preferred.

As examples of R$^4$, hydrogen or lower alkyl can be named, hydrogen or methyl being preferred.

As examples of W which is a divalent group, 1) linker,
2) mono- or bi-cyclic, 3-8 membered aromatic or aliphatic heterocycle,
3) mono- or bi-cyclic, 3-8 membered aromatic or aliphatic carbocycle, or
4) C$_2$-C$_4$ alkylene or alkenylene, whose carbon atom(s) in the main chain being optionally substituted with oxygen atom(s)

can be named.

Said mono- or bi-cyclic, 3-8 membered aromatic heterocycle represented by W signifies divalent aromatic heterocyclic groups, examples of which include pyrrol-di-yl, pyridin-di-yl, pyrazin-di-yl, pyrimidin-di-yl, pyridazin-di-yl, 1,2,4-triazin-di-yl, oxazol-di-yl, isoxazol-di-yl, 1,2,4-oxadiazoldi-yl, 1,3,4-oxadiazol-di-yl, 1,2,4-triazol-di-yl, 1,2,3-triazol-di-yl, pyrazol-di-yl, 5-methylpyrazol-di-yl, 1-methylprazol-di-yl, tetrazol-di-yl, thiazol-di-yl, isothiazol-di-yl, thiadiazol-di-yl, imidazol-di-yl, indol-di-yl, benzimidazol-di-yl, benzoxazol-di-yl, benzisoxazol-di-yl, benzthiazol-di-yl, benzisothiazol-di-yl, indazolin-di-yl, prinin-di-yl, quinolin-di-yl, isoquinolin-di-yl, phthalazin-di-yl, naphthylidin-di-yl, quinoxalin-di-yl, quinazolin-di-yl, cinnolin-di-yl, pteridin-di-yl and the like.

Mono- or bi-cyclic, 3-8 membered aliphatic heterocycle represented by W signifies divalent aliphatic heterocycles, examples of which include aziridin-di-yl, pyrrolidin-di-yl, piperazin-di-yl, piperazin-2-on-di-yl, piperidin-di-yl and the like.

Mono- or bi-cyclic, 3-8 membered aromatic carbocycle represented by W signifies divalent aromatic carbocyclic groups, examples of which include 1,2-phenylene, 1,3-phenylene, 1,4-phenylene, 2,6-naphthalene and the like.

Mono- or bi-cyclic, 3-8 membered aliphatic carbocycle represented by W signifies divalent aliphatic carbocyclic groups, examples of which include 1,2-cyclopropylene, 1,3-cyclobutylene, 1,3-cyclopentylene, 1,2-cyclohexylene, 1,4-cyclohexylene and the like.

$C_2$-$C_4$ alkylene in which the carbon atom(s) in the main chain may be substituted with oxygen atom(s) as represented by W signifies $C_2$-$C_4$ alkylene groups with a part of their carbon atoms being optionally substituted with oxygen atom(s), examples of which include —CH$_2$CH$_2$—, —CH$_2$CH$_2$CH$_2$—, —CH$_2$CH(CH$_3$)—, —O—CH$_2$—, —O—CH(CH$_3$)—, —CH$_2$CH$_2$CH$_2$CH$_2$— and the like.

$C_2$-$C_4$ alkenylene in which the carbon atom(s) in the main chain may be substituted with oxygen atom(s) as represented by W signifies $C_2$-$C_4$ alkenylene groups with a part of their carbon atoms being optionally substituted with oxygen atom(s), examples of which include —CH=CH—, —CH=CH—CH$_2$—, —CH$_2$—CH=CH— and the like.

As W,
1) linker
2) mono- or bi-cyclic, 3-8 membered aromatic or aliphatic heterocycle,
3) mono- or bi-cyclic, 3-8 membered aliphatic carbocycle, and
4) $C_2$-$C_4$ alkylene or alkenylene in which the carbon atom(s) in the main chain may be substituted with oxygen atom(s) are preferred (the preferred are expressed as WI); in particular, one selected from the group consisting of
1) mono- or bi-cyclic, 3-8 membered aromatic or aliphatic heterocycle,
2) mono- or by-cyclic, 3-8 membered aliphatic carbocycle, and
3) $C_2$-$C_4$ alkylene in which the carbon atom(s) in the main chain may be substituted with oxygen atom(s) is recommended.

Of those, mono- or bi-cyclic, 3-8 membered aromatic nitrogen-containing heterocyclic groups are particularly preferred, examples of which include

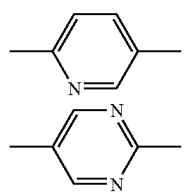
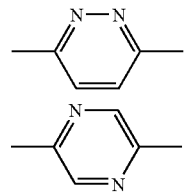

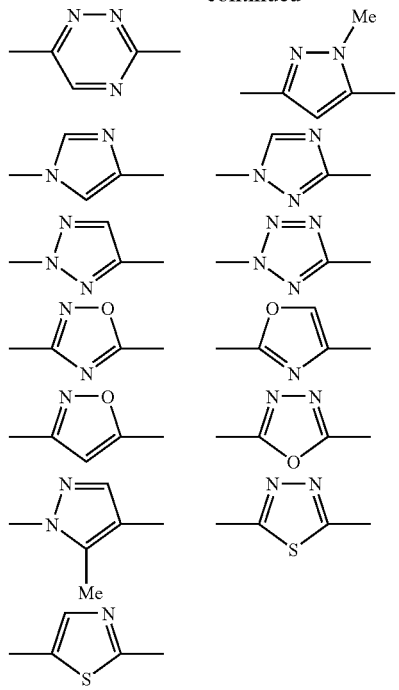

Inter alia, the following substituents are recommended:

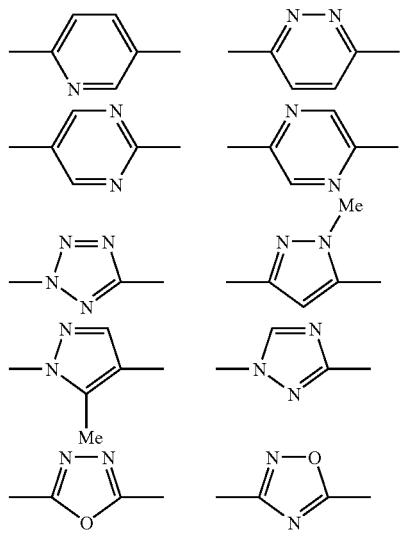

As Ar, for example,
1) mono- or bi-cyclic aromatic carbocycle which may have one or more substituents selected from Group β, and
2) mono- or bi-cyclic aromatic heterocycle which may have one or more substituents selected from Group β can be named.

Specific examples of "mono- or bi-cyclic aromatic carbocycle or aromatic heterocycle" as Ar include phenyl, naphthyl, pyrrolyl, furyl, thienyl, imidazolyl, pyrazolyl, thiazolyl, isothiazolyl, oxazolyl, isoxazolyl, triazolyl, tetrazolyl, oxadiazolyl, thiadiazolyl, pyridinyl, pyrazinyl, pyrimidinyl, pyridazinyl, indolyl, benzfuranyl, benzthienyl, benzimidazolyl, benzoxazolyl, benzisoxazolyl, benzthiazolyl, benzisothiazolyl, indazolyl, prinyl, quinolyl, isoquinolyl, phthalazinyl, naphthilidinyl, quinoxalinyl, quinazolinyl, cinnolinyl, pteridinyl and the like. Preferably, phenyl, pyridinyl, pyrimidinyl, pyrazinyl and pyridazinyl are recommended.

Preferred substituents selected from said Group β are fluoro, chloro, cyano, trifluoromethyl, methoxy, ethoxy, trifluoromethoxy, methoxycarbonyl, ethoxycarbonyl, tert-butyloxycarbonyl, methoxycarbonylamino, acetyl, acetoxy, acetamido, (methylcarbonyl)methylamino, dimethylcarbamoyl, dimethylcarbamoylamino, (dimethylcarbamoyl)methylamino, dimethylcarbamoyloxy, methanesulfonyl, methanesulfonamido, dimethylsulfamoyl, sulfamoylamino, (dimethylsulfamoyl)amino, (dimethylsulfamoyl)methylamino, cyclohexyl, morpholinyl, piperazinyl and the like. In particular, fluoro, chloro, cyano, trifluoromethyl, methoxy, cyclohexyl, morpholinyl and piperazino are recommended.

Specific examples of optioinally substituted mono- or bicyclic aromatic carbocycle as Ar include phenyl, 4-cyclohexylphenyl, 2-fluorophenyl, 3-fluorophenyl, 4-fluorophenyl, 3,4-difluorophenyl, 2,4-difluorophenyl, 2-chlorophenyl, 3-chlorophenyl, 4-chlorophenyl, 3-trifluoromethylphenyl, 4-trifluoromethylphenyl, 4-methoxyphenyl, 4-ethoxyphenyl, 3-fluoro-4-methoxyphenyl, 4-cyanophenyl, 4-(morpholino)phenyl, 4-(piperazino)phenyl, coumaranon-5-yl, naphthalene-1-yl and the like.

Specific examples of optionally substituted mono- or bicyclic aromatic heterocycle as Ar include 2-fluoropyridin-5-yl, 3-fluoropyridin-6-yl, 2-chloropyridin-5-yl, 3-chloropyridin-6-yl, 2-methoxypyridin-5-yl, 2-methoxypyridin-6-yl, 2-ethoxypyridin-5-yl, 2-ethoxypyridin-6-yl, 2-pyrimidinyl, 2-pyridinyl, (2-trifluoromethyl)pyridin-5-yl, (3-trifluoromethyl)pyridin-6-yl, 2-cyanopyridin-5-yl, 2-pyrazinyl, 3-pyridazinyl and the like.

As preferred Ar, phenyl, 2-fluorophenyl, 3-fluorophenyl, 4-fluorophenyl, 2-trifluoromethylphenyl, 3-trifluoromethylphenyl, 4-trifluoromethylphenyl, 4-methoxyphenyl, 4-methanesulfonylphenyl, 3-fluoro-4-methoxyphenyl, 3,4-difluorophenyl, 2,4-difluorophenyl, 4-chlorophenyl, 4-(piperidin-1-yl)phenyl, 4-(morpholin-1-yl)phenyl, 2-fluoropyridin-5-yl, 3-fluoropyridin-6-yl, 2-methoxypyridin-5-yl, 2-methoxypyridin-6-yl, 2-pyrimidinyl, 2-pyridinyl, (2-trifluoromethyl)-5-pyridinyl, (3-trifluoromethyl)-6-pyridinyl, 2-pyrazinyl, 3-pyridazinyl and the like are recommended.

According to the present invention, by adopting 1) as W, mono- or bi-cyclic 3-8 membered aromatic nitrogen-containing heterocycle and 2) as $R^1$, methyl, and as $R^2$, specific substituent group, the compounds having the characteristic properties of excelling in MCH-1R-inhibiting activity and in in vivo metabolic activity can be obtained, which exhibit excellent feeding inhibitory action.

According to the present invention, as forms of the preferred compounds,
1) compounds represented by a general formula [I-1]

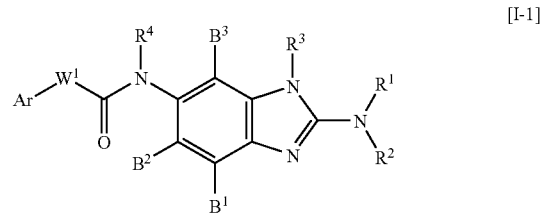

[in which $B^1$, $B^2$, $B^3$, $R^1$, $R^2$, $R^3$, $W^1$ and Ar are same to those as previously defined]; and
2) compounds represented by a general formula [I-2]

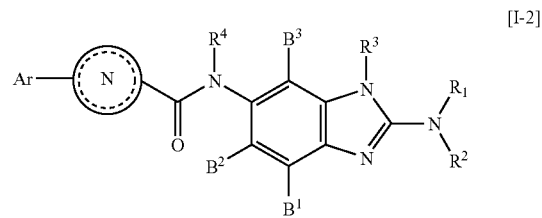

[in which

stands for a divalent, mono- or bi-cyclic 3-8 membered aromatic nitrogen-containing heterocyclic group; and $B^1$, $B^2$, $B^3$, $R^1$, $R^2$, $R^3$, $R^4$ and Ar are same to those as previously defined]

are recommended.

Examples of specific compounds of the present invention include the following.

| No | Structural Formula |
|---|---|
| 1 | 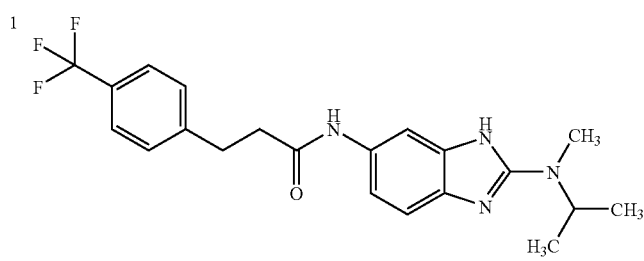 |

-continued
| No | Structural Formula |
|----|--------------------|
| 2 | 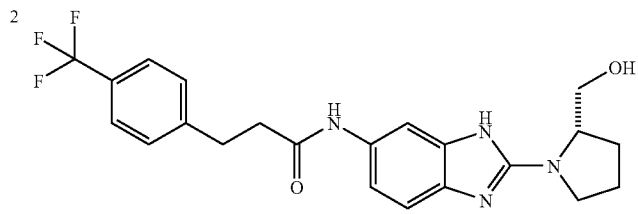 |
| 3 | 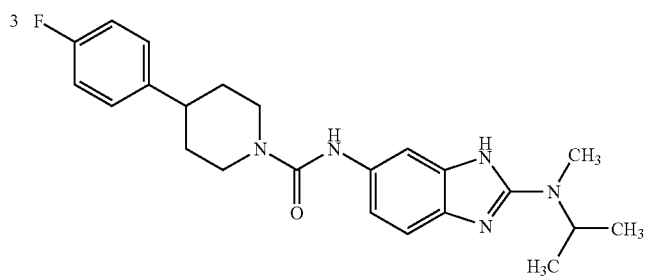 |
| 4 | 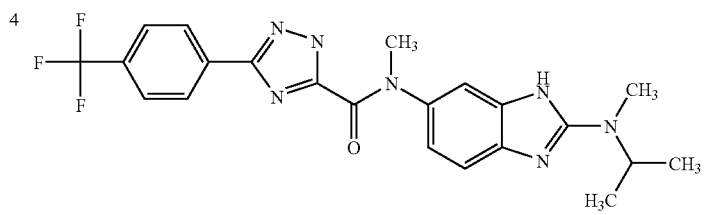 |
| 5 | 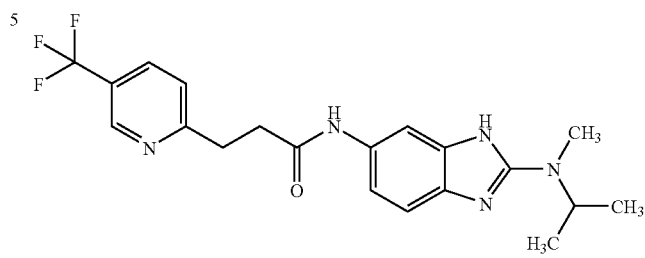 |
| 6 | 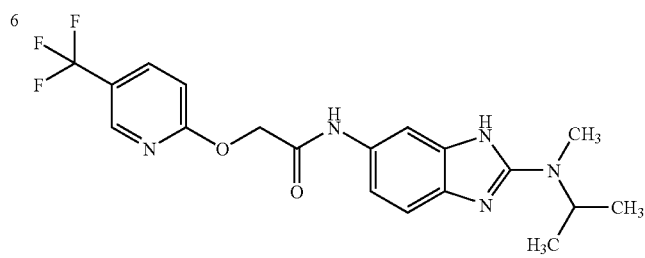 |
| 7 | 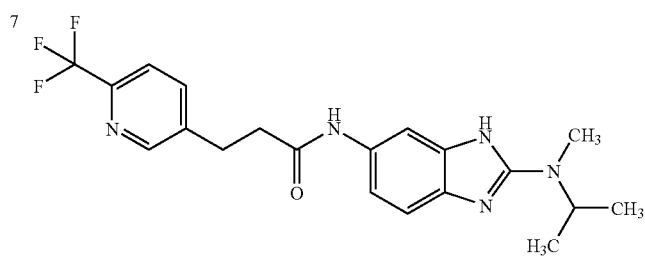 |

-continued
| No | Structural Formula |
|----|-------------------|
| 8 | 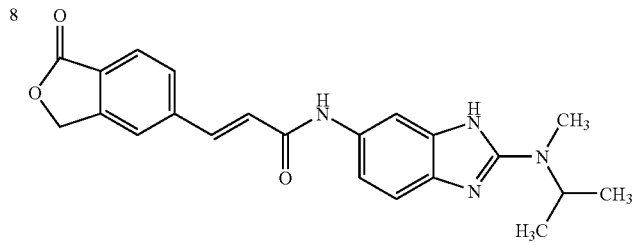 |
| 9 | 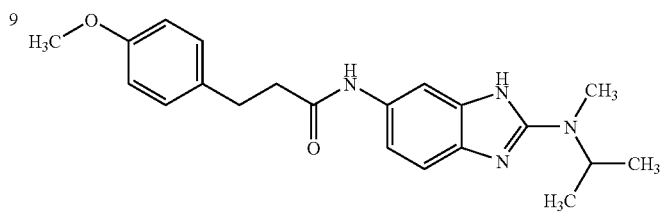 |
| 10 | 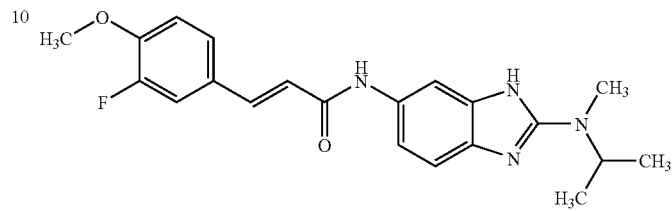 |
| 11 | 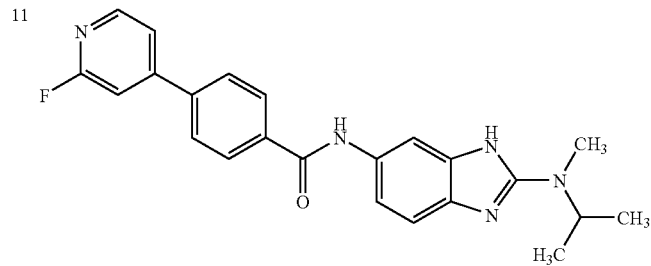 |
| 12 | 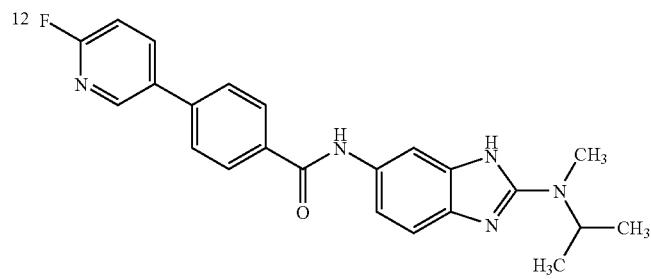 |
| 13 | 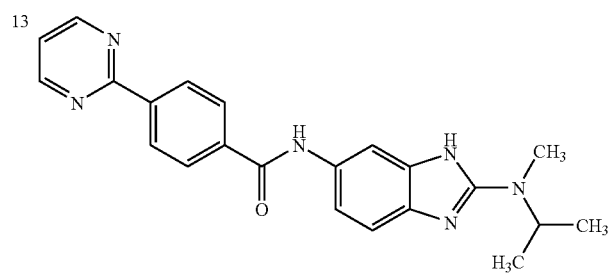 |

| No | Structural Formula |
|---|---|
| 14 | 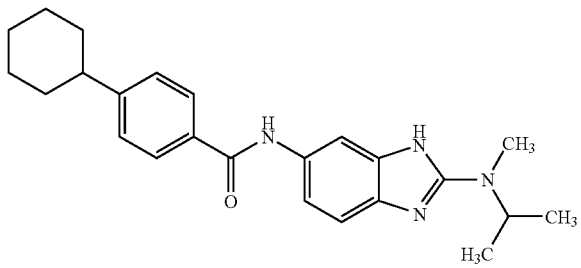 |
| 15 | 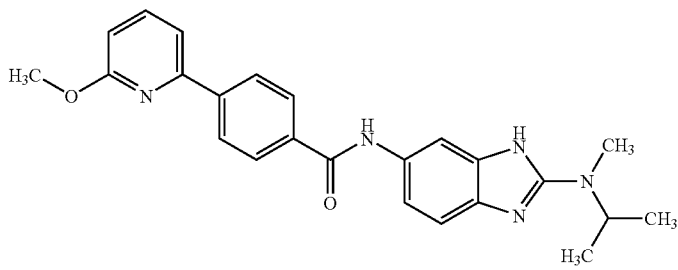 |
| 16 | 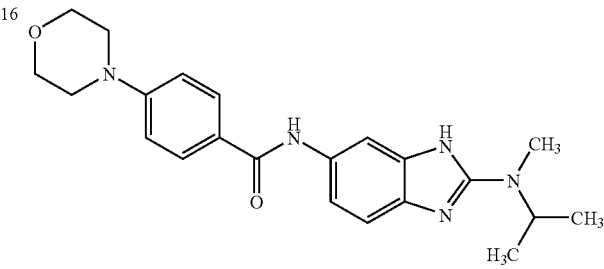 |
| 17 | 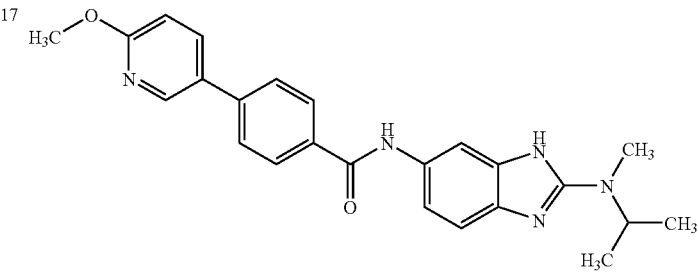 |
| 18 | 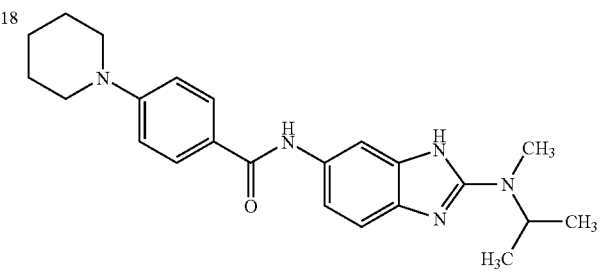 |

-continued
| No | Structural Formula |
|---|---|
| 19 | 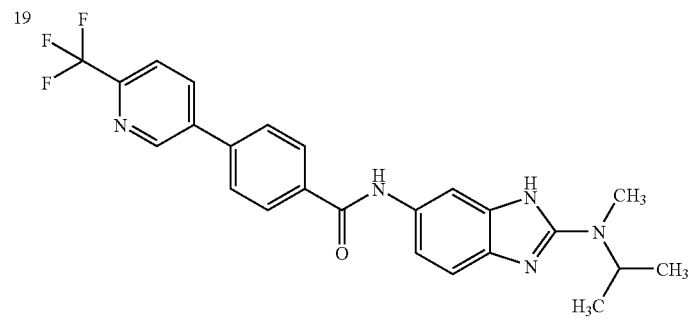 |
| 20 | 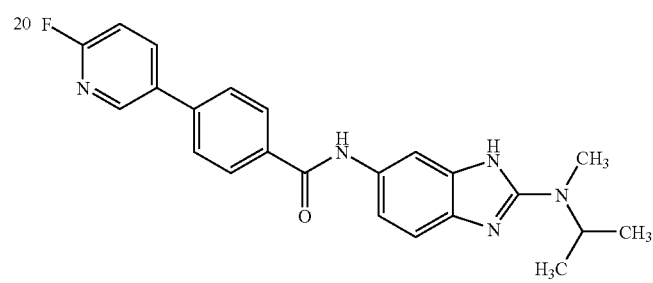 |
| 21 | 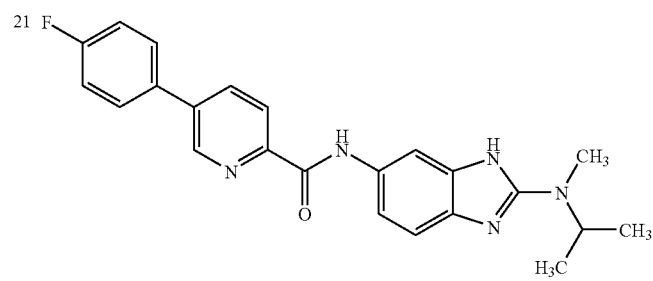 |
| 22 | 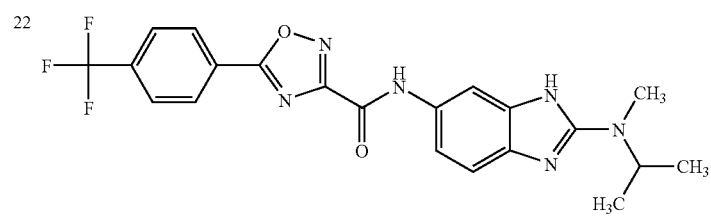 |
| 23 | 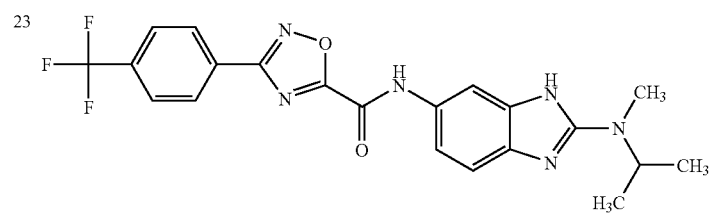 |
| 24 | 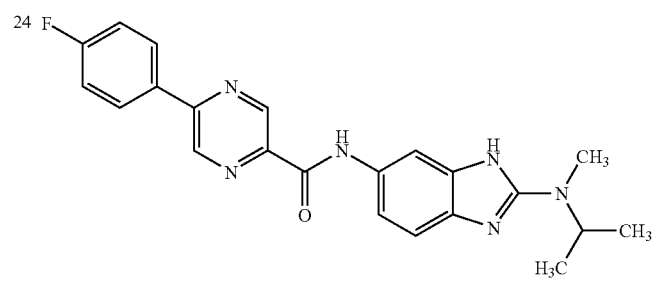 |

-continued
| No | Structural Formula |
|---|---|
| 25 | 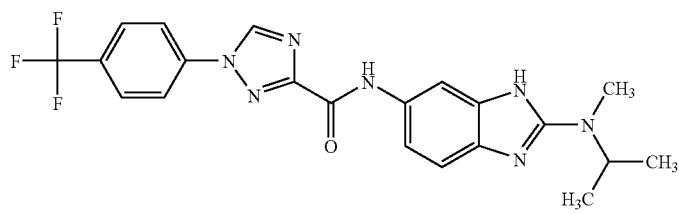 |
| 26 | 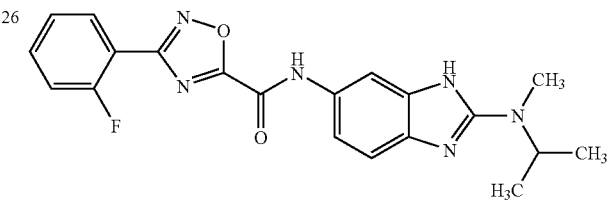 |
| 27 | 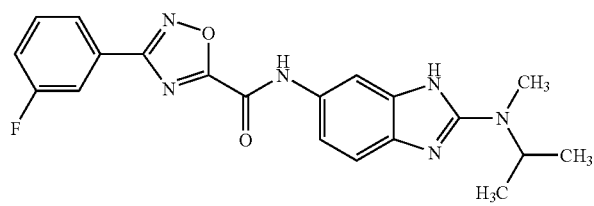 |
| 28 | 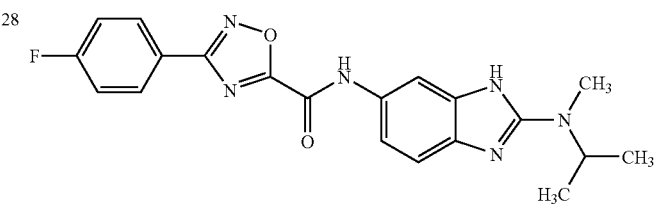 |
| 29 | 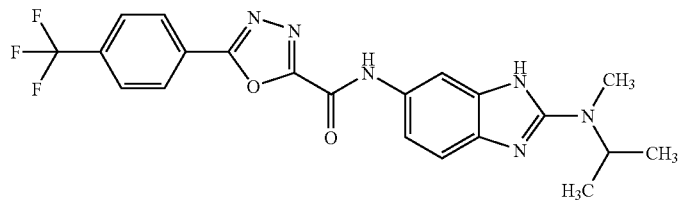 |
| 30 | 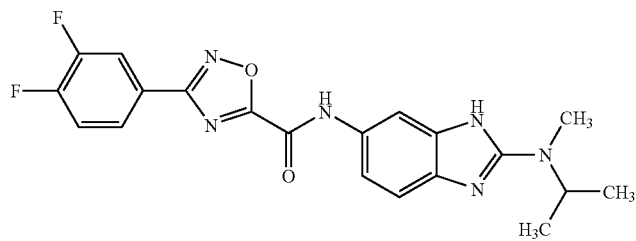 |

| No | Structural Formula |
|---|---|
| 31 | 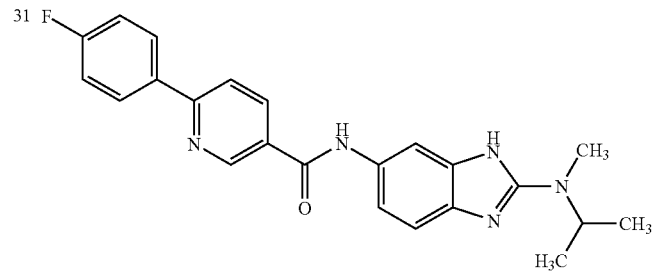 |
| 32 | 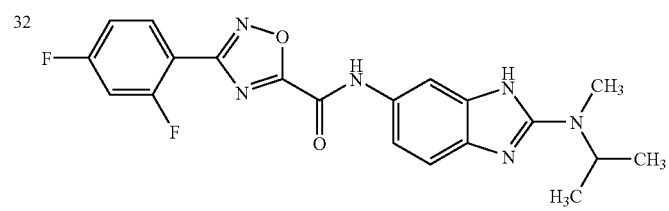 |
| 33 | 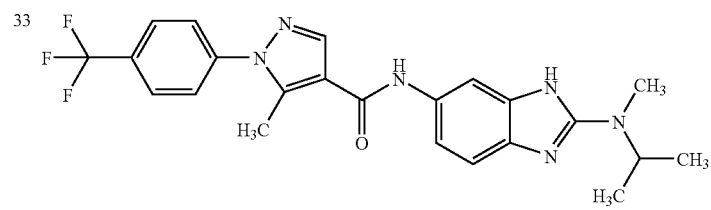 |
| 34 | 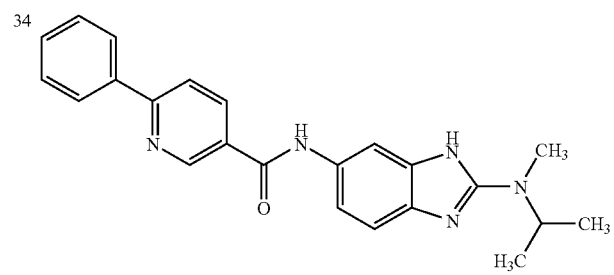 |
| 35 | 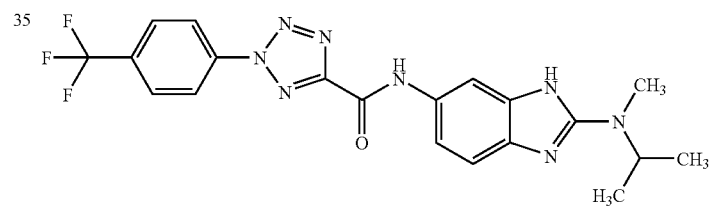 |
| 36 | 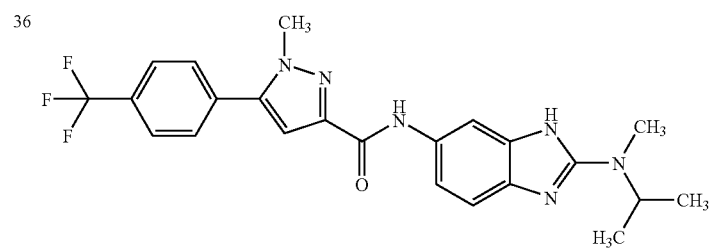 |

-continued
| No | Structural Formula |
|---|---|
| 37 | 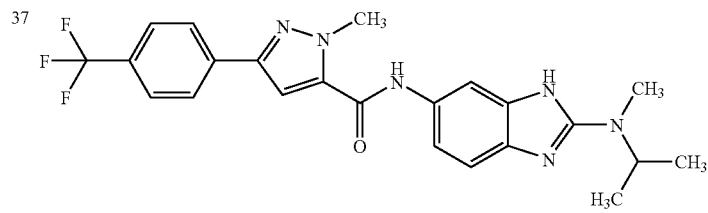 |
| 38 | 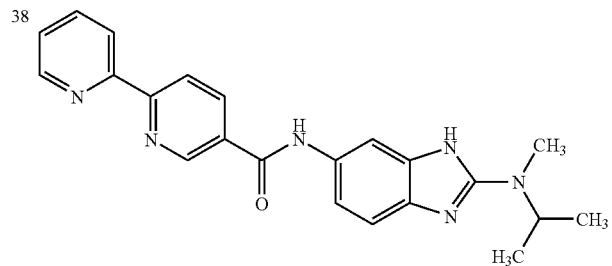 |
| 39 | 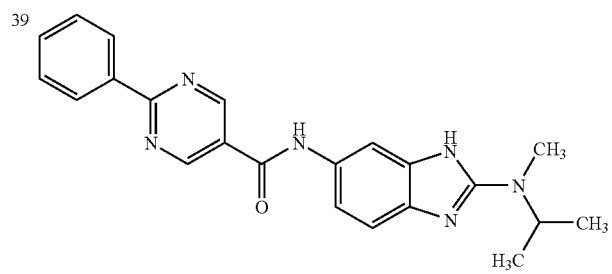 |
| 40 | 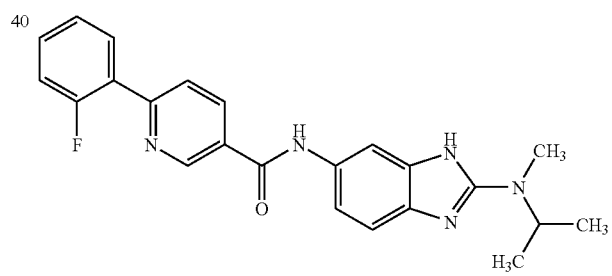 |
| 41 | 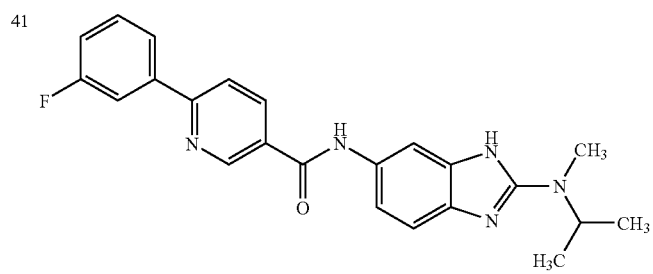 |
| 42 | 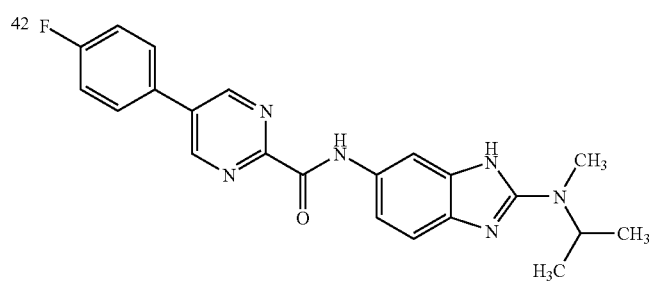 |

| No | Structural Formula |
|---|---|
| 43 | 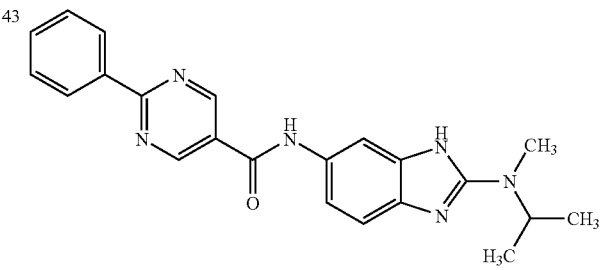 |
| 44 | 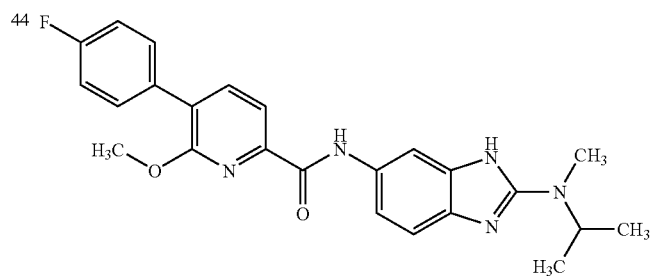 |
| 45 | 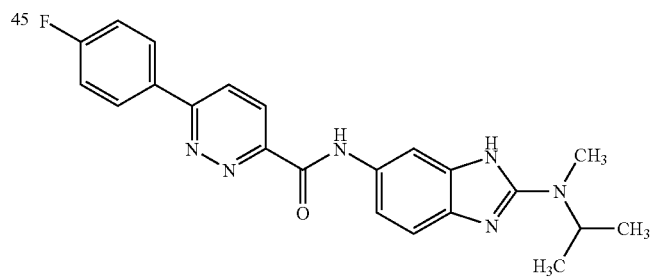 |
| 46 | 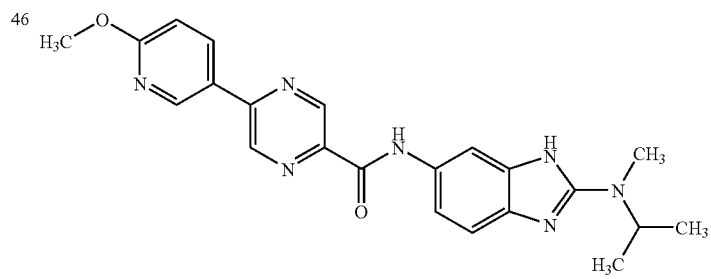 |
| 47 | 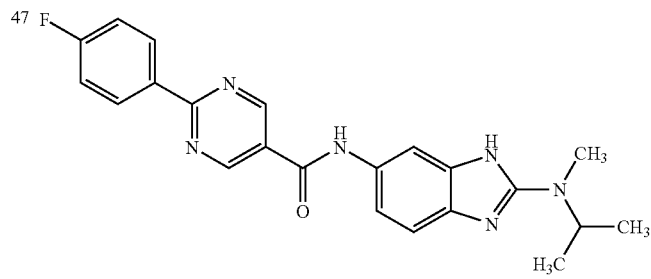 |

-continued
| No | Structural Formula |
|---|---|
| 48 | 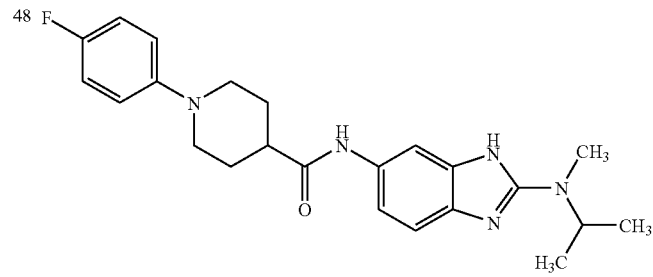 |
| 49 | 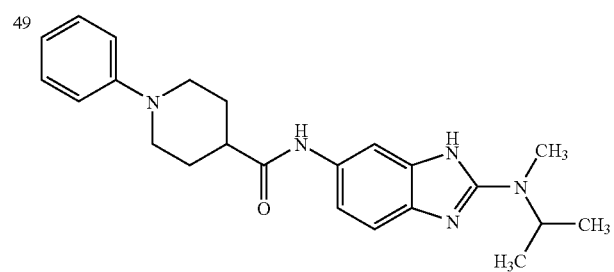 |
| 50 | 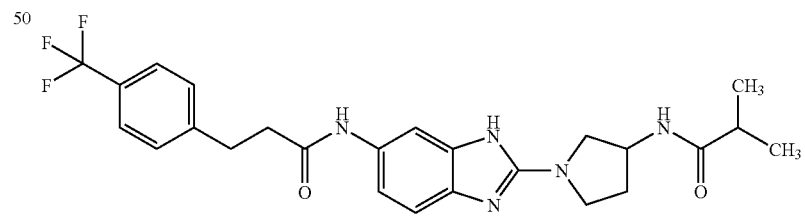 |
| 51 | 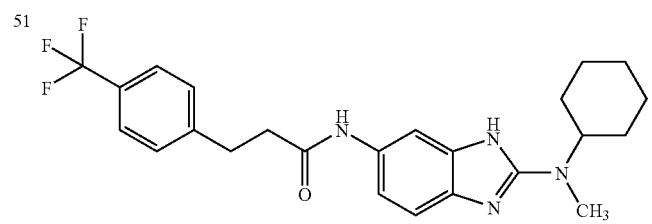 |
| 52 | 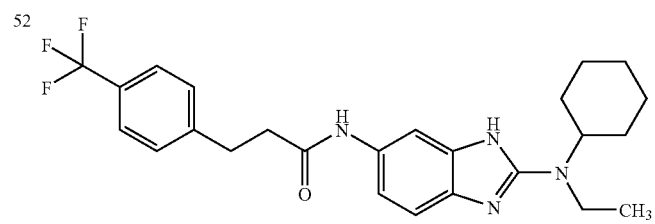 |
| 53 | 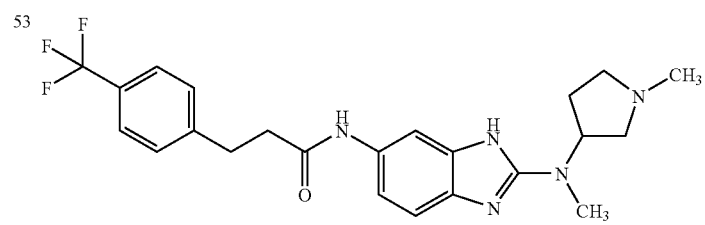 |

-continued
| No | Structural Formula |
|---|---|
| 54 | 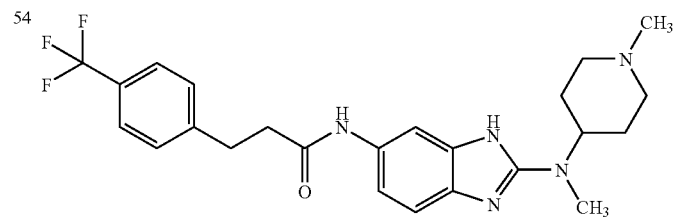 |
| 55 | 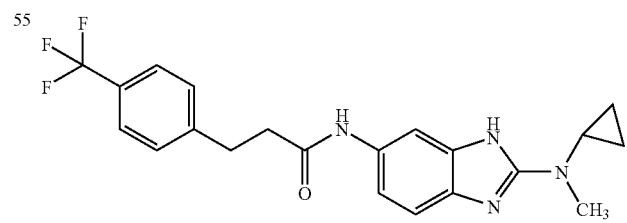 |
| 56 | 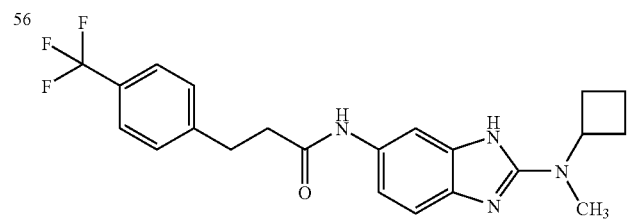 |
| 57 | 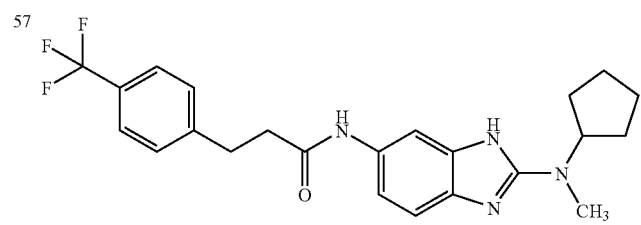 |
| 58 | 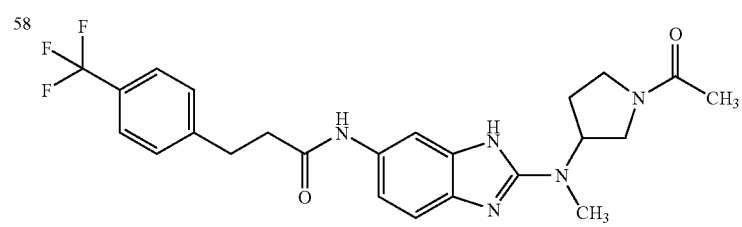 |
| 59 | 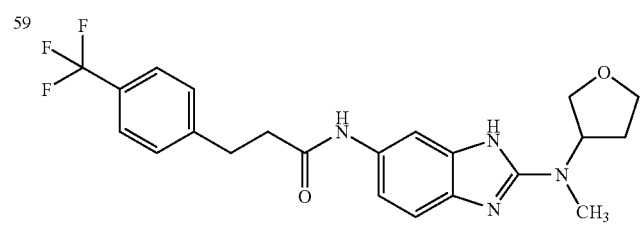 |
| 60 | 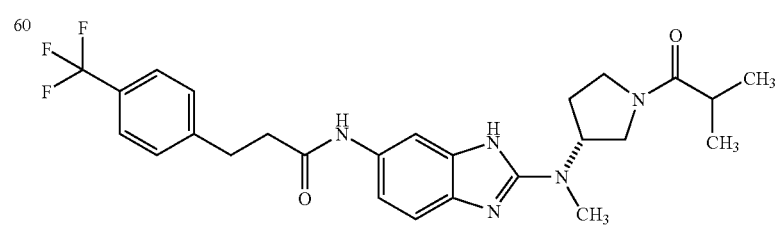 |

-continued
| No | Structural Formula |
|---|---|
| 61 | 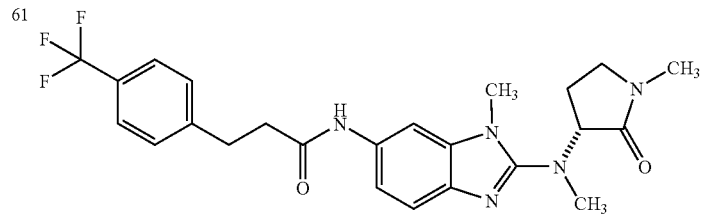 |
| 62 | 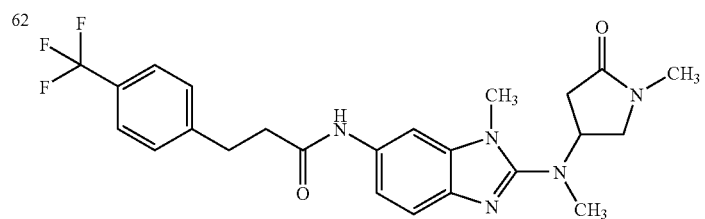 |
| 63 | 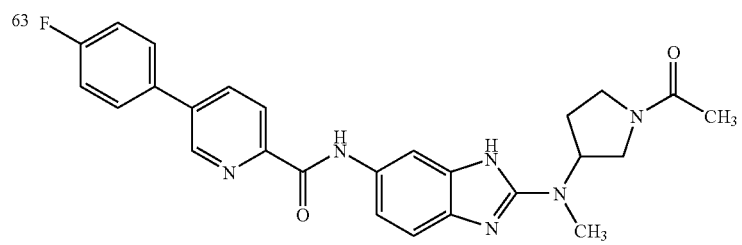 |
| 64 | 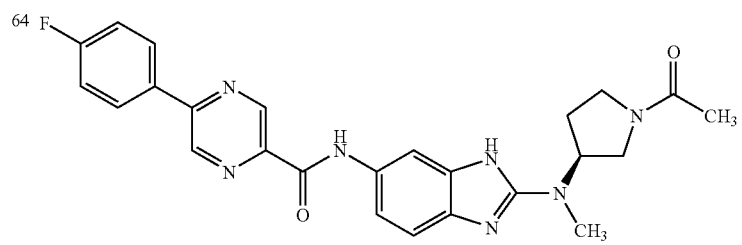 |
| 65 | 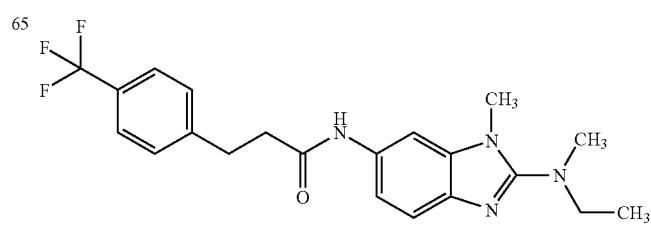 |
| 66 | 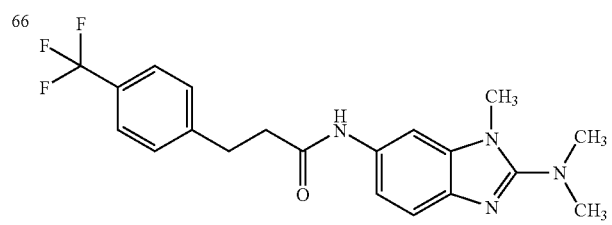 |

| No | Structural Formula |
|----|---|
| 67 | 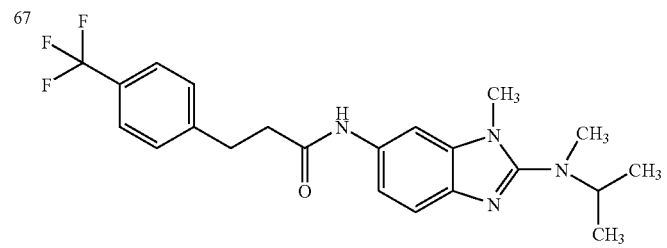 |
| 68 | 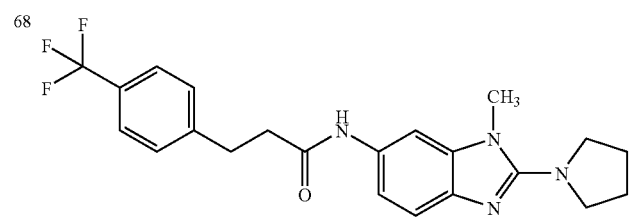 |
| 69 | 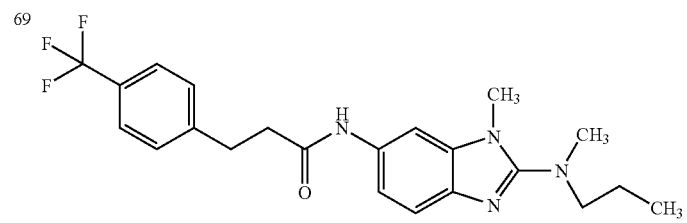 |
| 70 | 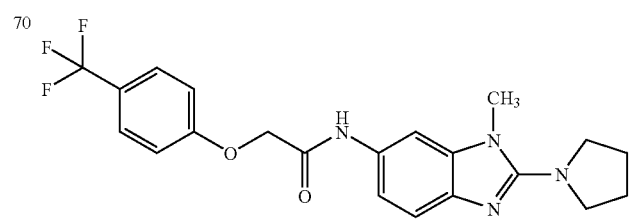 |
| 71 | 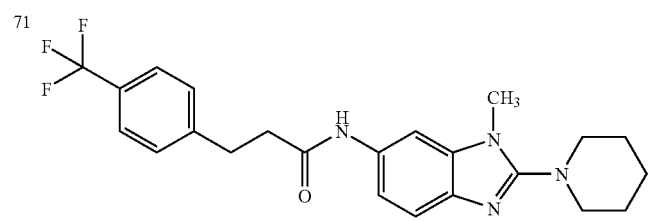 |
| 72 | 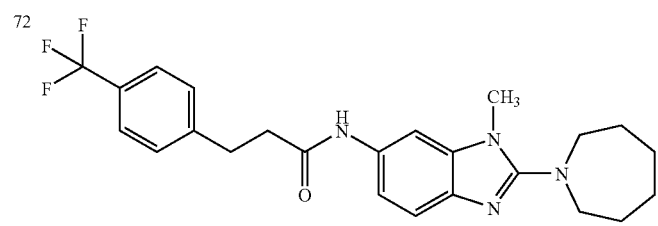 |
| 73 | 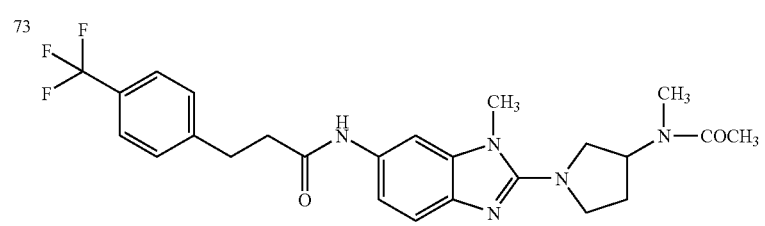 |

-continued
| No | Structural Formula |
|---|---|
| 74 | 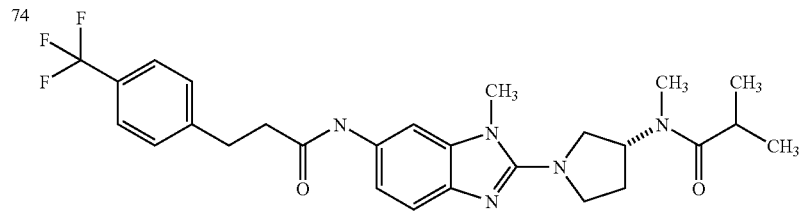 |
| 75 | 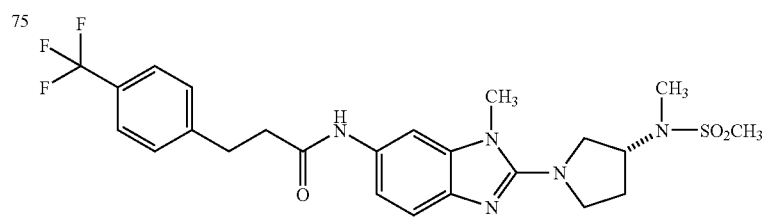 |
| 76 | 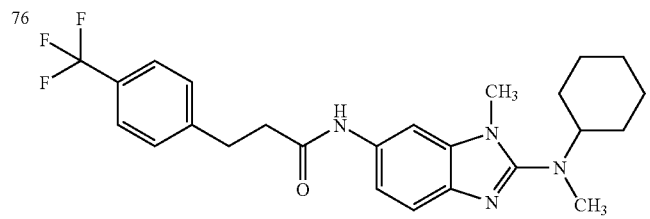 |
| 77 | 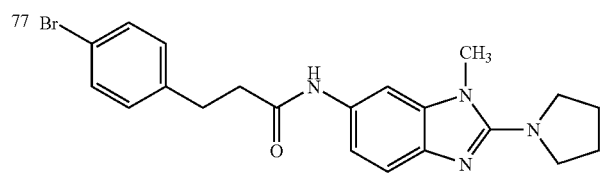 |
| 78 | 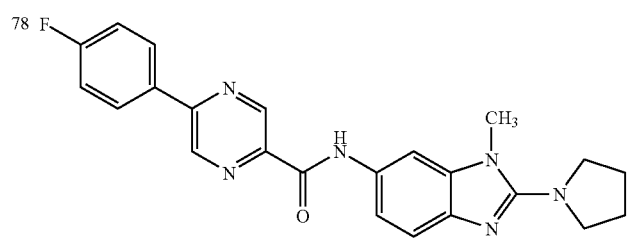 |
| 79 | 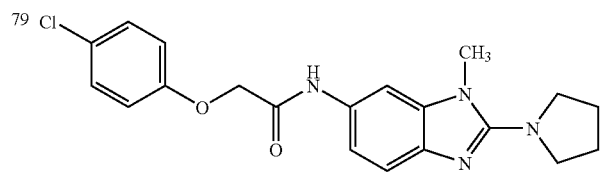 |
| 80 | 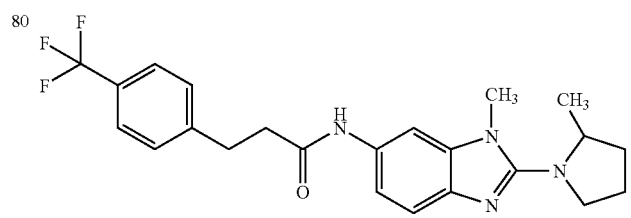 |

| No | Structural Formula |
|----|-------------------|
| 81 | 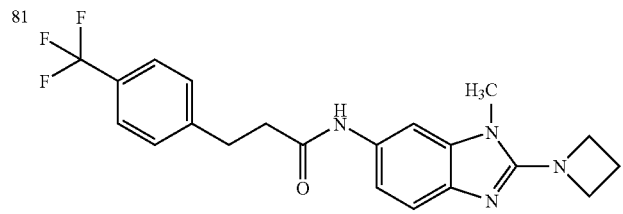 |
| 82 | 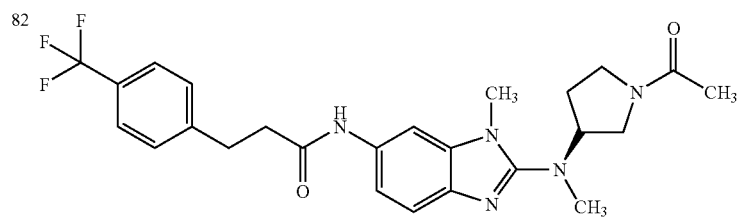 |
| 83 | 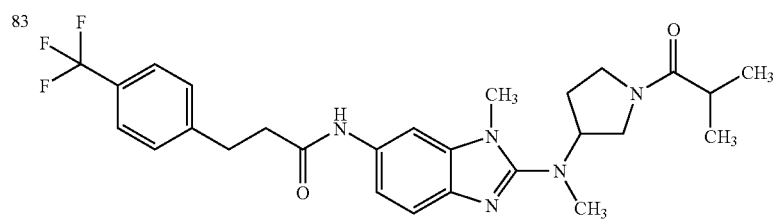 |
| 84 | 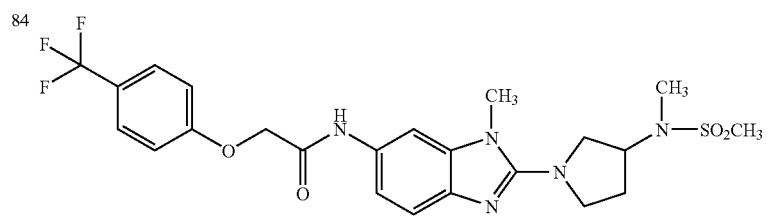 |
| 85 | 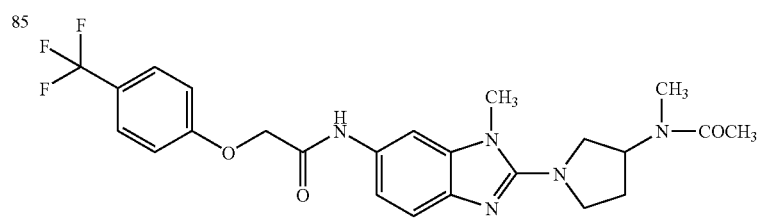 |
| 86 | 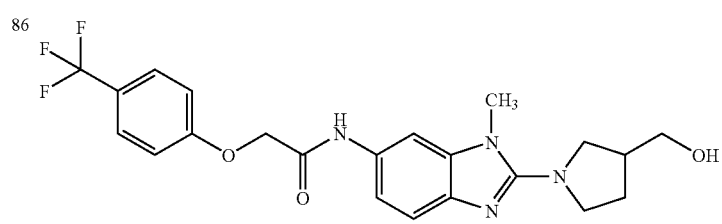 |

| No | Structural Formula |
|---|---|
| 87 | 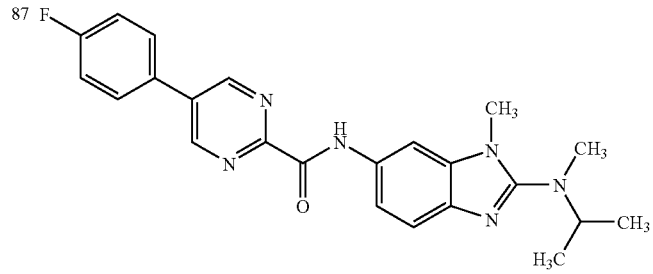 |
| 88 | 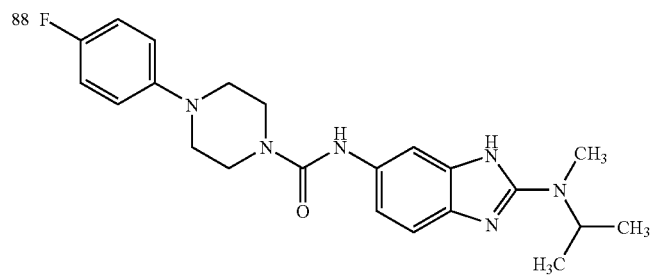 |
| 89 | 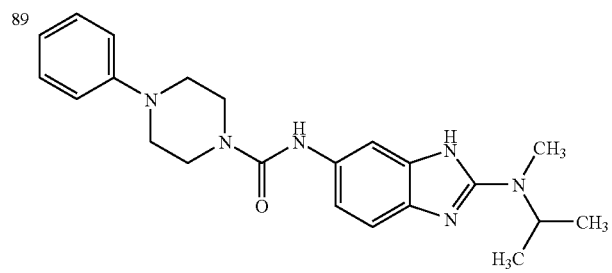 |

Of those compounds, the following are recommended as the particularly preferred:

5-(4-fluorophenyl)-N-{2-[isopropyl(methyl)amino]-1H-benzimidazol-6-yl}-2-pyridinecarboxamide, 5-(4-flurophenyl)-N-{2-[isopropyl(methylamino)-1H-benzimidazol-6-yl}-2-pyrazinecarboxamide, N-{2-[isopropyl(methyl)amino]-1H-benzimidazol-6-yl}-N-methyl-5-[4-(trifluoromethyl)phenyl]-1,2,4-oxadiazole-3-carboxamide, 3-(4-fluorophenyl)-N-{2-[isopropyl(methyl)amino]-1H-benzimidazol-6-yl}-1,2,4-oxadiazole-5-carboxamide, 6-(4-fluorophenyl)-N-{2-[isopropyl(methyl)amino]-1H-benzimidazol-6-yl}-3-pyridinecarboxamide, N-{2-[1-acetyl-3-pyrrolidinyl(methyl)amino]-1-benzimidazol-6-yl}-5-(4-fluorophenyl)-2-pyridinecarboxamide, N-{2-[isopropyl(methyl)amino]-1H-benzimidazol-6-yl}-5-phenyl-2-pyrazinecarboxamide, N-{2-[1-acetyl-3-pyrrolidinyl(methyl)amino]-1H-benzimidazol-6-yl}-5-(4-fluorophenyl)-2-pyrazinecarboxamide, 5-(4-fluorophenyl)-N-{2-[isopropyl(methyl)amino]-1H-benzimidazol-6-yl}-2-pyrimidinecarboxamide, 6-(4-fluorophenyl)-N-{2-[isopropyl(methyl)amino]-1H-benzimidazol-6-yl}-3-pyridazinecarboxamide, 2-(4-fluorophenyl)-N-{2-[isopropyl(methyl)amino]-1H-benzimidazol-6-yl}-5-pyrimidinecarboxamide, N-{2-[isopropyl(methyl)amino]-1H-benzimidazol-6-yl}-3-[4-(trifluoromethyl)phenyl]-1,2,4-oxadiazole-5-carboxamide, N-{2-[isopropyl[(methyl)amino]-1H-benzimidazol-6-yl}-1-[4-(trifluoromethyl)phenyl]-1,2,4-triazole-3-carboxamide, N-{2-[isopropyl(methyl)amino]-1H-benzimidazol-6-yl}-5-[4-(trifluoromethyl)phenyl]-1,3,4-oxadiazole-2-carboxamide, N-{2-[isopropyl(methyl)amino]-1H-benzimidazol-6-yl}-5-methyl-1-[4-(trifluoromethyl)phenyl]-1H-pyrazole-4-carboxamide, N-{2-[isopropyl(methyl)amino]-1H-benzimidazol-6-yl}-2-[4-(trifluoromethyl)phenyl]-2H-tetrazole-2-carboxamide, 6-(3-fluorophenyl)-N-{2-[isopropyl(methyl)amino]-1H-benzimidazol-6-yl}-3-pyridinecarboxamide, N-{2-[isopropyl(methyl)amino]-1H-benzimidazol-6-yl}-5-phenyl-5-pyrimidinecarboxamide 5-(4-fluorophenyl)-N-{2-[isopropyl(methyl)amino]-1-methyl-1H-benzimidazol-6-yl}-2-pyrimidinecarboxamide, and N-{2-[isopropyl(methyl)amino]-1H-benzimidazol-6-yl}-5-phenyl-3-pyridinecarboxamide.

Production Processes of the Compounds Represented by the General Formula [I]

Compounds which are represented by the general formula [I] can be produced, for example, by suitably combining the following production processes.

Production Process 1

Reaction scheme 1

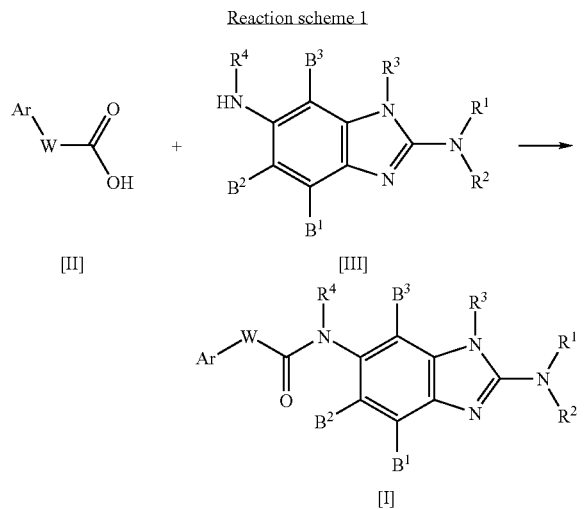

[wherein $B^1$, $B^2$, $B^3$, $R^1$, $R^2$, $R^3$, $R^4$ W and Ar are same to those as previously defined].

This process is one for obtaining a compound represented by the general formula [I] by condensing a compound of the general formula [II] with a compound of the general formula [III] in a solvent. Said condensation reaction can be performed following heretofore known amidation methods used for synthesis of peptides, for example, those described in Fundamentals and Experiments of Peptide Synthesis (Nobuo IZUMIYA, et al, Maruzen Publishing Co., 1983).

This reaction is normally conducted in an inert solvent, examples of which include acetonitrile, methylene chloride, potassium carbonate, sodium hydrogencarbonate and the like, can be used as the base.

Exemplary use rate of such a base normally ranges from 1 mole to a molar excess per mole of a compound of the general formula [III]. Where the base is liquid, it may serve also as the solvent.

Whereas, in the above reaction using any of such a reactive derivatives, a basic catalyst such as dimethylaminopyridine can be used as the catalyst for promoting the reaction. Exemplary use rate of said catalyst ranges from 0.1 to 5 moles, preferably from 0.1 to 0.5 mole, per mole of the reactive derivative.

The reaction temperature for the cases of using such a reactive derivative can normally range, for example, −50 to 100° C., preferably −20 to 50° C. being recommended.

The reaction time for the cases of using such a reactive derivative can normally range, for example, from 5 minutes to 7 days, preferably from 30 minutes to 24 hours being recommended.

As those compounds represented by the general formula [II], commercially available compounds can be used, while they can also be prepared following those methods described in Synlett, Vol. 6, 829 (2000); Journal of Medicinal Chemistry, Vol. 41, 1855(1998); ibid, Vol. 44, 703(2001); Heterocycles, Vol. 35, 1551(1994); Synthesis, 609 (1975); and Journal of Heterocyclic Chemistry, Vol. 32, 1563(1995).

Those compounds represented by the general formula [III] can be prepared by the following process.

Production Process 2

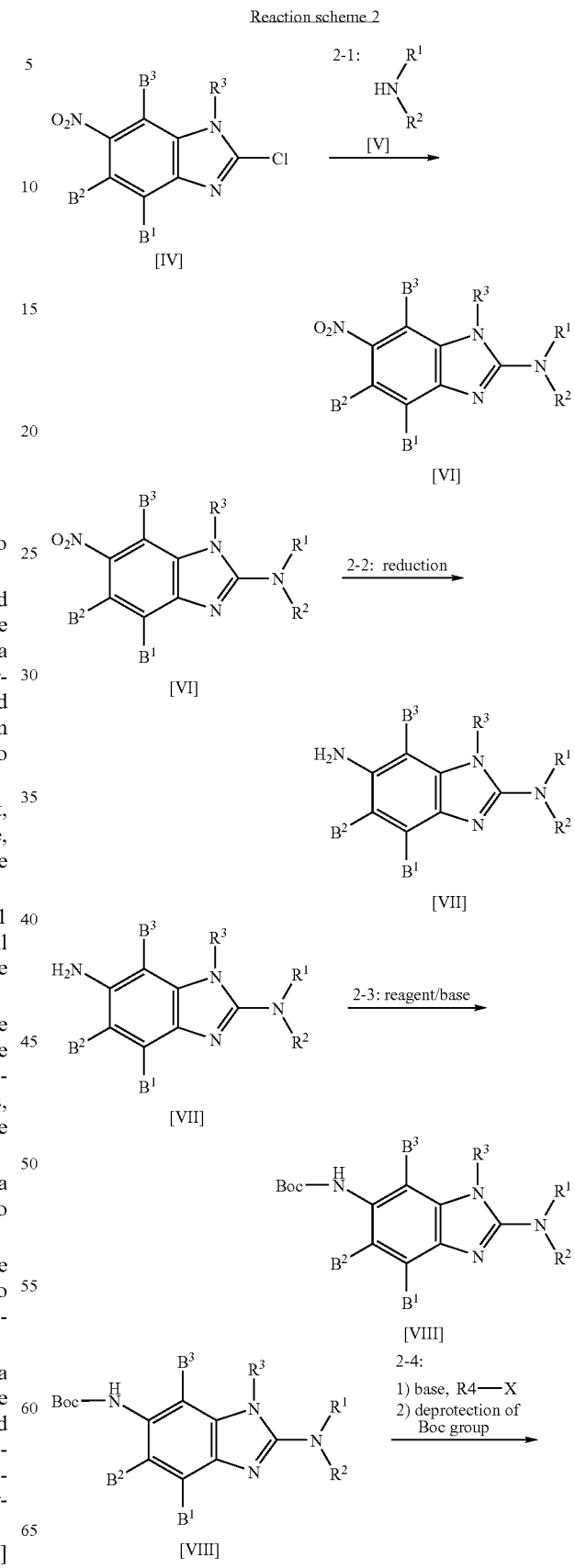

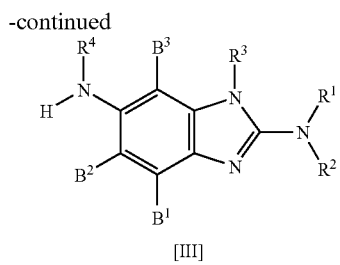

[III]

[wherein X stands for a leaving group such as halogen, for example, chlorine, bromine, iodine and the like, p-toluenesulfoxy, benzenesulfoxy, methanesulfoxy and the like;

$B^1$, $B^2$, $B^3$, $R^1$, $R^2$, and $R^3$ are the same to those as previously defined].

Step 2-1:

Upon heating a compound of the general formula [IV] and a tribromide, oxaryl chloride, phosgene and the like can be named.

A mixed acid anhydride of a compound of the general formula [II] can be obtained by reacting a compound of the general formula [II], for example, with an alkyl chlorocarbonate such as ethyl chlorocarbonate, isobutyl chlorocarbonate or the like; an aliphatic carboxylic acid chloride such as pivaloyl chloride or the like in the presence of an amine such as triethylamine, following the method known per se.

An active ester of a compound of the general formula [II] can be obtained, for example, by reacting a compound of the general formula [II] with N-hydroxy compound such as N-hydroxysuccinimide, N-hydroxyphthalimide, 1-hydroxybenzotriazole (HOBt); phenolic compound such as 4-nitrophenol, 2,4-dinitrophenol, 2,4,5-trichlorophenol, pentachlorophenol, and the like, in the presence of a condensing agent such as N,N'-dicyclohexylcarbodiimide, 1-(3-dimethylaminopropyl)-3-ethylcarbodiimide or the like, following the method known per se.

An active amide of a compound of the general formula [II] can be obtained by reacting a compound of the general formula [II] with, for example, 1,1'-carbonyldiimidazole, 1,1'-carbonylbis(2-methylimidazole) or the like, following the method known per se.

Exemplary use rate of such a reactive derivative of a compound of the general formula [II] normally ranges from 0.5 mole to a molar excess, preferably from 1 mole to 1.5 moles, per mole of the compound of the general formula [III].

The reaction is normally conducted in an inert solvent, examples of the solvent including acetonitrile, methylene chloride, chloroform, THF, DMF, pyridine and mixed solvents of the foregoing.

The reaction progresses even in the absence of a base, while the presence of a base is preferred for smooth progress of the reaction.

Particularly in the reaction using said acid halide or mixed acid anhydride, for example, organic base such as triethylamine, diisopropylethylamine, pyridine and the like, or inorganic base such as sodium hydroxide, potassium hydroxide, sodium carbonate, chloroform, tetrahydrofuran (THF), 1,4-dioxane (dioxane), dimethylformamide (DMF), pyridine and their mixed solvents.

It is preferred to conduct the reaction in the presence of a condensing agent, examples of said condensing agent including N,N'-dicyclohexylcarbodiimide, 2-chloro-1,3-dimethyl-2-imidazolium chloride, N,N'-diisopropylcarbodiimide, 1-(3-dimethylaminopropyl)-3-ethylcarbodiimide, 1-(3-dimethylaminopropyl)-3-ethylcarbodiimide hydrochloride (WSC.HCl), benztriazol-1-yloxy-tris-(dimethylamino)phosphonium hexafluorophosphate, benztriazol-1-yloxy-tris-pyrrolidino-phosphonium hexafluorophosphate, bromotris-(dimethylamino)-phosphonium hexafluorophosphate, diphenyl phosphorazidate, 1,1'-carbonyldiimidazole and the like.

Exemplary use rate of such a condensing agent normally ranges from 1 mole to a molar excess, preferably 1 to 1.5 moles, per mole of a compound of the general formula [II].

Exemplary reaction temperature normally ranges from −50° C. to 100° C., preferably from −20° C. to 50° C. being recommended.

Exemplary reaction time normally ranges from 30 minutes to 7 days, preferably from 1 to 24 hours being recommended.

A compound of the general formula [I] can be prepared through the reaction of a reactive derivative of a carboxylic acid of the general formula [II] instead of the carboxylic acid itself, with a compound of the general formula [III].

As said reactive derivatives of those carboxylic acids which are represented by the general formula [II], for example, acid halides, mixed acid anhydrides, active esters, active amides and the like can be used. These reactive derivatives can be readily produced upon referring to aforesaid Fundamentals and Experiments of Peptide Synthesis (Nobuo IZUMIYA, Maruzen Publishing Co., 1983).

An acid halide of a compound of the general formula [II] can be obtained by reacting a compound of the general formula [II] with a halogenating agent following the method known per se. As examples of the halogenating agent, thionyl chloride, phosphorus trichloride, phosphorus pentachloride, phosphorus oxychloride, phosphorus compound of the general formula [V] in the presence or absence, preferably presence, of an inert solvent, at 20° C.-200° C., preferably 50° C.-150° C., for 10 minutes-48 hours, preferably 1-24 hours, a compound represented by the general formula [VI] is obtained. This reaction can be conducted in a sealed tube.

As the inert solvent, for example, dioxane, THF, acetonitrile, DMF, dimethylsulfoxide (DMSO), acetone and the like can be used, preferably dioxane, DMF and DMSO being recommended.

Exemplary use rate of a compound of the general formula [V] ranges from 1 to 50 moles, preferably from 2 to 10 moles, per mole of a compound of the general formula [IV].

Then the compound of the general formula [VI] is isolated from the reaction mixture containing the compound of the general formula [VI] and purified, by the means heretofore known, and is subjected to the next step. While the intervening isolation and purification are not indispensable, it is preferred to conduct these operations. Means for the isolation and purification herein include, for example, solvent extraction, recrystallization, column chromatography, liquid chromatography, fractionating thin-layer chromatography (preparative TLC), similar to those which are applicable also in the subsequent steps.

Step 2-2

The nitro group of the compound of the general formula [VI] is reduced to convert the compound to the one represented by the general formula [VII]. As the reduction means, for example, the method as described in WO 02/40019 Pamphlet can be used. Where $R^4$=H in the compound represented by the general formula [III], it becomes the compound represented by the general formula [VII].

Step 2-3

The compound of the general formula [VII] is Boc-protected by a known method to convert it to the one represented by the general formula [VIII]. Boc-protection can be conducted in the presence of a base, using, for example, triethylamine, diisopropylethylamine, pyridine or the like. Also as Boc-reagent, commercial reagents can be used, examples of which include (Boc)2O, N-t-butoxycarbonyloxyimino-2-phenylacetonitrile, t-butyl-N-succimidyl carbamate and the like.

Exemplary use rate of Boc reagent ranges from 1 to 5 moles, preferably from 1 to 1.5 moles, per mole of the compound of the general formula [VII]. Also the use rate of the base can range from 0.5 to 5 moles, preferably from 1 to 3 moles, per mole of the compound of the general formula [VII].

The reaction is normally conducted in a solvent, examples of which include acetonitrile, methylene chloride, chloroform, THF, DMF, pyridine and the like, or their mixed solvents.

Step 2-4

The compound of the general formula [VIII] then is mixed with a base such as NaH, to provide a reaction mixture which is further reacted with $R^4$—X, and thereafter the Boc group is deprotected, to provide a compound represented by the general formula [III].

Specifically, a compound of the general formula [VIII] and base are reacted in an inert solvent at 0° C. for 1-30 minutes. $R^4$—X is added to the resultant reaction mixture and reacted further at 0° C.-50° C. for 30 minutes-12 hours to introduce $R^4$ into the compound.

Exemplary use rate of the base may range 1-10 moles, preferably 1-3 moles, per mole of the compound of the formula of the general formula [VIII]. Also as the use rate of $R^4$—X, it may range 1-10 moles, preferably 1-3 moles, per mol of the compound of the general formula [VIII].

As $R^4$—X, for example, methyl iodide, ethyl iodide, methyl p-toluenesulfonate and the like can be named.

As the inert solvent, for example, diethyl ether, THF, DMF and the like can be named.

Also the deprotection of Boc group can be conducted by heretofore known means. For example, deprotection with trifluoroacetic acid, that with hydrochloric acid or the like can be carried out (Protective Groups in Organic Synthesis as later referred to may be conferred).

Furthermore, as those compounds, represented by the general formula [IV] and/or those represented by the general formula [V], commercial reagents may be used, or they can be readily prepared by heretofore known methods, methods described in working Examples given in this specification, or combinations thereof.

Production Process 3

Production process 3 is useful when W is a 3-8 membered aliphatic nitrogen-containing heterocyclic group.

Reaction scheme 3

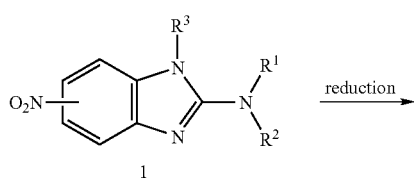

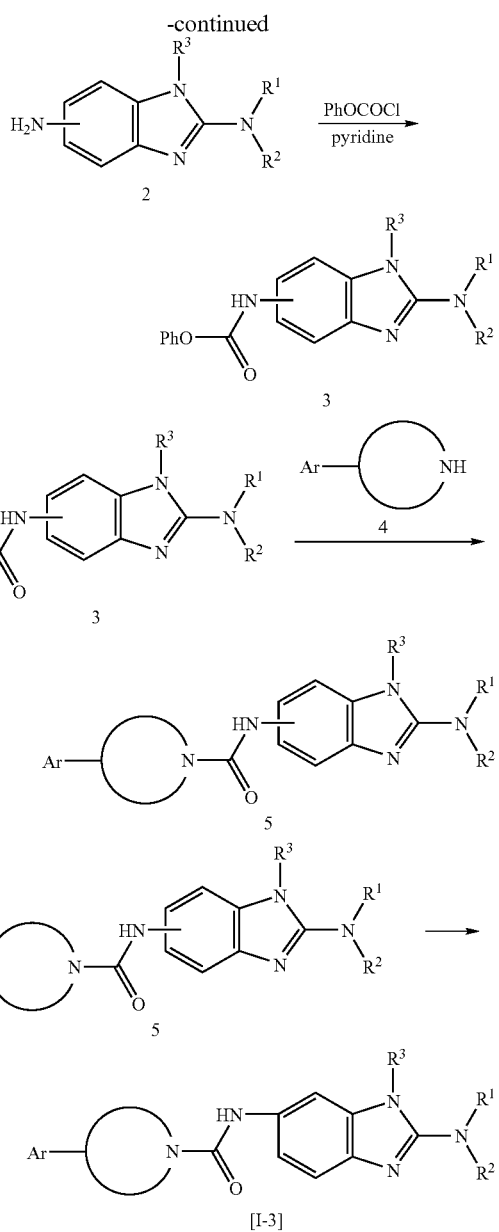

[in which

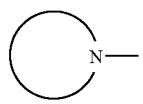

stands for a 3-8 membered aliphatic nitrogen-containing heterocycle as W in the general formula [I]; Ph stands for phenyl; and $R^1$, $R^2$, $R^3$ and Ar are the same to those as previously defined].

Compound 1 corresponding to a compound of the general formula [VI] is reduced to Compound 2 following the Step 2-2. Then said Compound 2 is phenylcarbamated with phenylchloroformate in pyridine, to provide Compound 3. Said Compound 3 is condensed with Compound 4 to provide Compound 5. For conversion of Compound 3 to Compound 5, for example, the method as described in WO 0114376 Pamphlet can be referred to. Thus obtained Compound 5 can provide the compound represented by the general formula [I-3], as separated by means of column chromatography or the like, where necessary. As Compound 4, commercial reagent can be used, or it can be prepared following the methods as described in Journal of Medicinal Chemistry, Vol. 43, 2703, (2000); Tetrahedron Letters, Vol. 38, 6359(1997); and Ibid., Vol. 39, 617(1998).

In each of the reactions adopted for above Production Processes 1-3, when such groups as amino, hydroxyl, carboxyl, oxo, carbonyl and the like which do not participate in the reaction are present in the reactant(s), they can be suitably protected with protective groups of amino, hydroxyl, carboxyl, oxo or carbonyl, respectively, before carrying out the reactions. After each of the reactions, the protective groups can be removed.

As "amino-protective group" aralkyl such as benzyl, p-methoxybenzyl, 3,4-dimethoxybenzyl, o-nitrobenzyl, p-nitrobenzyl, benzhydril, trityl and the like; lower alkanoyl such as formyl, acetyl, propionyl, butyryl, pivaloyl and the like; benzoyl; arylalkanoyl such as phenylacetyl, phenoxyacetyl and the like; lower alkoxycarbonyl such as methoxycarbonyl, ethoxycarbonyl, propyloxycarbonyl, tert-butoxycarbonyl and the like; aralkyloxycarbonyl such as benzyloxycarbonyl, p-nitrobenzyloxycarbonyl, phenethyloxycarbonyl and the like; lower alkylsilyl such as trimethylsilyl, tert-butyldimethylsilyl and the like can be named, in particular, acetyl, pivaloyl, benzoyl, ethoxycarbonyl, tert-butoxycarbonyl and the like being recommended.

As "hydroxyl-protective group", for example, lower alkyl such as methyl, ethyl, propyl, isopropyl, tert-butyl and the like; lower alkylsilyl such as trimethylsilyl, tert-butyldimethylsilyl and the like; lower alkoxymethyl such as methoxymethyl, 2-methoxyethoxymethyl and the like; tetrahydropyranyl; trimethylsilylethoxymethyl; aralkyl such as benzyl, p-methoxybenzyl, 2,3-dimethoxybenzyl, o-nitrobenzyl, p-nitrobenzyl, trityl and the like; and acyl such as formyl, acetyl and the like can be named. In particular, methyl, methoxymethyl, tetrahydropyranyl, trityl, trimethylsilylethoxymethyl, tert-butyldimethylsilyl and acetyl are recommended.

As "carboxyl-protective group", for example, lower alkyl such as methyl, ethyl, propyl, isopropyl, tert-butyl and the like; lower haloalkyl such as 2,2,2-trichloroethyl and the like; lower alkenyl such as 2-propenyl; and aralkyl such as benzyl, p-methoxybenzyl, p-nitrobenzyl, benzhydryl, trityl and the like can be named. In particular, methyl, ethyl, tert-butyl, 2-propenyl, benzyl, p-methoxybenzyl and benzhydryl are recommended.

As "oxo- or carbonyl-protective groups", acetals and ketals such as ethyleneketal, trimethyleneketal, dimethylketal and the like can be named.

Means for removing protective groups differ depending on kind of the protective groups and stability of individual compounds represented by the general formula [I]. For example, the removal is conducted following those methods described in literature [cf. Protective Groups in Organic Synthesis, T. W. Greene, John Wiley & Sons Co., (1981)] or those analogous thereto, by solvolysis using acid or base, i.e., a method of having, for example, from 0.01 mole to a large molar excess of acid, preferably trifluoroacetic acid, formic acid, hydrochloric acid or the like; or from equimolar to a large molar excess of base, preferably potassium hydroxide, calcium hydroxide or the like, act on the object compound; chemical reduction using hydrogenated metal complex or by catalytic reduction using palladium-carbon catalyst or Raney nickel catalyst.

Compounds of the general formula [I] which are obtained by the foregoing methods can be easily isolated and purified by heretofore known separation means. As such means, for example, solvent extraction, recrystallization, column chromatography, liquid chromatography, preparative chromatography and the like can be named.

Compounds of the present invention may have stereoisomers or tautomers such as optical isomers, diastereoisomers, geometrical isomers or the like, depending on the form of their substituents, all of these stereoisomers, tautomers and their mixtures being encompassed by the compounds of the present invention.

Pharmaceutical Compositions Containing the Compounds Which are Represented by the General Formula [I-1]

Those compounds of the present invention can be administered orally or parenterally, and when formulated into preparation forms adapted for administration, can provide preventing or treating agents for metabolic disorders represented by obesity, diabetes, hormone disorder, hyperlipidemia, gout, fatty liver, hepatitis and cirrhosis; cardiovascular disorders represented by stenocardia, acute or congestive heart failure, myocardial infarction, coronary atherosclerosis, hypertension, renal diseases and electrolyte abnormality; central nervous system or peripheral nervous system disorders represented by bulimia, emotional disturbance, depression, anxiety, epilepsy, delirium, dementia, schizopherenia, attention-deficit hyperactivity disorder, memory impairment, sleep disorders, cognitive failure, dyskinesia, paresthesias, smell disorders, morphine tolerance, drug dependence and alcoholism; reproductive disorders represented by infertility, preterm labor and sexual dysfunction; digestive disorders; respiratory disorders; cancer or pigmentation: in particular, preventing or treating agents for obesity.

In the occasions of clinical use of the compounds of the present invention, the compounds may be formulated into various forms of preparation with addition of pharmaceutically acceptable carriers according to the mode of administration, and thereafter administered. As carriers in such occasions, various additives heretofore known in the field of medical preparations can be used, examples of which include gelatine, lactose, sucrose, titanium dioxide, starch, crystalline cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light silicic anhydride, talc, vegetable oil, benzyl alcohol, gum arabic, propylene glycol, polyalkylene glycol, cyclodextrin or hydroxypropylcyclodextrin and the like.

As the preparation forms formulated as mixtures of these carriers and the compounds of the present invention, for example, solid preparations such as tablet, capsule, granule, powder or suppository; and liquid preparations such as syrup, elixir, or injection and the like can be named, which can be prepared following heretofore known methods in the field of medical preparations. Furthermore, liquid preparations may take such a form as to be dissolved or suspended in water or in other suitable medium immediately before use. Particularly, injections can be dissolved or suspended in physiological saline solution or glucose solution where necessary, and buffer or preservative may further be added thereto.

Those preparations can contain the compounds of the present invention at a rate of 1.0-100% by weight, preferably 1.0-60% by weight, to the whole of individual pharmaceutical preparation; and 0-99.0% by weight, preferably 40-99.0% by weight, of pharmaceutically acceptable carrier. These preparations may also contain therapeutically active other compound(s), for example, treating agents for diabetes, hypertension, arterial sclerosis and the like.

In case of using the compounds of the present invention as preventing or treating agents of said diseases or sicknesses, their dosages and administration frequency differ depending on sexuality, age, body weight and seriousness of symptoms of individual patients and the kind and scope of intended therapeutic effect. Whereas, generally for oral administration, it is preferred to administer 0.01-20 mg/kg per day per adult patient, as a single dose or several divided doses. For parenteral administration preferably 0.002-10 mg/kg is administered as a single does or several divided doses. Depending on symptoms, preventive administration is permissible.

Combination Therapy

The compounds of the present invention can be used in combination with drugs effective for hypertension, obesity-associated hypertension, hypertension-associated diseases, cardiac hypertrophy, left ventricular hypertrophy, metabolic disorder, obesity, obesity-associated diseases and the like (hereafter referred to as "drug for combined use"). Such drugs can be administered simultaneously, separately or in succession, for prevention or treatment of above-named diseases. When a compound of the present invention is used simultaneously with one, two or more of drugs for combined use, they may be formulated into a medical preparation suited for single administration form. Whereas, for occasions of combination therapy, a composition containing the compound of the present invention and drug(s) for combined use may be administered to the object of medication in different packages, either simultaneously, separately or successively. They may be administered at time interval(s).

Dose(s) of drug(s) for combined use are determinable following clinically adopted dose(s), which can be suitably selected according to individual object of medication, administration route, specific disease, combination of drugs, and the like. Form of administering drug(s) for combined use is not critical but it is sufficient that the compound of the present invention is combined with selected drug(s) for combined use at the time of administration. As adoptable administration forms, for example, 1) administration of single preparation obtained by simultaneously formulating a compound of the present invention and drug(s) for combined use, 2) simultaneous administration of two kinds of preparations obtained by separately formulating a compound of the present invention and drug(s) for combined use, via a same administration route, 3) administration at a certain time interval, via a same administration route, of two kinds of preparations obtained by separately formulating a compound of the present invention and drug(s) for combined use, 4) simultaneous administration of two kinds of preparations obtained by separately formulating a compound of the present invention and drug(s) for combined use, via different administration routes, and 5) administration of two kinds preparations obtained by separately formulating the compound of the present invention and drug(s) for combined use, different administration routes, at a certain time interval (e.g., administration by the order of the compound of the present invention and then the drug(s) for combined use, or by the reversed order) can be adopted. The blend ratio of a compound of the present invention and drug(s) for combined use can be suitably selected, according to individual object of medication, administration route, disease and the like.

As drugs for combined use which can be used in the present invention, for example, those for treating diabetes, hyperlipidemia, hypertension, obesity and the like can be named. Two or more of such drugs for combined use may be combined at an adequate ratio and used.

As drug for treating diabetes, for example, 1) PPAR γ agonists such as glitazones [e.g., ciglitazone, darglitazone, englitazone, isoglitazone (MCC-555) and the like], pioglitazone, rosiglitazone, troglitazone, BRL49653, CLX-0921, 5-BTZD, GW-0207, LG-100641, LY-300512 and the like; 2) biganides such as metformin, buformin, phenformin and the like; 3) protein tyrosine phosphatase-1B inhibitor; 4) sulfonylureas such as acetohexamide, chloropropamide, diabinese, glibenclamide, glipizide, glyburide, glimepiride, gliclazide, glipentide, gliquidone, glisolamide, tolazamide, tolbutamide and the like; 5) meglitinides such as repaglinide, nateglinide and the like; 6) α-glucosidohydroxylase inhibitors such as acarbose, adiposine, camiglibose, emiglitate, miglitol, voglibose, pradimicin-Q, salbostatin, CKD-711, MDL-25,673, MDL-73,945, MOR 14 and the like; 7) α-amylase inhibitors such as tendamistat, trestatin, A1 3688 and the like; 8) insulin secretion promoters such as linogliride, A-4166 and the like; 9) fatty acid oxidation repressors such as clomoxir, etomoxir and the like; 10) A2 antagonists such as midaglizole, isoglidole, deriglidole, idozoxan, earoxan, fluparoxan and the like; 11) insulin or insulin mimetics such as biota, LP-100, novarapid, insulin detemir, insulini lispro, insulin glargine, insulin zinc, Lys-Pro-insulin, GLP-[(73-7), GLP 1 amide (7-36) and the like; 12) non-thiazolidindione such as JT-501, farglitazar and the like; and 13) PPARα/γdual agonists such as MK-0767, CLX-0940, GW-1536, GW-1929, GW-2433, KRP-297, L-796449, LR-90 and SB219994 and the like; can be named.

As said treating agent for hyperlipidermia, for example, 1) cholic acid absorbefacients such as colestrylamine, colesevelem, colestipol, dialkylaminoalkyl derivatives of crossdextran, Colestid™, LoCholest™, Ovestra™ and the like; 2) HMG-CoA reductase inhibitors such as atorvastatin, itavastatin, fluvastatin, lovastatin, pravastatin, rivastatin, rosuvastatin, simvastatin, ZD-4522 and the like; 3)HMG-CoA synthesis inhibitors; 4) cholesterol absorption inhibitors such as snatol ester, β-sitosterol, sterol gluoside, ezetimibe and the like; 5) acyl coenzyme A cholesterol acyl transferase inhibitors such as avasimibe, eflucimibe, KY-505, SMP-709 and the like; 6) CETP inhibitors such as JTT 705, torcetrapib, CP532632, BAY-63-2149, SC-591, SC-795 and the like; 7) squalene synthesis inhibitors; 8) antioxidants such as probucol; 9) PPARα agonists such as beclofibrate, benzafibrate, ciprofibrate, clofibrate, ethofibrate, fenofibrate, gemcabene, gemfibrozil, GW-7647, BM-170744, LY-518674, fibric acid derivatives [e.g., Atromid™, Lopid™, Tricor™ and the like; 10) FXR receptor antagonists such as GW-4064, SR-103912 and the like; 11) LXR receptor agonists such as GW3965, T9013137, XTCO-179628 and the like; 12) lipoprotein synthesis inhibitors such as niacin; 13) renin-angiotensin inhibitors; 14) microsome-triglyceride transport inhibitors; 15) cholic acid resorption inhibitors such as BARA 1453, SC435, PHA384640, S-435, AZD7706 and the like; 16) PPAR δ agonists such as GW501516, GW590735 and the like; 17) triglyceride synthesis inhibitors; 18) MTTP inhibitors such as LAB687, CP346086 and the like; 19) low density lipoprotein receptor inducer; 20) squalene epoxidase inhibitors; 21)thrombocyte agglutination inhibitors; and 22) 5-lipoxygenase-activating protein inhibitors; can be named.

As said treating agents for hypertension, for example, 1) diuretic such as thiazide-type diuretic, e.g., chlorothialidon, chlorothiazide, dichlorophenamide, hydrofluorothiazide, indapamide, hydrochlorothiazide and the like; loop-type diuretic, e.g., bumetanide, ethacrynic acid, furosemide, torsemide and the like; sodium-type diuretic such as amiloride, triamterene and the like; and aldosterone antagonist-type diuretic, e.g., spironolactone, epirenone and the like; 2) β-adrenaline blockers such as acebutolol, atenolol, betaxolol, bevantolol, bisoprolol, bopindolol, carteolol, carvedilol, celiprolol, esmolol, indenolol, metaproplol, nadolol, nebivolol, penbutolol, pindolol, propanolol, sotalol, tertatolol, tilisolol, timolol and the like; 3) calcium channel blockers such as amlodipine, aranidipine, azelnidipine, barnidipine, benidipine, hepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine nitrendipine, manidipine, pranidipine, verapamil and the like; 4) angiotensin alteration enzyme inhibitors such as benazepril, captopril, cilazapril, delapril, enalapril, fosinopril, imidapril, losinopril, moexipril quinapril, quinaprilat, ramipril, perindopril, perindropril, quanipril, spirapril, tenocapril, trandolapril, zofenopril and the like; 5) neutral endopeptidase inhibitors such as omapatrilat, cadoxatril, ecadotril, fosidotril, sampatrilat, AVE 7688, ER 4030 and the like; 6) endothelin antagonists such as tezosentan, A308165, YM62899 and the like; 7) vasodilators such as hydrazine, clonidine, minoxidil, nicotinyl alcohol and the like; 8) angiotension II antagonists such as candesartan, eprosartan, irbesartan, losartan, pratosartan, tasosartan, telmisartan, valsartan, EXP-3137, FI6828K, RNH6270 and the like; 9) α/β adrenaline blockers such as nipradilol, arotinolol, amosulalol and the like; 10) α1 blockers such as terazosin, urapidil, prazosin, bunazosin, trimazosin, doxazosin, naftopidil, indoramin, WHIP164, XEN010 and the like; 11) α2 agonists such as lofexidine, tiamenidine, moxonidine, rilmenidine, guanobenz and the like; and 12) aldosteron inhibitors can be named.

As said anti-obesity agents, for example, 1) 5HT (serotonin) transporter inhibitors such as paroxetine, fluoxetine, fenfluramine, fluvoxamine, sertraline, imipramine and the like; 2) norepinephrine transporter inhibitors such as GW320659, desipramine, talsupram, nomifensine and the like; 3) cannabinoid 1 receptor 1(CB-1) antagonist/inverse agonist such as rimonabant (Sanofi Synthelabo), SR-147778 (Sanofi Synthelabo), BAY-65-2520 (Bayer), SLV-319 (Sorbay) and those compounds disclosed in U.S. Pat. Nos. 5,532,237, 4,973,587, 5,013,837, 5,081,122, 5,112,820, 5,292,736, 5,624,941, 6,028,084, WO96/33159, WO98/33765, WO98/43636, WO98/43635, WO01/09120, WO01/96330, WO98/31227, WO98/41519, WO98/37061, WO00/10967, WO0/10968, WO97/29079, WO99/02499, WO01/58869, WO02/076949, WO01/64632, WO01/64633, WO01/64634, WO03/006007, WO03/007887 and EP-658546, and the like; 4) ghrelin antagonists such as those compounds disclosed in, e.g., WO01/87355 and WO02/08250; 5) histamine (H3) antagonist/inverse agonist such as thioperamide, 3-(1H imidazol-4-yl) propyl N-(pentenyl) carbonate, clobenpropit, iodophenpropit, imoproxifan, GT2395, A331440, compounds disclosed in WO02/15905, 0-[3-(1H-imidazo-4-yl)propanol] carbamate, piperazin-containing H3 receptor antagonist (Lazewska, D. et al., Pharmazie, 56:927-32(2001), benzophenone derivatives (Sasse, A. et al., Arch. Pharm. (Weinheim) 334:45-52 (2001)) substituted N-phenylcarbamate (Reidemeister, S. et al., Pharmazie, 55:83-6(2000)), proxyphene derivatives (Sasse, A. et al., J. Med. Chem. 43:3335-43(2000)) and the like; 6)MCH-1R antagonists such as T-226296 (Takeda), SNAP-7941 (Synaptic) and other compounds disclosed in WO01/82925, WO01/87834, WO02/051809, WO02/06245, WO02/076929, WO02/076947, WO02/04433, WO02/51809, WO02/083134, WO02/094799, WO03/004027 and JP2001-226269A, and the like; 7) MCH-2R agonist/antagonists; 8) NPY1 antagonists such as 3-chloro-5-(1-(6-[2-(5-ethyl-4-methyl-thiazol-2-yl)-ethyl]-4-morpholinyl-4-yl-pyridin-2-ylamino)-ethyl)phenyl] carbamic acid isopropyl ester, BIBP3226, BIBO3304, LY-357897, CP-671906, GI-264879, and other compounds disclosed in U.S. Pat. No. 6,001,836, WO96/14307, WO01/23387, WO99/51600, WO01/85690, WO01/85098, WO01/85173 and WO01/89528, and the like; 9) NPY5 antagonists such as L-152804, GW-569180A, GW-594884A, GW-587081X, GW-548118X, FR235,208, FR226928, FR240662, FR252384, 1229U91, GI-264879A, CGP71683A, LY-377897, LY366377, PD-160170, SR-120562A, SR-120819A, JCF-104, H409/22, and other compounds disclosed in U.S. Pat. Nos. 6,140,354, 6,191,160, 6,258,837, 6,313,298, 6,337,332, 6,329,395, 340,683, 6,326, 375, 6,329,395, 6,337,332, 6,335,345, EP-01010691, EP-01044970, WO97/19682, WO97/20820, WO97/20821, WO97/20822, WO97/20823, WO98/27063, WO00/107409, WO00/185714, WO00/185730, WO00/64880, WO00/68197, WO00/69849, WO01/09120, WO01/14376, WO01/85714, WO1/85730, WO01/07409, WO01/02379, WO01/02379, WO01/23388, WO01/23389, WO01/44201, WO01/62737, WO01/62738, WO01/09120, WO02/20488, WO02/22592, WO02/48152, WO02/49648, WO02/094789 and Norman et al., J. Med. Chem. 43:4288-4312(2000), and the like; 10) leptins such as human recombinant leptin (PEG-OB, Hoffman La Roche), recombinant methionyl-leptin (Amgen) and the like; 11) leptin derivatives such as those compounds which are disclosed in U.S. Pat. Nos. 5,552,524, 5,552,523, 5,552,522, 5,521,283, WO96/23513, WO96/23514, WO96/23515, WO96/23516, WO96/23517, WO96/23518, WO96/23519 and WO96/23520, and the like; 12) opioid antagonists such as Nalmefene (registered trademark to Revex), 3-methoxynaltrexone, naloxone, naltrexone, compounds disclosed in WO00/21509 and the like; 13) orexin antagonists such as SB-334867A and other compounds disclosed in WO01/96302, WO01/68609, WO02/51232, WO02/51838, WO03/023561, and the like; 14) bombesin receptor subtype 3 agonist; 15) cholecystokinin A (CCK-A) agonists such as AR-R15849, GI-181771, JMV-180, A-71378, A-71623, SR-146131, other compounds disclosed in USP-5739106, and the like; 16) CNTF (ciliary neurotrophic factors) such as GI-181771 (Glaxo-SmithKline), SR146131 (Sanofi Synthelabo), butabindide, PD170,292, PD149164 (Pfizer) and the like; 17) CNTF derivatives such as axokine (Regeneron), other compounds which are disclosed in WO94/09134, WO98/22128 and WO99/43813, and the like; 18) growth hormone secretion receptor agonists such as NN 703, hexarelin, MK-0677, SM-130686, CP-424,391, L-692,429, L-163, 255, U.S. Pat. No. 6,358,951, U.S. Patent Application Nos. 2002/049196 and 2002/022637, WO01/56592 and WO02/32888, and the like; 19) serotonin receptor 2C agonists such as BVT933, DPCA37215, IK264, PNU22394, WAY161503, R-1065, YM348, other compounds disclosed in U.S. Pat. No. 3,914,250, WO02/36596, WO02/48124, WO02/10169, WO01/66548, WO02/44152, WO02/51844, WO02/40456 and WO02/40457, and the like; 20) melanocortin 3 receptor agonist; 21) melanocortin 4 receptor agonists such as CHIR86036 (Chiron), ME-10142, ME-10145 (Melacure), other compounds disclosed in WO99/64002, WO00/74679, WO01/991752, WO01/74844, WO01/70708, WO01/70337, WO01/91752, WO02/059095, WO02/059107, WO02/

059108, WO02/059117, WO02/12166, WO02/11715, WO02/12178, WO02/15909, WO02/068387, WO02/068388, WO02/067869, WO03/007949 and WO03/009847, and the like; 22) monoamine resorption inhibitors such as Sibutramine (registered trademark to Meridia/Reductil) and salts thereof, other derivatives disclosed in U.S. Pat. Nos. 4,746,680 4,806,570, 5,436,272, US Patent Application No. 2002/0006964, WO01/27068 and WO01/62341, and the like; 23) monoamine re-introjection inhibitors such as dexfenfluramine, fluoxetine, other compounds disclosed in U.S. Pat. No. 6,365,633, WO01/27060 and WO01/162341, and the like; 24) glucagons-like peptide 1 agonist; 25) Topiramate (registered trademark to Topimax); 26) phytopharm compound 57 (e.g., CP644,673); 27)acetyl CoA carboxylase 2 (ACC2) inhibitor; 28) β-adrenalin receptor 3 agonists such as AD9677/TAK677 (Dainippon Pharmaceutical/Takeda Pharmaceutical), CL-316,243, SB418790, BRL-37344, L-796568, BMS-196085, BRL-35135A, CGP12177A, BTA-243, W427353, Trecadrine, ZenecaD7114, SR59119A, other compounds disclosed in U.S. Pat. Nos. 5,705,515, 5,451,677, WO01/74782 and WO02/32897, and the like; 29) diacylglycerolacyl transferase 1 inhibitor; 30) diacylglycerolacyl transferase 2 inhibitor; 31) fatty acid synthesis inhibitors such as Cerulenin, C75 and the like; 32) phosphodiesterase inhibitors such as theofylline pentoxyfylline, zaprinast, sildenafil, amrinone, milrinone, cilostamide, rolipram, cilomilast and the like; 32) thyroid hormone β agonists such as KB-2611 (KaroBio BMS), other compounds disclosed in WO02/15845 and JP2000-256190A, and the like; 33) phytanic acid such as phytanic acid, 4-[(E)-2-(5,6,7,8-tetrahydro-5,5,8,8-tetramethyl-2-naphthalenyl)-1-propenyl] benzoic acid (TTNPB), retinoic acid, other compounds disclosed in WO99/00123, and the like; 34) acyl estrogens such as oleoylestrone, compounds disclosed in del Mar-Grasa, M. et al., Obesity Reseach, 9: 202-9(2001); 35) glucocorticoid antagonist; 36) 11-β hydroxysteroid dehydrognase 1-type inhibitors such as BVT 3498, BVT 2733, other compounds disclosed in WO01/90091, WO 01/90090 and WO01/90092, and the like; 37) stearyl-CoA desaturase 1 inhibitors; 38) dipeptidyl peptidase IV inhibitors such as isoleucine thiazolidide, valine pyrrolidide, NVP-DPP728 AF237, P93/01, TSL225, TMC-2A/2B/2C, FE999011, P9310/K364, VIP0177, SDZ274-444, other compounds disclosed in WO03/004498, WO03/004496, EP1258476, WO02/083128, WO02/062764, WO03/000250, WO03/002530, WO03/002531, WO03/002553, WO03/002593, WO03/000180 and WO03/000181, and the like; 39) lipase inhibitors such as Tetrahydro lipstatin (registered trademark to Orlistat/Xenical), Triton WR 1339, RHC 80267, lipstatin, tea saponin, diethylumbelliferyl phosphate, FL-386, WAY-121898, BAY-N-3176, valilactone, esteracin, ebelactone A, ebelectone B, RHC80267, other compounds disclosed in WO01/77094, U.S. Pat. Nos. 4,598,089, 4,452, 813, 5,512,565, 5,391,571, 5,602,151, 4,405,644, 4,189,438 and 4,242,453, and the like; 39) fatty acid transporter inhibitors; 40) dicarboxylate transporter inhibitors; 41) glucose transporter inhibitors; 42) phosphate transporter inhibitors; and the like can be named.

Those combination drugs are obtained by concurrent use of a compound of the present invention with one, two, or more of above drugs for combined use. Furthermore, said combination drugs are useful for prevention or therapy of metabolic disorders, when combined with one, two or more drugs selected from the group consisting of diabetes-treating agents and hyperlipidemia-treating agents. Combinations containing, in particular, hypertension-treating agent and antiobesity agent are useful for prevention or therapy of metabolic disorders with synergistic effect, when diabetes-treating agent(s) and/or hyperlipidemia-treating agent(s) are added thereto.

BRIEF EXPLANATION OF DRAWING

Rats had been satiated with high fat diet, a compound of the present invention was orally administered to them and an hour thereafter MCH was intraventricularly administered. The amounts of feed intake by the rats during the following two hours are shown in FIG. 1.

BEST MODE FOR CARRYING OUT THE INVENTION

Figure 1:
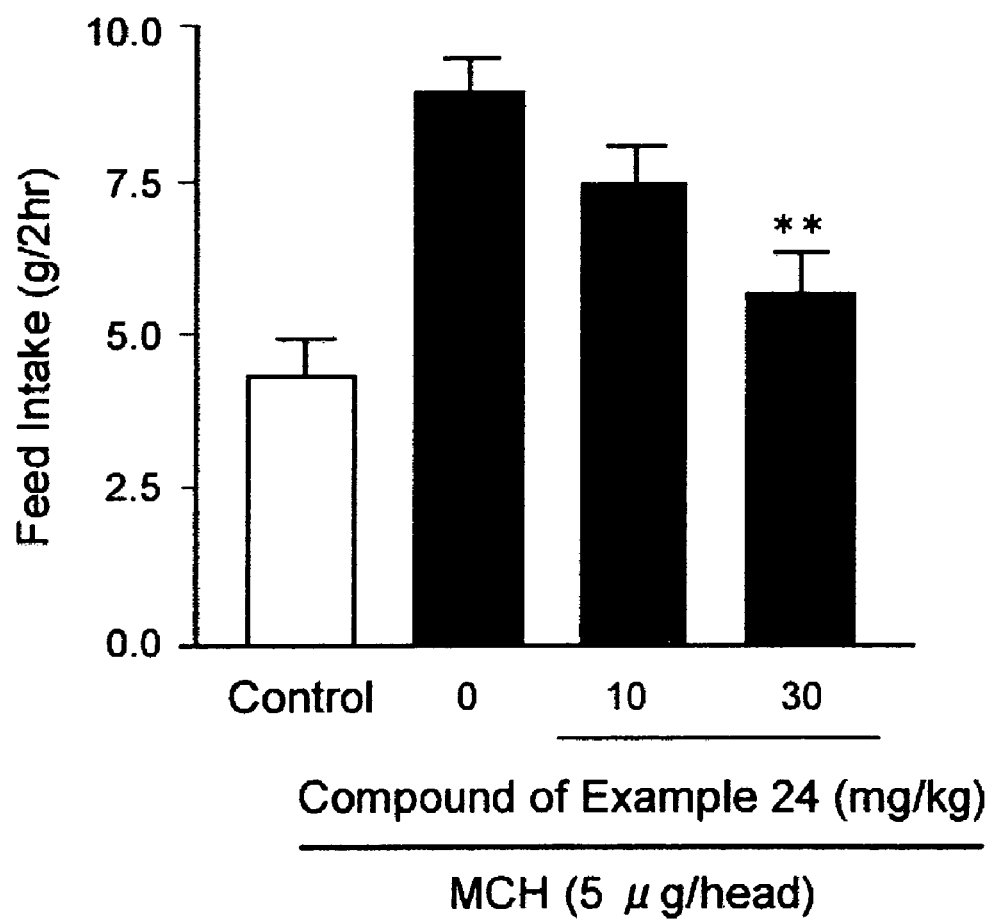

Hereinafter the present invention is explained in detail, referring to working Examples, it being understood that the invention is in no sense limited by said Examples. Unless specifically identified, those various reagents used in the Examples were commercial products. In H-NMR, tetramethylsilane was used as the standard substance.

EXAMPLE 1

Production of N-{2-[isopropyl(methyl)amino]-1H-benzimidazol-6-yl}-3-[4-(trifluoromethyl)phenyl] propanamide (1) To a suspension of 2-chloro-6-nitrobenzimidazole (5.00 g) in dioxane (5 ml), N-isopropylmethylamine (20 ml) was added, and heated in a sealed tube at 130° C. for 15 hours. The reaction liquid was cooled off, to which water was then added, followed by extraction with ethyl acetate. The organic layer was washed with saturated brine and dried over anhydrous sodium sulfate. The organic layer was condensed under reduced pressure, and the resulting residue was purified on silica gel column chromatography (ethyl acetate) to provide the title compound (3.55 g).

$^1$H-NMR(200 MHz, CD3OD, δppm): 1.26(6H, d, J=6.6 Hz), 4.37(1H, septet, J=6.6 Hz), 7.21(1H, d, J=8.3 Hz), 7.96-8.05(2H,m).

(2) To a solution of said N-{2-[isopropyl(methyl)amino]-6-nitro-1H-benzimidazole (1.00 g) as obtained in Example 1-(1) in methanol (30 ml), 20% palladium hydroxide-carbon (200 mg) was added and stirred at room temperature under atmospheric pressure for 5 hours. The reaction solution was filtered through Celite, and the filtrate was condensed under reduced pressure. Thus obtained 6-amino-N-{2-isopropyl (methyl)amino]-1H-benzimidazole was dissolved in chloroform (15 ml), followed by successive addition of triethylamine (1.8 ml) and 3-[4-(trifluoromethyl)phenyl]propionic acid (930 mg) and dropwise addition, under cooling with ice, of 2-chloro-1,3-dimethyl-2-imidazolinium chloride (2M chloroform solution, 2.6 ml). After 15 hours' stirring at room temperature, water was added, followed by extraction with ethyl acetate. The organic layer was washed with saturated brine and dried over anhydrous sodium sulfate. The organic layer was condensed under reduced pressure, the resultant residue was purified on silica gel column chromatography, (methanol/ethyl acetate=1/10) and washed with ether to provide the title compound (1.00 g).

$^1$H-NMR(400 MHz, DMSO-d6, δppm): 1.14(6H, d, J=6.8 Hz), 2.62(2H, t, J=7.6 Hz), 2.84(3H,s), 3.00(2H, t, J=7.6 Hz), 4.42(1H,m), 6.96(1H, d, J=8.4 Hz), 7.01(1H, d, J=8.4 Hz), 7.48(2H, d, J=8.1 Hz) 7.55(1H,s), 7.64(2H, d, 8.1 Hz), 9.69 (1H,s).

EXAMPLE 2

Production of N-{2-[2-(hydroxymethyl)-1-pyrrolidinyl-1H-benzimidazol-6-yl}-3-[4-(trifluoromethyl)phenyl]propanamide (1) To a suspension of 6-nitro-2-chlorobenzimidazole (5.00 g) in acetonitrile (150 ml) and acetone (50 ml), 4-dimethylaminopyridine (300 g) and di-tert-butyldicarbonate (6.0 g) were added and stirred at room temperature for 18 hours. The solvent was distilled off under reduced pressure, and the resulting solid was successively washed with water and ethyl acetate. Drying the solid under reduced pressure, a mixture (5.50 g) of the title compound was obtained.

(2) To a suspension of said tert-butyl-2-chloro-5-nitro-1H-chlorobenzimidazole-1-carboxylate/tert-butyl 2-chloro-6-nitro-1H-chlorobenzimidazole-1-carboxylate mixture (400 mg) in dioxane (30 ml), potassium carbonate (740 mg) and 2-hydroxymethylpyrrolidine hydrochloride (1.09 g) were added and heated under reflux for 15 hours. Cooling the reaction liquid off, saturated aqueous ammonium chloride solution was added, followed by extraction with ethyl acetate. The organic layer was washed with saturated brine and dried over anhydrous sodium sulfate. The organic layer was condensed under reduced pressure and solidified to dryness. The residue was washed with ether-ethyl acetate mixed solution to provide the title compound (300 mg).

$^1$H-NMR(400 MHz, DMSO-d6, δppm): 1.91-2.07(4H,m), 3.44-3.60(4H,m), 4.00-4.05(1H,m), 5.08(1H,s), 7.22(1H, d, J=7.8 Hz), 7.83-7.92(2H,m).

(3) Using the 2-[2-hydroxymethyl]-1-pyrrolidinyl-6-nitro-1H-benzimidazole as obtained in Example 2-(2), the title compound was obtained in the manner similar to Example 1-(2).

1H-NMR(400 MHz, CDCl3, δppm): 1.60-1.70(1H,m), 1.90-2.00(2H,m), 2.02-2.15(1H,m), 2.64(2H, t, J=7.2 Hz), 3.10(2H, t, J=7.2 Hz), 3.44-3.68(3H,m), 3.73-3.80(1H,m), 3.93-4.02(1H,m), 6.82(1H, d, J=8.0 Hz), 6.98(1H, d, J=8.0 Hz), 7.34(2H, d, J=8.0 Hz), 7.52(3H, d, J=8.0 Hz).

EXAMPLE 3

Production of 4-(4-fluorophenyl)-N-{2-[isopropyl(methyl)-amino]-1H-benzimidazol-6-yl}-1-piperidinecarboxamide (1) To a solution of N-{2-[isopropyl(methyl)amino]-6-nitro-1H-benzimidazole (280 mg) as obtained in Example 1-(1) in tetrahydrofuran (5 ml), 4-dimethylaminopyridine (176 mg) and di-tert-butyldicarbonate (391 mg) were added and stirred at room temperature for 3.5 hours. Water was added and the system was extracted with ether. The organic layer was washed with saturated brine and dried over anhydrous sodium sulfate. The organic layer was condensed under reduced pressure and the residue was purified on silica gel column chromatography (hexane/ethyl acetate=1/4) to provide a mixture (429 mg) of tert-butyl N-{2-isopropyl(methyl)-amino]-5-nitro-1H-chlorobenzimidazole-1-carboxylate and tert-butyl N-{2-[isopropyl(methyl)amino]-6-nitro-1H-chlorobenzimidazole-1-carboxylate.

(2) To a solution of so obtained mixture (429 mg) of tert-butyl N-{2-isopropyl(methyl)-amino]-5-nitro-1H-chlorobenzimidazole-1-carboxylate and tert-butyl N-{2-[isopropyl(methyl)amino]-6-nitro-1H-chlorobenzimidazole-1-carboxylate in methanol (5 ml), 20% palladium hydroxide-carbon (150 mg) was added and stirred at room temperature under atmospheric pressure for 1.5 hours. The reaction liquid was filtered through Celite and the filtrate was condensed under reduced pressure. The resulting residue was dissolved in chloroform (5 ml), to which pyridine (0.29 ml) was added and further phenyl chloroformate (0.30 ml) was added dropwise under cooling with ice. After subsequent 40 minutes' stirring at room temperature, saturated aqueous sodium hydrogencarbonate solution was added to the reaction liquid, followed by extraction with ethyl acetate. The organic layer was washed with saturated brine and dried over anhydrous sodium sulfate. The organic layer was condensed under reduced pressure and the resultant residue was purified on silica gel column chromatography (hexane/ethyl acetate=3/7) to provide a mixture (430 mg) of tert-butyl 2-[isopropyl(methyl)amino]-5-[(phenoxycarbonyl)amino]-1H-benzimidazole-1-carboxylate and tert-butyl 2-[isopropyl(methyl)-amino]-6-[(phenoxycarbonyl)amino]-1H-benzimidazole-1-carboxylate.

(3) To a solution of said mixture (157 mg of tert-butyl-2-[isopropyl(methyl)amino]-5-[(phenoxycarbonyl)amino]-1H-benzimidazole-1-carboxylate and tert-butyl 2-[isopropyl(methyl) amino]-6-[(phenoxycarbonyl)amino]-1H-benzimidazole-1-carboxylate in chloroform (3 ml), 4-(4-fluorophenyl)piperidine hydrochloride (76 mg) and triethylamine (0.16 ml) were added and heated at 60° C. for 1.5 hours. The reaction liquid was cooled and after addition of water, extracted with chloroform. The organic layer was washed with saturated brine and dried over anhydrous sodium sulfate. The organic layer was condensed under reduced pressure and the resulting residue was purified on preparative TLC (hexane/ethyl acetate=1/9). Thus obtained compound was dissolved in trifluoroacetic acid (2 ml) and stirred for an hour. The reaction liquid was made alkaline by addition of 4N-aqueous NaOH solution and extracted with chloroform. The organic layer was washed with saturated brine and dried over anhydrous sodium sulfate. The organic layer was condensed under reduced pressure and purified on preparative TLC (methanol/chloroform=1/9) to provide the title compound (11 mg).

1H-NMR(300 MHz, CDCl3, δppm): 0.95-1.11(6H,m), 1.49-1.71(2H,m), 1.73-1.91(2H,m), 1.73-1.91(2H,m), 2.57-2.73(1H,m), 2.76(3H,s), 2.77-3.01(2H,m), 4.20-4.44(3H,m), 6.73-6.88(1H,m), 6.87-7.15(5H,m), 7.19-7.21(1H,m), 7.28-7.48(1H,br.s).

EXAMPLE 4

Production of N-{2-[isopropyl(methyl)amino]-1H-benzimidazol-6-yl}-N-methyl-5-[4-(trifluoromethyl)phenyl]-1,2,4-oxadiazole-3-carboxamide (1) To a solution of 6-amino-N-{2-[isopropyl(methyl)amino]-1H-benzimidazole (340 mg) which was obtained in Example 1-(2) in tetrahydrofuran (12 ml), triethylamine (0.52 ml), 4-dimethyl-aminopyridine (149 mg) and di-tert-butyl dicarbonate (587 mg) were added and stirred at room temperature for 15 hours. Water was added and the system was extracted with ethyl acetate. The organic layer was washed with saturated brine and dried over anhydrous sodium sulfate. The organic layer was condensed under reduced pressure and the resultant residue was purified on silica gel column chromatography (hexane/ethyl acetate)=1/1) to provide a mixture (268 mg) of tert-butyl 5-[(t-butoxycarbonyl)amino]-2-[isopropyl-(methyl)amino]-1H-benzimidazole-1-carboxylate and tert-butyl 6-[(t-butoxycarbonyl)amino]-2-[isopropyl (methyl)amino]-1H-benzimidazole-1-carboxylate.

(2) To a solution of said mixture (268 mg) of tert-butyl 5-[(t-butoxycarbonyl)amino]-2-[isopropyl(methyl)amino]-1H-benzimidazole-1-carboxylate and tert-butyl 6-[(t-butoxycarbonyl)amino]-2-[isopropyl-(methyl)amino]-1H-benzimidazole-1-carboxylate in dimethylformamide (6.6 ml), methyl iodide (0.43 ml) and sodium hydride (60% oil-form; 149 mg) were added under cooling with ice and stirred for 2 hours. Water was added and the system was extracted with ethyl acetate. The organic layer was washed with saturated brine and dried over anhydrous sodium sulfate. The organic layer was condensed under reduced pressure and the resulting residue was purified on preparative TLC (hexane/ethyl acetate=7/3) to provide a mixture (207 mg) of tert-butyl 5-[(t-butoxycarbonyl)(methyl)amino]-2-[isopropyl(methyl) amino-1H-benzimidazole-1-carboxylate and tert-butyl 6-[(t-butoxycarbonyl)(methyl)amino]-2-[isopropyl(methyl) amino]-1H-benzimidazole-1-carboxylate.

(3) Thus obtained mixture (207 mg) of tert-butyl 5-[(t-butoxycarbonyl)(methyl)amino]-2-[isopropyl(methyl) amino-1H-benzimidazole-1-carboxylate and tert-butyl 6-[(t-butoxycarbonyl)(methyl)amino]-2-[isopropyl(methyl) amino]-1H-benzimidazole-1-carboxylate was dissolved in trifluoroacetic acid (2 ml) and stirred for 3.5 hours. The reaction liquid was made alkaline by addition of 4N-aqueous NaOH solution and extracted with chloroform. The organic layer was washed with saturated brine and dried over anhydrous sodium sulfate to provide an oily substance (117 mg). Thus obtained amine-form (61 mg) was dissolved in dimethylformamide (2.5 ml), and to the solution carboxylic acid (61 mg), WSC.HCl (67 mg), HOBt.monohydrate (47 mg) and sodium hydrogencarbonate (79 mg) were added, followed by stirring at room temperature for 15 hours. Water was added and the system was extracted with ethyl acetate. The organic layer was washed with saturated brine and dried over anhydrous sodium sulfate. The organic layer was condensed under reduced pressure and purified on preparative TLC (methanol/chloroform=1/9) to provide the title compound (34 mg).

1H-NMR(300 MHz, DMSO-d6, δppm): 1.11(6H, d, J=6.9 Hz), 2.29(3H,s), 3.45(3H,s), 4.41(1H, septet, J=6.9 Hz), 6.75-6.88(1H,m), 6.97-7.07(1H,m), 7.12(1H,s), 7.88(2H, d, J=8.4 Hz), 8.05(2H, d, J=8.4 Hz).

The reactions in the following Examples 5-49 were conducted in the manner similar to Example 1, except that 3-[4-(trifluoromethyl)phenyl]propionic acid which was used in Example 1-(2) was replaced with a starting material corresponding to the intended product compound in each run.

EXAMPLE 5

N-{2-[isopropyl(methyl)amino]-1H-benzimidazol-6-yl}-3-[5-(trifluoromethyl)-2-pyridinyl]propanamide 1H-NMR(300 MHz, DMSO-d6, δppm): 1.24(6H, d, J=6.6 Hz), 2.85(2H, t, J=7.3 Hz), 3.03(3H,s), 3.18(2H, t, J=7.3 Hz), 4.33(1H,m), 7.28(1H, d, J=8.7 Hz), 7.36(1H, d, J=8.7 Hz), 7.59(1H, d, J=8.3 Hz), 7.90(1H,brs), 8.14(1H, d, J=8.3 Hz), 8.88(1H,s), 10.30(1H,s).

EXAMPLE 6

N-{(2-[ispronyl(methyl)amino]-1H-benzimidazol-6-yl}-2-{[5-(trifluoromethyl)-2-pyridinyl]oxy}acetamide ¹H-NMR(400 MHz, DMSO-d6, δppm): 1.20(6H, d, J=6.8 Hz), 3.17(3H,s), 4.40-4.43(1H,m), 4.98(2H,s), 7.00-7.16 (3H,m), 7.31-7.42(1H,m), 8.05-8.12(1H,m), 8.55(1H,s), 9.90(3H,s), 11.03(1H,s).

EXAMPLE 7

N-{2-[isopropyl(methyl)amino]-1H-benzimidazol-6-yl}-3-[6-(trifluoromethyl)-3-pyridinyl]propanamide 1H-NMR(300 MHz, CD3OD, δppm): 1.24(6H, d, J=6.6 Hz), 2.73(2H, t, J=7.3 Hz), 2.93(3H, d), 3.13(2H, t, J=7.3 Hz), 4.47(1H,m), 6.97(1H, d, J=8.5 Hz), 7.10(1H, d, J=8.5 Hz), 7.51(1H,s), 7.73(1H, d, J=8.0 Hz), 7.94(1H, d, J=8.0 Hz), 8.63(1H,s).

EXAMPLE 8

(E)-N-{2-[isopropyl(methyl)amino]-1H-benzimidazol-6-yl}-3-(1-oxo-1,3-dihydro-2-benzofuran-5-yl)-2-propenamide ¹H-NMR(400 MHz, DMSO-d6, δppm): 1.13(6H, d, J=6.8 Hz), 3.29(3H,s), 4.41(1H, septet, J=6.8 Hz), 5.44(2H,s), 6.98-7.15(3H,m), 7.60-7.90(5H,m).

EXAMPLE 9

N-{2-[isopropyl(methyl)amino]-1H-benzimidazol-6-yl}-3-(4-methoxyphenyl)propanamide ¹H-NMR(400 MHz, DMSO-d6, δppm): 1.20(6H, d, J=6.8 Hz), 2.50(2H, t, J=7.2 Hz), 3.00(2H, t, J=7.2 Hz), 3.28(3H,s), 4.41(1H, septet, J=6.8 Hz), 6.81(2H, d, J=5.2 Hz), 6.91-6.98 (2H,m), 7.14(2H, d, J=5.2 Hz), 7.63(1H,s), 9.63(1H,s).

EXAMPLE 10

N-{2-[isopropyl(methyl)amino]-1H-benzimidazol-6-yl}-3-[3-fluoro-4-methoxyphenyl]propenamide ¹H-NMR(400 MHz, DMSO-d6, δppm): 1.13(6H, d, J=6.4 Hz), 3.28(3H,s), 3.86(3H,s), 4.41(1H, septet, J=6.4 Hz), 6.69 (1H, d, J=14.8 Hz), 7.02-7.21(3H,m), 7.45(1H, d, J=14.8 Hz) 7.42-7.61(3H,m).

EXAMPLE 11

4-(2-Fluoro-4-pyridinyl)-N-{2-[isopropyl(methyl)amino]-1H-benzimidazol-6-yl}benzamide 1H-NMR(300 MHz, DMSO-d6, δppm): 1.27(6H, d, J=6.4 Hz), 3.03(3H,s), 4.21(1H,m), 7.37(1H, d, J=8.7 Hz), 7.58 (1H, brd, J=8.7 Hz), 7.65(1H,brs), 7.80(1H,m), 8.08(5H,m), 8.36(1H, d, J=5.3 Hz), 10.51(1H,s).

EXAMPLE 12

4-(4-Fluoro-3-pyridinyl)-N-{2-[isopropyl(methyl)amino]-1H-benzimidazol-6-yl}benzamide 1H-NMR(300 MHz, CD3OD, δppm): 1.26(6H, d, J=6.6 Hz), 2.96(3H,s), 4.41(1H,m), 6.92(1H,s), 7.19(3H,m), 7.80 (2H, d, J=8.3 Hz), 8.06(2H, d, J=8.3 Hz), 8.27(1H, ddd, J=8.0,8.0,2.7 Hz), 8.53(1H, d, J=2.7 Hz).

EXAMPLE 13

N-{2-[isopropyl(methyl)amino]-1H-benzimidazol-6-yl}-4-(2-pyrimidinyl)benzamide

1H-NMR(400 MHz, CDCl3, δppm): 1.07(6H, d, J=6.8 Hz), 2.81(3H,s), 4.26-4.42(1H,m), 7.03(1H, brd, J=8.4 Hz), 7.12(1H, brd, J=8.4 Hz), 7.20(1H, dd, J1=J2=4.8 Hz), 7.57 (1H,brs), 8.01(2H, d, J=8.0 Hz), 8.48(2H, d, J=8.0 Hz), 8.71 (1H,brs), 8.79(2H, d, J=4.8 Hz).

EXAMPLE 14

4-Cyclohexyl-N-{2-[isopropyl(methyl)amino]-1H-benzimidazol-6-yl}benzamide

1H-NMR(300 MHz, CDCl3, δppm): 0.98-1.17(6H,m), 1.23-1.52(4H,m), 1.67-1.95(6H,m), 2.42-2.63(1H,m), 2.80 (3H,s), 4.28-4.44(1H,m), 6.87-7.04(1H,m), 7.03-7.17(1H, m), 7.15-7.32(2H,m), 7.49-7.62(1H,m), 7.74-7.88(2H,m), 8.26-8.43(1H,m).

EXAMPLE 15

N-{2-[isopropyl(methyl)amino]-1H-benzimidazol-6-yl}-4-(6-methoxy-2-pyridinyl)benzamide 1H-NMR(400 MHz, CDCl3, δppm): 1.08(6H, d, J=6.4 Hz), 2.81(3H,s), 4.01(3H,s), 4.36-4.43(1H,m), 6.70(1H, d, J=8.4 Hz), 7.02(1H, brd, J=8.0 Hz), 7.13(1H, d, J=8.4 Hz), 7.34(1H, d, J=7.2 Hz), 7.59-7.63(2H,m), 7.98(2H, d, J=8.4 Hz), 8.09(2H, d, J=8.4 Hz), 8.56(1H,brs).

EXAMPLE 16

N-{2-[isopropyl(methyl)amino]-1H-benzimidazol-6-yl}-4-morpholinobenzamide

1H-NMR(300 MHz, DMSO-d6, δppm): 1.15(6H, d, J=6.6 Hz), 2.86(3H,s), 3.18-3.32(4H,m), 3.68-3.81(4H,m), 4.44(1H, septet, J=6.6 Hz), 6.95-7.13(1H,m), 7.01(2H, d, J=8.7 Hz), 6.95-7.13(1H,m), 7.77(2H, d, J=8.7 Hz), 9.68-9.78(1H,m), 10.96-11.01(1H,m).

EXAMPLE 17

N-{2-[isopropyl(methyl)amino]-1H-benzimidazol-6-yl}-4-(6-methoxy-3-pyridinyl)benzamide 1H-NMR(400 MHz, CD3OD, δppm): 1.25(6H, d, J=6.4 Hz), 2.95(3H, s), 3.94(3H,s), 4.32-4.43(1H,m), 6.86(1H, d, J=9.6 Hz), 7.15-7.21(2H,m), 7.67-7.69(3H,m), 7.93-7.99 (3H,m), 8.41(1H, d, J=1.6 Hz).

EXAMPLE 18

N-{2-[isopropyl(methyl)amino]-1H-benzimidazol-6-yl}-4-piperidinobenzamide

1H-NMR(300 MHz, CDCl3, δppm): 1.17(6H, d, J=6.6 Hz), 1.57-1.78(6H,m), 2.88(3H,s), 3.26-3.34(2H,m), 4.45(1H, septet, J=6.6 Hz), 6.92(2H, d, J=9.0 Hz), 6.88-7.05 (1H,m), 7.19-7.24(1H,m), 7.79(2H, d, J=9.0 Hz), 7.86(1H, br.s).

EXAMPLE 19

N-{2-[isopropyl(methyl)amino]-1H-benzimidazol-6-yl}-4-[(2-trifluoromethyl)-3-pyridinyl]benzamide 1H-NMR(300 MHz, DMSO-d6, δppm): 1.27(6H, d, J=6.3 Hz), 3.07(3H,s), 4.37(1H,m), 7.37(1H,m), 7.52-7.67(2H,m), 7.97-8.19(5H,m), 8.47(1H, d, J=8.2 Hz), 9.19(1H,s), 10.58 (1H,s).

EXAMPLE 20

4-(2-Fluoro-4-pyridyl)-N-{2-[isopropyl(methyl)amino]-1H-benzimidazol-6-yl}-2-pyridinecarboxamide 1H-NMR(300 MHz, DMSO-d6, δppm): 1.24(6H, d, J=6.6 Hz), 2.85(2H, t, J=7.3 Hz), 3.03(3H,s), 3.18(2H, t, J=7.3 Hz), 4.33(1H,m), 7.28(1H, d, J=8.7 Hz), 7.36(1H, d, J=8.7 Hz), 7.59(1H, d, J=8.3 Hz), 7.90(1H,brs), 8.14(1H, d, J=8.3 Hz), 8.88(1H,s), 10.30(1H,s).

EXAMPLE 21

5-(4-Fluorophenyl)-N-{2-[isopropyl(methyl)amino]-1H-benzimidazol-6-yl}-2-pyridinecarboxamide 1H-NMR(300 MHz, DMSO-d6, δppm): 1.26(6H, d, J=6.6 Hz), 3.07(3H,s), 4.38(1H,m), 7.38(3H,m), 7.73(1H, brd, J=8.8 Hz), 7.89(2H, dd, J=8.8, 5.3 Hz), 8.18(1H,brs), 8.21 (1H, brd, J=8.2 Hz), 8.34(1H, brd, J=8.2 Hz), 9.00(1H,brs), 10.82(1H,s).

EXAMPLE 22

N-{2-[isopropyl(methyl)amino]-1H-benzimidazol-6-yl}-5-[4-(trifluoromethyl)phenyl]-1,2,4-oxadiazole-3-carboxamide 1H-NMR(300 MHz, CD3OD, δppm): 1.39(6H, d, J=6.6 Hz), 3.12(3H,s)4.22(1H, septet, J=6.6 Hz)7.38(1H, d, J=8.6 Hz), 7.56(1H, dd, J=2.0, 8.6 Hz), 7.98(2H, d, J=8.3 Hz) 8.13(1H, d, J=2.0 Hz), 8.45(2H, d, J=8.3 Hz).

EXAMPLE 23

N-{2-[isopropyl(methyl)amino]-1H-benzimidazol-6-yl}-3-[4-(trifluoromethyl)phenyl]-1,2,4-oxadiazole-5-carboxamide 1H-NMR(300 MHz, CD3OD, δppm): 1.38(6H, d, J=6.6 Hz), 3.12(3H,s), 4.22(1H, septet, J=6.6 Hz), 7.40(1H, d, J=8.4 Hz, 7.60(1H, dd, J=1.2, 8.4 Hz), 7.91(2H, d, J=8.4 Hz), 8.13(1H, d, J=1.2 Hz), 8.38(2H, d, J=8.4 Hz).

EXAMPLE 24

5-(4-Fluorophenyl)-N-{2-[isopropyl(methyl)amino]-1H-benzimidazol-6-yl}-2-pyrazinecarboxamide hydrochloride The reaction was conducted following Example 1 except that 3-[4-(trifluoromethyl)phenyl]propionic acid which was used in Example 1-(2) was replaced with 5-(4-fluorophenyl)-2-pyrazinecarboxylic acid, and the resulting product was treated with 4N hydrochloric acid-ethyl acetate to provide the title compound.

1H-NMR(300 MHz, DMSO-d6, δppm): 1.26(6H, d, J=6.3 Hz), 3.06(3H,s), 4.35(1H,m), 7.38(1H, d, J=8.7 Hz), 7.43 (2H, dd, J=8.9, 8.9 Hz), 7.70(1H, d, J=8.7 Hz), 8.15(1H,s), 8.33(2H, dd, J=8.9, 5.6 Hz), 9.31(1H,s), 9.35(1H,s), 10.88 (1H,s).

EXAMPLE 25

N-{2-[isopropyl(methyl)amino]-1H-benzimidazol-6-yl}-1-[4-trifluoromethyl)phenyl]-1,2,4-triazole-3-carboxamide 1H-NMR(300 MHz, DMSO-d6, δppm): 1.15(6H, d, J=6.6 Hz), 2.87(3H,s), 4.46(1H, septet, J=6.6 Hz), 7.09(1H, d, J=8.4 Hz), 7.30(1H, d, J=8.4 Hz), 7.68-7.87(1H,m), 8.02(2H, d, J=8.1 Hz), 8.23(2H, d, J=8.1 Hz), 9.63(1H,br.s).

EXAMPLE 26

3-(2-Fluorophenyl)-N-{2-[isopropyl(methyl)amino]-1H-benzimidazol-6-yl}-1,2,4-oxadiazole-5-carboxamide 1H-NMR(300 MHz, DMSO-d6, δppm): 1.20(6H, d, J=6.6 Hz), 2.95(3H,s), 4.55(1H, septet, J=6.6 Hz), 7.08-7.33(1H, m), 7.45-7.58(1H,m), 7.83(1H,s), 7.98-8.10(1H,m), 9.13(1H,br.s).

EXAMPLE 27

3-(3-Fluorophenyl)-N-{2-[isopropyl(methyl)amino]-1H-benzimidazol-6-yl}-1,2,4-oxadiazole-5-carboxamide 1H-NMR(300 MHz, DMSO-d6, δppm): 1.22(6H, d, J=6.6 Hz), 2.97(3H,s), 4.55(1H, septet, J=6.6 Hz), 7.09-7.33(4H, m), 7.41-7.54(1H,m), 7.76-7.95(3H,m), 9.04(1H,br.s).

EXAMPLE 28

3-(4-Fluorophenyl)-N-{2-[isopropyl(methyl)amino]-1H-benzimidazol-6-yl}-1,2,4-oxadiazole-5-carboxamide 1H-NMR(300 MHz, DMSO-d6, δppm): 1.15(6H, d, J=6.6 Hz), 2.87(3H,s), 4.46(1H, septet, J=6.6 Hz), 7.12(1H, d, J=8.4 Hz), 7.32(1H, d, J=8.4 Hz), 7.38-7.55(2H,m), 7.59-7.82(1H,m), 8.09-8.30(2H,m), 11.00-11.32(1H,m).

EXAMPLE 29

N-{2-[isopropyl(methyl)amino]-1H-benzimidazol-6-yl}-5-[4-(trifluoromethyl)phenyl]-1,3,4-oxadiazole-2-carboxamide 1H-NMR(300 MHz, CDCl3, δppm): 1.21(6H, d, J=6.0 Hz), 2.97(3H,s), 4.54(1H, septet, J=6.0 Hz), 7.08-7.32(2H, m), 7.70-7.89(1H,m), 7.80(2H, d, J=8.4 Hz), 8.27(2H, d, J=8.4 Hz), 9.03(1H,br.s).

EXAMPLE 30

3-(3,4-Difluorophenyl)-N-{2-[isopropyl(methyl)amino]-1H-benzimidazol-6-yl}-1,2,4-oxadiazole-5-carboxamide 1H-NMR(300 MHz, DMSO-d6, δppm): 1.02-1.23(6H,m), 2.80-2.97(3H,m), 4.36-4.61(1H,m), 7.05-7.18(1H,m), 7.23-7.49(1H,m), 7.57-8.19(4H,m), 11.08-11.27(1H,m).

EXAMPLE 31

6-(4-Fluorophenyl)-N-{2-[isopropyl(methyl)amino]-1H-benzimidazol-6-yl}-3-pyridinecarboxamide 1H-NMR(400 MHz, CDCl3, δppm): 1.08(6H, d, J=6.4 Hz), 2.81(3H,s), 4.28-4.46(1H,m), 6.98-7.09(4H,m), 7.41(1H,brs), 7.58(1H, d, J=8.0 Hz), 7.89(2H, dd, J=8.4, 5.6 Hz), 8.21(1H, brd, J=7.2 Hz), 9.14(1H,s), 9.48(1H,brs).

EXAMPLE 32

3-(2,4-Difluorophenyl)-N-{2-[isopropyl(methyl)amino]-1H-benzimidazol-6-yl}-1,2,4-oxodiazole-5-carboxamide 1H-NMR(300 MHz, DMSO-d6, δppm): 1.16(6H, d, J=6.6 Hz), 2.87(3H,s), 4.46(1H, septet, J=6.6 Hz), 7.12(1H, d, J=9.0 Hz), 7.32(1H, d, J=9.0 Hz), 7.33-7.42(1H,m), 7.54-7.78(3H,m), 8.12-8.26(1H,m), 11.00-11.29(1H,m).

EXAMPLE 33

N-{2-[isopropyl(methyl)amino]-1H-benzimidazol-6-yl}-5-methyl-1-[4-(trifluoromethyl)phenyl]-1H-pyrazole-4-carboxamide 1H-NMR(300 MHz, CD3OD, δppm): 1.28-1.42(6H,m), 2.59-2.68(3H,m), 3.04-3.13(3H,m), 4.12-4.28(1H,m), 7.30-7.46(2H,m), 7.70-7.80(2H,m), 7.84-7.95(2H,m), 8.00(1H,br.s), 8.26(1H,br.s).

EXAMPLE 34

N-{2-[isopropyl(methyl)amino]-1H-benzimidazol-6-yl}-5-phenyl-3-pyridinecarboxamide 1H-NMR(400 MHz, DMSO-d6, δppm): 1.17(6H, d, J=6.4 Hz), 2.88(3H,s), 4.40-4.49(1H,m), 7.09(1H, d, J=8.4 Hz), 7.23(1H, d, J=8.4 Hz), 7.46-7.54(3H,m), 7.72(1H,brs), 8.11 (1H, d, J=8.4 Hz), 8.16(2H, d, J=7.2 Hz), 8.36(1H, d, J=7.2 Hz), 9.17(1H,s), 10.23(1H,brs), 11.18(1H,brs).

EXAMPLE 35

N-{2-[isopropyl(methyl)amino]-1H-benzimidazol-6-yl}-2-[4-(trifluoromethyl)phenyl]-2H-tetrazole-2-carboxamide 1H-NMR(300 MHz, DMSO-d6, δppm): 1.16(6H, d, J=6.6 Hz), 2.96(3H,s), 4.47(1H, septet, J=6.6 Hz), 7.06-7.17(1H, m), 7.28-7.37(1H,m), 7.57-7.88(1H,m), 8.12(2H, d, J=9.0 Hz), 8.43(2H, d, J=9.0 Hz), 10.78-11.23(1H,m).

EXAMPLE 36

N-{2-[isopropyl(methyl)amino]-1H-benzimidazol-6-yl}-1-methyl-5-[4-(trifluoromethyl)phenyl]-1H-pyrazole-3-carboxamide 1H-NMR(300 MHz, CD3OD, δppm): 1.26(6H, d, J=6.6 Hz), 2.96(3H,s), 4.01(3H,s), 4.39(1H, septet, J=6.6 Hz), 6.96-7.01(1H,m), 7.13-7.27(2H,m), 7.69-7.86(5H,m).

EXAMPLE 37

N-{2-[isopropyl(methyl)amino]-1H-benzimidazol-6-yl})-1-methyl-3-[4-(trifluoromethyl)phenyl]-1H-pyrazole-5-carboxamide 1H-NMR(300 MHz, CD3OD, δppm): 1.26(6H, d, J=6.6 Hz), 2.85(3H,s), 4.21(3H,s), 4.40(1H, septet, J=6.6 Hz), 7.17-7.25(2H,m), 7.38(1H,s), 7.68(1H,s), 7.70(2H, d, J=8.4 Hz), 8.01(2H, d, J=8.4 Hz).

EXAMPLE 38

N-{2-[isopropyl(methyl)amino]-1H-benzimidazol-6-yl}-[2,2']-bipyridine-5-carboxamide 1H-NMR(400 MHz, DMSO-d6, δppm): 1.17(6H, d, J=6.4 Hz), 2.88(3H,s), 4.40-4.49(1H,m), 7.09(1H, d, J=8.4 Hz), 7.23(1H, d, J=8.4 Hz), 7.46-7.54(3H,m), 7.72(1H,brs), 8.11(1H, d, J=8.4 Hz), 8.16(2H, d, J=7.2 Hz), 8.36(1H, d, J=7.2 Hz), 9.17(1H,s), 10.23(1H,brs), 11.18(1H,brs).

EXAMPLE 39

N-{2-[isopropyl(methyl)amino]-1H-benzimidazol-6-yl}-5-phenyl-2-pyrazinecarboxamide 1H-NMR(400 MHz, DMSO-d6, δppm): 1.17(6H, d, J=6.4 Hz), 2.88(3H,s), 4.43-4.50(1H,m), 7.09(1H, d, J=8.4 Hz), 7.38(1H, d, J=8.4 Hz), 7.57-7.59(3H,m), 8.24(2H, d, J=8.0 Hz), 8.29(1H,s), 9.31(1H,s), 9.33(1H,s), 10.47(1H,brs).

EXAMPLE 40

6-(2-Fluorophenyl)-N-{2-[isopropyl(methyl)amino]-1H-benzimidazol-6-yl}-3-pyridinecarboxamide 1H-NMR(400 MHz, CD3OD, δppm): 1.26(6H, d, J=7.2 Hz), 2.95(3H,s), 4.36-4.42(1H,m), 7.13-7.33(4H,m), 7.45-7.51(1H,m), 7.72(1H, brd, J=2.0 Hz), 7.88-7.94(2H,m), 8.35(1H, dd, J=8.4, 2.4 Hz), 9.16(1H, brd, J=2.0 Hz).

EXAMPLE 41

6-(3-Fluorophenyl)-N-{2-[isopropyl(methyl)amino]-1H-benzimidazol-6-yl}-3-pyridinecarboxiamide 1H-NMR(400 MHz, CD3OD, δppm): 1.28(6H, d, J=6.8 Hz), 2.97(3H,s), 4.31-4.47(1H,m), 7.18-7.32(3H,m), 7.48-7.53(1H,m), 7.74(1H, brd, J=2.0 Hz), 7.80-7.87(2H,m), 7.95(1H, d, J=7.6 Hz), 8.34(1H, dd, J=8.4, 2.0 Hz), 9.14(1H, brd, J=2.0 Hz).

EXAMPLE 42

5-(4-Fluorophenyl)-N-{2-[isopropyl(methyl)amino]-1H-benzimidazol-6-yl}-2-pyrimidinecarboxamide 1H-NMR(300 MHz, DMSO-d6, δppm): 1.27(6H, d, J=6.6 Hz), 3.05(3H,s), 4.30(1H,m), 7.38(1H, d, J=8.6 Hz), 7.44(2H, dd, J=8.6, 8.6 Hz), 7.71(1H, d, J=8.6 Hz), 8.00(2H,m), 8.19(1H,s), 9.35(2H,s), 10.99(1H,s).

EXAMPLE 43

N-{2-[isopropyl(methyl)amino]-1H-benzimidazol-6-yl}-5-phenyl-5-pyrimidinecarboxamide 1H-NMR(400 MHz, DMSO-d6, δppm): 1.16(6H, d, J=6.4 Hz), 2.87(3H,s), 4.42-4.50(1H,m), 7.10(1H, d, J=8.4 Hz), 7.21(1H, d, J=8.4 Hz), 7.50-7.53(3H,m), 7.55(1H,brs), 8.47(2H, d, J=2.0 Hz), 9.33(2H,s), 10.36(1H,brs), 11.14(1H,brs).

EXAMPLE 44

5-(4-Fluorophenyl)-N-{2-[isopropyl(methyl)amino]-1H-benzimidazol-6-yl}-6-methoxy-2-pyridinecarboxamide 1H-NMR(300 MHz, DMSO-d6, δppm): 1.16(6H, d, J=6.8 Hz), 2.88(3H,s), 4.11(3H,s), 4.47(1H,m), 7.12(1H, d, J=8.2 Hz), 7.28(3H,m), 7.68(2H,m), 7.79(1H,s), 7.80(1H, d, J=7.6 Hz), 7.97(1H, d, J=7.6 Hz), 10.04(1H,s).

EXAMPLE 45

6-(4-Fluorophenyl)-N-{2-[isopropyl(methyl)amino]-1H-benzimidazol-6-yl}-3-pyridazinecarboxamide 1H-NMR(400 MHz, DMSO-d6, δppm): 1.16(6H, d, J=6.8 Hz), 2.87(3H,s), 4.42-4.50(1H,m), 7.09(1H, brd, J=8.0 Hz), 7.42-7.47(3H,m), 7.76(1/2H, brs), 7.92(1/2H, brs), 8.30-8.34(3H,m), 8.48(1H, d, J=9.2 Hz), 10.85(1H,brs), 11.08(1/2H, brs), 11.14(1/2H, brs).

EXAMPLE 46

N-{2-[isopropyl(methyl)amino]-1H-benzimidazol-6-yl}-5-(6-methoxy-3-pyridinyl)-2-pyrazinecarboxamide 1H-NMR(400 MHz, DMSO-d6, δppm): 1.16(6H, d, J=6.8 Hz), 2.87(3H,s), 3.95(3H,s), 4.42-4.49(1H,m), 7.02(1H, d, J=8.8 Hz), 7.09(1H, d, J=8.8 Hz), 7.37(1H, d, J=8.0 Hz), 7.82(1H,brs), 8.51(1H, dd, J=8.0, 2.4 Hz), 9.07(1H,s), 9.28(1H,s), 9.33(1H,s), 10.44(1H,brs), 11.17(1H,brs).

EXAMPLE 47

2-(4-Fluorophenyl)-N-{2-[isopropyl(methyl)amino]-1H-benzimidazol-6-yl}-5-pyrimidinecarboxamide 1H-NMR(400 MHz, DMSO-d6, δppm): 1.16(6H, d, J=6.4 Hz), 2.88(3H,s), 4.41-4.48(1H,m), 7.10(1H, d, J=8.4 Hz), 7.22(1H, d, J=8.4 Hz), 7.37-7.41(2H,m), 7.71(1H,brs), 8.49-8.52(2H,m), 9.32(2H,s), 10.37(1H,brs), 11.21(1H,brs).

EXAMPLE 48

1-(4-Fluorophenyl)-N-{2-[isopropyl(methyl)amino]-1H-benzimidazol-6-yl}-4-piperidinecarboxamide 1H-NMR(300 MHz, DMSO-d6, δppm): 1.14(6H, d, J=6.6 Hz), 1.65-1.92(4H,m), 2.38-2.54(1H,m), 2.56-2.74(2H,m), 2.85(3H,s), 3.58-3.73(2H,m), 4.42(1H, septet, J=6.6 Hz), 6.90-7.16(6H,m), 7.53-7.66(1H,m), 9.67(1H,br.s).

EXAMPLE 49

N-{2-[isopropyl(methyl)amino]-1H-benzimidazol-6-yl}-1-phenyl-4-piperidinecarboxamide 1H-NMR(300 MHz, DMSO-d6, δppm): 1.14(6H, d, J=6.6 Hz), 1.64-1.92(4H,m), 2.38-2.53(1H,m), 2.58-2.79(2H,m), 2.84(3H,s), 3.69-3.83(2H,m), 4.42(1H, septet, J=6.6 Hz), 6.68-6.79(1H,m), 7.10-7.25(2H,m), 7.50-7.65(1H,m), 9.66(1H,br.s).

In the following Examples 50-62, the reactions were carried out in the manner similar to Example 2, except that N-isopropylmethylamine which was used in Example 2-(2) was changed to a compound corresponding to the intended product compound in each run.

EXAMPLE 50

2-Methyl-N-{1-[6-({3-[4-(trifluoromethyl)phenyl]propanoyl}-amino)-1H-benzimidazol-2-yl]-3-pyrrolidinyl}propanamide 1H-NMR(400 MHz, DMSO-d6, δppm): 0.98(6H, d, J=7.0 Hz), 1.80-1.92(1H,m), 2.10-2.20(1H,m), 2.30-2.40(1H,m), 2.62(2H, t, J=7.2 Hz), 3.00(2H, t, J=7.2 Hz), 3.42-3.60(2H, m), 3.61-3.70(1H,m), 4.30-4.40(1H,m), 6.92-7.10(2H,m), 7.46(2H, d, J=8.0 Hz), 7.62(2H, d, J=8.0 Hz), 8.04(1H,s), 9.70(1H,s).

EXAMPLE 51

N-{2-[cyclohexyl(methyl)amino]-1H-benzimidazol-6-yl}-3-[4-(trifluoromethyl)phenyl]propanamide 1H-NMR(400 MHz, DMSO-d6, δppm): 1.02-1.18(1H,m), 1.28-1.42(2H,m), 1.42-1.58(2H,m), 1.58-1.70(3H,m), 1.72-1.86(2H,m), 2.62(2H, t, J=7.2 Hz), 2.88(3H,s), 3.00(2H, t, J=7.2 Hz), 3.92-4.04(1H,m), 6.92-7.10(2H,m), 7.48(2H, d, J=8.0 Hz), 7.50-7.60(1H,m), 7.64(2H, d, J=8.0 Hz), 9.70(1H, s).

EXAMPLE 52

N-{2-[ethyl(cyclohexyl)amino]-1H-benzimidazol-6-yl}-3-[4-(trifluoromethyl)phenyl]propanamide 1H-NMR(400 MHz, DMSO-d6, δppm): 1.10-1.24(4H,m), 1.32-1.50(2H,m), 1.50-1.70(3H,m), 1.72-1.86(4H,m), 2.70(2H, t, J=7.2 Hz), 3.00(2H, t, J=7.2 Hz), 3.44-3.60(2H,m), 3.82-3.96(1H,m), 7.30(2H,s), 7.50(2H, d, J=8.0 Hz), 7.64(2H, d, J=8.0 Hz), 7.98(1H,s), 10.22(1H,s).

EXAMPLE 53

N-{2-[methyl(1-methyl-3-pyrrolidinyl)amino]-1H-benzimidazol-6-yl}-3-[4-(trifluoromethyl)phenyl]propanamide 1H-NMR(400 MHz, DMSO-d6, δppm): 1.70-1.84(1H,m), 2.10-2.20(1H,m), 2.30(3H,s), 2.60(2H, t, J=7.2 Hz), 2.70-2.90(2H,m), 2.98(3H,s), 3.00(2H, t, J=7.2 Hz), 4.78-4.88(1H,m), 6.92-7.08(2H,m), 7.42-7.72(5H,m), 9.70(1H,s).

EXAMPLE 54

N-{2-[methyl(1-methyl-4-piperidinyl)amino]-1H-benzimidazol-6-yl}-3-[4-(trifluoromethyl)phenyl]propanamide 1H-NMR(400 MHz, DMSO-d6, δppm): 1.94-2.10(2H,m), 2.20-2.34(2H,m), 2.70(2H, t, J=7.2 Hz), 3.76(3H,s), 3.00(2H, t, J=7.2 Hz), 3.08(3H,s), 3.08-3.14(2H,m), 3.50-3.60(2H,m), 4.32-4.42(1H,m), 7.34(2H,s), 7.50(2H, d, J=8.0 Hz), 7.64(2H, d, J=8.0 Hz), 7.98(1H,s), 10.22(1H,s).

EXAMPLE 55

N-{2-[cyclopropyl(methyl)amino]-1H-benzimidazol-6-yl}-3-[4-(trifluoromethyl)phenyl]propylanamide 1H-NMR(400 MHz, DMSO-d6, δppm): 0.66(2H,s), 0.84(2H,s), 2.54-2.70(2H,m), 2.96-3.10(2H,m), 3.00(3H,s), 6.94-7.10(2H,m), 7.50(2H, d, J=8.0 Hz), 7.64(2H, d, J=8.0 Hz), 7.8(1H,s).

EXAMPLE 56

N-{2-[cyclcobutyl(methyl)amino]-1H-benzimidazol-6-yl}-3-[4-(trifluoromethyl)phenyl]propanamide 1H-NMR(400 MHz, DMSO-d6, δppm): 1.52-1.70(2H,m), 2.02-2.24(4H,m), 2.60(2H, t, J=7.2 Hz), 2.96(3H,s), 3.00(2H, t, J=7.2 Hz), 4.52-4.70(1H,m), 6.90-7.10(2H,m), 7.50(2H, d, J=8.0 Hz), 7.64(2H, d, J=8.0 Hz), 9.60-9.78(1H,m).

EXAMPLE 57

N-{2-[cyclopentyl(methyl)amino]-1H-benzimidazol-6-yl}-3-[4-(trifluoromethyl)phenyl]propanamide 1H-NMR(400 MHz, CDCl3, δppm): 1.60-2.00(8H, m), 2.66(2H, t, J=7.2 Hz), 2.98(3H,s), 3.10(2H, t, J=7.2 Hz), 4.42-4.58(1H,m), 6.92-7.02(1H,m), 7.08-7.16(1H,m), 7.44(2H, d, J=8.0 Hz), 7.50-7.68(3H,m).

EXAMPLE 58

N-{2-[(1-acetyl-3-pyrrolidinyl)(methyl)amino]-1H-benzimidazol-6-yl}-3-[4-(trifluoromethyl)phenyl]propanamide 1H-NMR(400 MHz, CDCl3, δppm): 2.00(3H,s), 2.10-2.24(2H,m), 2.62(2H, t, J=7.2 Hz), 3.00(3H,s), 3.04(2H, t, J=7.2 Hz), 3.30-3.60(2H,m), 3.62-3.80(2H,m), 4.72-4.86(1H,m), 6.96-7.00(1H,m), 7.08-7.16(1H,m), 7.40(2H, d, J=8.0 Hz), 7.50-7.62(3H,m).

EXAMPLE 59

N-{2-[methyl(tetrahydro-3-furanyl)amino]-1H-benzimidazol-6-yl}-3-[4-(trifluoromethyl)phenyl]propanamide ¹H-NMR(400 MHz, DMSO-d6, δppm): 1.87-1.95(1H,m), 2.12-2.21(1H,m), 2.63(2H, t, J=7.2 Hz), 2.99(2H, t, J=7.2 Hz), 3.25-3.35(1H,m), 3.61(1H, q, J=5.8 Hz), 3.70-3.75(1H,m), 3.90-3.98(1H,m), 4.90-4.98(1H,m), 6.92-7.05(2H,m), 7.60-7.70(1H,m), 7.47(2H, d, J=7.6 Hz), 7.63(2H, d, J=7.6 Hz), 9.71(1H,s).

EXAMPLE 60

N-{2-[1-isobutyryl-3-pyrrolidinyl(methyl)amino]-1H-benzimidazol-6-yl}-3-[4-(trifluoromethyl)phenyl]propanamide 1H-NMR(300 MHz, DMSO-d6, δppm): 1.00(6H, d, J=6.8 Hz), 2.00-2.20(2H,m), 2.63(2H, t, J=7.2 Hz), 2.63-2.75(1H, m), 2.97(3H,s), 2.98(2H, t, J=7.2 Hz), 3.20-3.40(1H,m), 3.42-3.80(3H,m), 4.70-4.90(1H,m), 6.98-7.10(2H,m), 7.48 (2H, d, J=8.0 Hz), 7.63(3H, d, J=8.0 Hz), 9.74(1H,s).

EXAMPLE 61

N-{2-[methyl(1-methyl-3-oxo-3-pyrrolidinyl)amino]-1H-benzimidazol-6-yl}-3-[4-(trifluoromethyl)phenyl]propanamide 1H-NMR(400 MHz, DMSO-d6, δppm): 1.98-2.10(1H,m), 2.20-2.34(1H,m), 2.62(2H, t, J=7.2 Hz), 2.77(3H,s), 2.83 (3H,s), 3.00(2H, t, J=7.2 Hz), 3.26-3.40(2H,m), 4.98-5.08 (1H,m), 6.96-7.06(2H,m), 7.47(2H, d, J=8.0 Hz), 7.62(2H, d, J=8.0 Hz), 9.70(1H,brs).

EXAMPLE 62

N-{2-[methyl(1-methyl-5-oxo-3-pyrrolidinyl)amino]-1H-benzimidazol-6-yl}-3-[4-(trifluoromethyl)phenyl]propanamide 1H-NMR(400 MHz, CD3OD, δppm): 2.52-2.62(1H,m), 2.70(2H, t, J=7.2 Hz), 2.78-2.87(1H,m), 2.90(3H,s), 3.29 (3H,s), 3.10(2H, t, J=7.2 Hz), 3.50-3.58(1H,m), 3.78-3.88 (1H,m), 4.96-5.04(1H,m), 6.98-7.06(1H,m), 7.16(1H, d, J=8.0 Hz), 7.44(2H, d, J=8.0 Hz), 7.57(2H, d, J=8.0 Hz), 7.62(1H,brs).

In the following Examples 63-64, the reactions were carried out in the manner similar to Example 2, except that N-isopropylmethylamine which was used in Example 2-(2) and 3-[4-(trifluoromethyl)phenyl]propionic acid which was used in Example 2-(3) were each replaced with a starting material corresponding to the intended product compound.

EXAMPLE 63

N-{2-[1-acetyl-3-pyrrolidinyl(methyl)amino]-1H-benzimidazol-6-yl}-5-(4-fluorophenyl)-2-pyridinecarboxamide 1H-NMR(400 MHz, DMSO-d6, δppm): 1.96(3H,s), 2.00-2.20(2H,m), 3.00(3H,s), 3.20-3.74(4H,m), 4.78-4.98(1H,m), 7.12(1H, d, J=8.0 Hz), 7.34-7.46(3H,m), 7.82-7.96(3H,m), 8.20(1H, d, J=8.0 Hz), 8.30(1H, d, J=6.0 Hz), 9.00(1H,s), 10.42(1H,s).

EXAMPLE 64

N-{2-[1-acetyl-3-pyrrolidinyl(methyl)amino]-1H-benzimidazol-6-yl}-5-(4-fluorophenyl)-2-pyrazinecarboxamide 1H-NMR(400 MHz, DMSO-d6, δppm): 2.00(3H,s), 2.00-2.36(2H,m), 3.10(3H,s), 3.20-3.86(4H,m), 4.60-4.84(1H,m), 7.30-7.50(3H,m), 7.74(1H, d, J=8.0 Hz), 8.18(1H,s), 8.28-8.38(2H,m), 9.30(1H,s), 9.36(1H,s).

In the following Examples 65-87, the reactions were carried out in the manner similar to Example 1, except that 2-chloro-6-nitrobenzimidazole which was used in Example 1-(1) was replaced with 2-chloro-1-methyl-6-nitro-1H-benzimidazole, and N-isopropylmethylamine used in said Example 1-(1) was changed to a starting material corresponding to the intended product compound in each run; and that also 3-[4-(trifluoromethyl)phenyl]propionic acid which was used in Example 1-(2) was changed to a starting material corresponding to the intended product compound in each run.

EXAMPLE 65

N-{2-[ethyl(methyl)amino]-1-methyl-1H-benzimidazol-6-yl}-3-[4-(trifluoromethyl)phenyl]propanamide 1H-NMR(300 MHz, DMSO-d6, δppm): 1.14(3H, t, J=7.2 Hz), 2.66(2H, t, J=7.3 Hz), 2.86(3H,s), 3.01(2H, t, J=7.3 Hz), 3.22(2H, q, J=7.2 Hz), 3.52(3H,s), 7.04(1H, d, J=8.5 Hz), 7.25(1H, d, J=8.5 Hz), 7.49(2H, d, J=7.9 Hz), 7.64(2H, d, J=7.9 Hz), 7.76(1H,s).

EXAMPLE 66

N-[2-(dimethylamino)-1-methyl-1H-benzimidazol-6-yl}-3-[4-(trifluoromethyl)phenyl]propanamide 1H-NMR(300 MHz, DMSO-d6, δppm): 2.66(2H, t, J=7.5 Hz), 2.87(6H, s), 3.01(2H, t, J=7.5 Hz), 3.54(3H,s), 7.04(1H, d, J=8.4 Hz), 7.25(1H, d, J=8.4 Hz), 7.49(2H, d, J=8.0 Hz), 7.64(2H, d, J=8.0 Hz), 7.74(1H,s), 9.86(1H,s).

EXAMPLE 67

N-{2-[isopropyl(methyl)amino]-1-methyl-1H-benzimidazol-6-yl}-3-[4-(trifluoromethyl)phenyl]propanamide 1H-NMR(300 MHz, DMSO-d6, δppm): 1.28(6H, d, J=6.6 Hz), 2.73(2H, t, J=7.6 Hz), 3.02(2H, t, J=7.6 Hz), 3.06(3H,s), 3.69(3H,s), 4.14(1H,m), 7.36(1H, d, J=8.6 Hz), 7.42(1H, d, J=8.6 Hz), 7.50(2H, d, J=8.0H), 7.64(2H, d, J=8.0 Hz), 8.03 (1H,s), 10.41(1H,s).

EXAMPLE 68

N-[1-methyl-2-(1-pyrrolidinyl)-1H-benzimidazol-6-yl}-3-[4-(trifluoromethyl)phenyl]propanamide 1H-NMR(300 MHz, CDCl3, δppm): 2.00(4H,m), 2.69(2H, t, J=7.5 Hz), 3.13(2H, t, J=7.5 Hz), 3.62(7H,brs), 6.73(1H, brd, J=8.6 Hz), 7.34(3H,m), 7.54(2H, d, J=7.9 Hz), 7.82(1H,s),

EXAMPLE 69

N-{2-[methyl(propyl)amino]-1-methyl-1H-benzimidazol-6-yl}-3-[4-(trifluoromethyl)phenyl]propanamide 1H-NMR(300 MHz, DMSO-d6, δppm): 0.87(3H, t, J=7.4 Hz), 1.59(2H,m), 2.65(2H,m), 2.86(3H,s), 3.01(2H, t, J=7.5 Hz), 3.13(2H, t, J=7.5 Hz), 3.53(3H,s), 7.02(1H, d, J=8.5 Hz), 7.23(1H, d, J=8.5 Hz), 7.48(2H, d, J=8.2 Hz), 7.64(2H, d, J=8.2 Hz), 7.74(1H,s), 9.85(1H,s).

EXAMPLE 70

N-[1-methyl-2-(1-pyrrolidinyl)-1H-benzimidazol-6-yl]-2-[4-(trifluoromethyl)phenoxy]acetamide 1H-NMR(300 MHz, DMSO-d6, δppm): 1.87(4H,m), 3.53(4H,m), 3.59(3H,s), 4.80(2H,s), 7.10(1H, d, J=8.3 Hz), 7.19(3H,m), 7.69(3H,m), 10.03(1H,s).

EXAMPLE 71

N-[1-methyl-2-(1-piperidinyl)-1H-benzimidazol-6-yl}-3-[4-(trifluoromethyl)phenyl]propanamide 1H-NMR(300 MHz, CHCl3, δppm): 1.57-1.87(6H,m), 2.69(2H, t, J=7.5 Hz), 3.13(2H, t, J=7.5 Hz), 3.16-3.22(4H, m), 3.56(3H,s), 6.76(1H, d, J=8.4 Hz), 7.34(2H, d, J=8.4 Hz), 7.42(2H, d, J=8.4 Hz), 7.52(1H,br.s), 7.54(2H, d, J=8.4 Hz), 7.90(1H,br.s).

EXAMPLE 72

N-[2-(1-azepanyl)-1-methyl-1H-benzimidazol-6-yl}-3-[4-(trifluoromethyl)phenyl]propanamide 1H-NMR(300 MHz, CHCl3, δppm): 1.64-1.92(8H, m), 2.68(2H, t, J=7.5 Hz), 3.12(2H, t, J=7.5 Hz), 3.46-3.58(4H, m), 3.58(3H,s), 6.69-6.85(1H,m), 7.30-7.42(1H,m), 7.36(2H, d, J=7.8 Hz), 7.48(1H,br.s), 7.54(2H, d, J=7.8 Hz), 7.84(1H,br.s).

EXAMPLE 73

N-(2-{3-[acetyl(methyl)amino]-1-pyrrolidinyl}-1-methyl-1H-benzimidazol-6-yl}-3-[4-(trifluoromethyl)phenyl]propanamide 1H-NMR(300 MHz, DMSO-d6, δppm): 2.01(5H,m), 2.66(2H, t, J=7.5 Hz), 2.78(6/5H, s), 2.93(9/5H, s), 3.01(2H, t, J=7.5 Hz), 3.55(4H,m), 3.59(3H,s), 4.62(2/5H, m), 5.14(3/5H, m), 7.02(1H, d, J=8.4 Hz), 7.19(1H, d, J=8.4 Hz), 7.49(2H, d, J=8.2 Hz), 7.64(2H, d, J=8.2 Hz), 7.72(1H,brs), 9.84(1H,s).

EXAMPLE 74

N-(2-{3-[isobutyryl(methyl)amino]-1-pyrrolidinyl}-1-methyl-1H-benzimidazol-6-yl}-3-[4-(trifluoromethyl)phenyl]propanamide 1H-NMR(300 MHz, DMSO-d6, δppm): 1.02(6H, d, J=4.0 Hz), 2.10(3H,m), 2.66(2H, t, J=7.5 Hz), 2.79(1.2H,s), 2.85(1H,m), 2.98(1.8H,s), 3.01(2H, t, J=7.5 Hz), 3.59(3H,s), 3.54(4H, m), 4.78(2/5H,m), 5.15(3/5H, m), 7.00(1H, brd, J=8.5 Hz), 7.18(1H, d, J=8.5 Hz), 7.49(2H, d, J=8.2 Hz), 7.64(2H, d, J=8.2 Hz), 7.71(1H,brs), 9.83(1H,s).

EXAMPLE 75

N-(2-{3-[methanesulfonyl(methyl)amino]-1-pyrrolidinyl}-1-methyl-1H-benzimidazol-6-yl}-3-[4-(trifluoromethyl)phenyl]propanamide hydrochloride The reaction was carried out following Example 2, and the product as obtained was treated with 4N hydrochloric acid-ethyl acetate to provide the title compound.

1H-NMR(300 MHz, DMSO-d6, δppm): 2.20(2H,m), 2.72(2H, t, J=7.5 Hz), 2.82(3H,s), 3.00(5H,m), 3.79(3H,s), 3.86(4H,m), 4.55(1H,m), 7.33(1H, brd, J=8.6 Hz), 7.38(1H, d, J=8.6 Hz), 7.50(2H, d, J=8.1 Hz), 7.64(2H, d, J=8.1 Hz), 8.00(1H,brs), 10.40(1H,brs).

EXAMPLE 76

N-{2-[cyclohexyl(methyl)amino]-1-methyl-1H-benzimidazol-6-yl}-3-[4-(trifluoromethyl)phenyl]propanamide 1H-NMR(300 MHz, DMSO-d6, δppm): 1.04-1.69(6H,m), 1.69-1.80(4H,m), 2.66(2H, t, J=7.5 Hz), 2.76(3H,s), 3.01(2H, t, J=7.5 Hz), 3.51(3H,s), 7.03(1H, d, J=8.4 Hz), 7.40(2H, d, J=8.4 Hz), 7.49(1H, d, J=8.4 Hz), 7.64(1H, d, J=8.4 Hz), 7.74(1H,s), 9.85(1H,s).

EXAMPLE 77

N-[1-methyl-2-(1-pyrrolidinyl)-1H-benzimidazol-6-yl]-3-(4-bromophenyl)propanamide 1H-NMR(300 MHz, DMSO-d6, δppm): 1.89(4H,m), 2.59(2H, t, J=7.6 Hz), 2.89(2H, t, J=7.6 Hz), 3.52(4H,m), 3.58(3H,s), 7.00(1H, d, J=8.4 Hz), 7.13(1H, d, J=8.4 Hz), 7.22(2H, d, J=8.4 Hz), 7.46(2H, d, J=8.4 Hz), 7.66(1H,s), 9.78(1H,s).

EXAMPLE 78

N-[1-methyl-2-(1-pyrrolidinyl)-1H-benzimidazol-6-yl]-5-(4-fluorophenyl)-2-pyrazinecarboxamide 1H-NMR(300 MHz, DMSO-d6, δppm): 1.90(4H,m), 3.57(4H,m), 3.65(3H,s), 7.22(1H, d, J=8.4 Hz), 7.44(3H,m), 7.94(1H, d, J=1.8 Hz), 8.33(2H,m), 9.32(1H, d, J=1.5 Hz), 9.34(1H, d, J=1.5 Hz), 10.56(1H,s).

EXAMPLE 79

N-[1-methyl-2-(11-pyrrolidinyl)-1H-benzimidazol-6-yl]-2-(4-chlorophenoxy)acetamide 1H-NMR(300 MHz, DMSO-d6, δppm): 1.89(4H,m), 3.53(4H,m), 3.59(3H,s), 4.69(2H,s), 7.03(2H, d, J=9.0), 7.12(2H, m), 7.36(2H, d, J=9.0 Hz), 7.67(1H,s), 9.96(1H,s).

EXAMPLE 80

N-{2-[2-methyl-1-pyrrolidinyl]-1-methyl-1H-benzimidazol-6-yl}-3-[4-(trifluoromethyl)phenyl]propanamide 1H-NMR(400 MHz, CDCl3, δppm): 1.23(3H, d, J=5.6 Hz), 1.58-1.68(1H,m), 1.95-2.04(1H,m), 2.15-2.24(1H,m), 2.68(2H, t, J=7.2 Hz), 3.13(2H, t, J=7.2 Hz), 3.35-3.39(1H, m), 3.48(3/5H, s), 3.58(12/5H, s), 3.73-3.79(1H,m), 4.19-4.28(1H,m), 6.70(1H, d, J=8.4 Hz), 7.34-7.37(3H,m), 7.53 (2H, d, J=8.0 Hz), 7.80(1H, d, J=5.6 Hz).

EXAMPLE 81

N-[1-methyl-2-(1-pyrrolidinyl)-1H-benzimidazol-6-yl}-3-[4-(trifluoromethyl)phenyl]propanamide 1H-NMR(400 MHz, CDCl3, δppm): 2.44(2H, dt, J1=J2=7.6 Hz), 2.68(2H, t, J=7.2 Hz), 3.13(2H, t, J=7.2 Hz), 3.48(3/2H, s), 3.51(3/2H, s), 4.24(4H, t, J=7.6 Hz), 6.69(1H, dd, J=8.0, 1.6 Hz), 7.18(1H,brs), 7.34(3H, d, J=8.0 Hz), 7.53 (2H, d, J=8.0 Hz), 7.78(1H, d, J=1.6 Hz).

EXAMPLE 82

N-{2-[1-acetyl-3-pyrrolidinyl(methyl)amino]-1-methyl-1H-benzimidazol-6-yl}-3-[4-(trifluoromethyl)phenyl]propanamide 1H-NMR(300 MHz, CDCl3, δppm): 1.93-2.39(5H,m), 2.71(2H, t, J=8.4 Hz), 2.80-2.91(3H,m), 3.15(2H, t, J=8.4 Hz), 3.27-4.32(8H,m), 6.72-6.87(1H,m), 7.25-7.38(1H,m), 7.37(2H, d, J=8.4 Hz), 7.40-7.52(1H,m), 7.57(2H, d, J=8.4 Hz), 7.94(1H,br.s).

EXAMPLE 83

N-{2-[1-isobutyryl-3-pyrrolidinyl(methyl)amino]-1-methyl-1H-benzimidazol-6-yl}-3-[4-(trifluoromethyl)phenyl]propanamide 1H-NMR(300 MHz, CDCl3, δppm): 1.00-1.16(6H,m), 1.90-2.39(2H,m), 2.46-2.76(3H,m), 2.79-2.92(3H,m), 3.08-3.20(2H,m), 3.33-4.18(8H, m), 6.74-6.84(1H,m), 7.33(1H, s), 7.37(2H, d, J=8.4 Hz), 7.41-7.53(1H,m), 7.56(2H, d, J=8.4 Hz), 7.94(1H,br.s).

EXAMPLE 84

N-(2-{3-[methanesulfonyl(methyl)amino]-1-pyrrolidinyl}-1-methyl-1H-benzimidazol-6-yl})-2-[4-(trifluoromethyl)phenoxy]-acetamide 1H-NMR(300 MHz, DMSO-d6, δppm): 2.08(2H,m), 2.80 (3H,s), 2.95(3H,s), 3.51-3.71(4H,m), 3.61(3H,s), 4.48(1H, m), 4.81(2H,s), 7.17(4H,m), 7.70(3H,m), 10.06(1H,s).

EXAMPLE 85

N-(2-{3-[acetyl(methyl)amino]-1-pyrrolidinyl}-1-methyl-1H-benzimidazol-6-yl}-2-[4-(trifluoromethyl)phenoxy]-acetamide 1H-NMR(300 MHz, DMSO-d6, δppm): 2.05(5H,m), 2.79 (1.2H,s), 2.93(1.8H,s), 3.56(4H,m), 3.61(3H,s), 4.62(0.4H, m), 4.81(2H,s), 5.12(0.6H,m), 7.16(4H,m), 7.70(3H,m), 10.06(1H,s).

EXAMPLE 86

N-{2-[3-(hydroxymethyl)1-pyrrolidinyl]-1-methyl-1H-benzimidazol-6-yl}-3-[4-(trifluoromethyl)phenyl]propanamide 1H-NMR(300 MHz, CHCl3, δppm): 1.70-1.88(1H,m), 2.03-2.14(1H,m), 2.43-2.61(1H,m), 2.70(2H, t, J=7.5 Hz), 3.12(2H, t, J=7.5 Hz), 3.49(3H,s), 3.45-3.78(6H,m), 6.72-6.82(1H,m), 7.23-7.65(6H,m), 7.68(1H,br.s).

EXAMPLE 87

5-(4-Fluorophenyl)-N-{2-[isopropyl(methyl)amino]-1-methyl-1H-benzimidazol-6-yl}-2-pyrimidinecarboxamide 1H-NMR(300 MHz, DMSO-d6, δppm): 1.18(6H, d, J=6.6 Hz), 2.76(3H,s), 3.57(3H,s), 3.82(1H,m), 7.33(1H, d, J=8.5 Hz), 7.41-7.49(2H,m), 7.45(1H, d, J=8.5 Hz), 8.00(3H,m), 9.34(2H,s), 10.69(1H,s).

In the following Examples 88 and 89, the reactions were carried out in the manner similar to Example 3, except that 4-(4-fluorophenyl)piperidine hydrochloride which was used in Example 3-(3) was replaced with a starting material corresponding to the intended product compound in each run.

EXAMPLE 88

1-(4-Fluorophenyl)-N-{2-[isopropyl(methyl)amino]-1H-benzimidazol-6-yl}-4-piperazinecarboxamide 1H-NMR(300 MHz, CDCl3, δppm): 1.17(6H, d, J=6.6 Hz), 2.88(3H,s), 3.12(4H, br.t, J=4.8 Hz), 3.67(4H, br.t, J=4.8 Hz), 4.41(1H, septet, J=6.6 Hz), 6.80-7.02(5H,m), 7.04-7.14 (1H,m), 7.21-7.44(1H,m).

EXAMPLE 89

N-{2-[isopropyl(methyl)amino]-1H-benzimidazol-6-yl}-1-phenyl-4-piperazinecarboxamide 1H-NMR(300 MHz, CDCl3, δppm): 1.14(6H, d, J=6.6 Hz), 2.83(3H,s), 3.21(4H, br.t, J=4.8 Hz), 3.68(4H, br.t, J=4.8 Hz), 4.38(1H, septet, J=6.6 Hz), 6.77-7.01(5H,m), 7.03-7.12 (1H,m), 7.20-7.43(1H,m).

TEST EXAMPLES

Utility of compounds of the present invention is verified, for example, by the following pharmacological test examples.

Pharmacological Test Example 1

MCH Binding Inhibition Assay cDNA sequence encoding human MCH-1R [FEBS Letters, 398:253(1996), Biochimica et Biophisica Acta, 1401: 216(1998)] was cloned into plasmid vector pEF/mic/cyto (Invitrogen). The expression vector so obtained was transfected into host cells CHO-K1 (American Type Culture Collection) by using Lipofectamine Plus Reagent (Life Technologies) to give MCH-1R expressing cells.

Membrane preparation generated from the cells expressing MCH-1R was incubated together with a test compound and 50 pM [$^{125}$I]MCH (NEN) in assay buffer (50 mM Tris buffer, pH7.4, containing 10 mM magnesium chloride, 2 mM ethylenediaminetetraacetic acid, 0.01% Bacitracin and 0.2% bovine serum albumin) at 25° C. for 1 hour, then filtered through a glass filter GF/C (Whatman). After washing the glass filter with 50 mM Tris buffer, pH7.4, containing 10 mM magnesium chloride, 2 mM ethylenediaminetetraacetic acid and 0.04% Tween-20, radioactivity on the glass filter was measured. Nonspecific binding was measured in the presence of 1 μM human MCH and a 50% inhibitory concentration ($IC_{50}$) of the test compound against specific [$^{125}$I]MCH-binding was determined. The results are shown in Table 1.

TABLE 1

50% Inhibitory Concentration against MCH-Binding

| Test Compound | $IC_{50}$ (nM) |
|---|---|
| Example 1 | 5.8 |
| Example 17 | 6.2 |
| Example 24 | 3.3 |
| Example 34 | 8.8 |

As above, compounds of the present invention potently inhibit binding of MCH to MCH-1R, and act as MCH-1R antagonists.

Pharmacological Test Example 2

Study of Antagonistic Effect Against MCH-Induced Feeding Behavior

Male SD rats (9-12 weeks old) were anesthetized with ketamine and xylazine (74 and 11 mg/kg, single intra-peritoneal injection). A permanent guide cannula (26-gauge) was stereotaxically implanted into the third ventricle and fixed with dental resin. The position of the tip of guide cannula was 2.2 mm posterior to the bregma, on the mid line and 8.0 mm ventral from the surface of the skull. After 2-week recovery period, rats were fed high fat diet for about 4 hours for satiation. Then an internal cannula (33 gauge) connected to a micro-syringe was inserted to the guide cannula and melanin concentrating hormone (MCH, 5 μg/1 μL/head, dissolved in artificial cerebrospinal fluid) was administered to the third ventricle. One hour before the administration of MCH, rats were orally treated with a compound of example 24(10 or 30 mg/kg), which was suspended in 0.5% aqueous methylcellulose solution. Then rats were given high fat diet and food intake for 2 hours after MCH administration was measured.

FIG. 1 shows the rats' food intake for 2 hours following said third ventricular administration of MCH an hour after said oral administration of the compound of the present invention to the rats which had been fed high fat diet to satiation. That is, the rats' two hours' food intake (g) 1) when said Example 24 compound was not administered, 2) when Example 24 compound was administered at a dose of 10 mg/kg, and 3) when Example 24 compound was administered at a dose of 30 mg/kg are shown.

As illustrated by FIG. 1, the compound of the present invention dose-dependently and significantly inhibited the increase in feed intake induced by the third ventricularly administered MCH. Furthermore, the result of administering artificial cerebrospinal fluid (aCSF) alone in place of MCH and the compound of the present invention is shown as the reference.

INDUSTRIAL APPLICABILITY

Compounds of the present invention exhibit MCH-1R antagonistic action and are useful as preventing or treating agents of metabolic disorders represented by obesity, diabetes, hormone disorder, hyperlipidemia, gout, fatty liver, hepatitis and cirrhosis; cardiovascular disorders represented by stenocardia, acute or congestive heart failure, myocardial infarction, coronary atherosclerosis, hypertension, renal diseases and electrolyte abnormality; central nervous system or peripheral nervous system disorders represented by bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence and alcoholism; reproductive disorders represented by infertility, preterm labor and sexual dysfunction; digestive disorders; respiratory disorders; cancer or pigmentation, in particular, as preventing or treating agent of obesity.

The invention claimed is:

1. An antagonist to melanin-concentrating hormone receptor comprising as the active ingredient a benzimidazole derivative represented by the following formula [I]

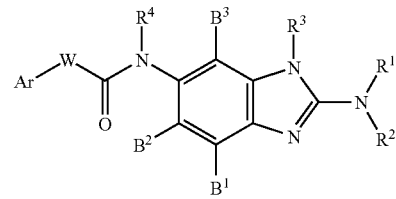

[I]

wherein:
$B^1$, $B^2$ and $B^3$ are same or different and each stands for hydrogen, halogen, lower alkyl or lower alkyloxy;
$R^1$ and $R^2$ are same or different and each stands for
1) hydrogen,
2) a 3-10 membered aliphatic ring group of the formula [A]

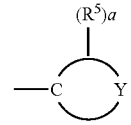

[A]

wherein $R^5$ either stands for a substituent selected from later specified Group α, or two $R^5$'s together form oxo group; Y stands for —$CH_2$—, —$NR^6$— or —O—; $R^6$ stands for a substituent selected from the group consisting of hydrogen, optionally fluorine-substituted lower alkyl, lower alkylcarbonyl, lower alkyloxycarbonyl, lower alkylsulfonyl, carbamoyl, mono-lower alkylcarbamoyl and di-lower alkylcarbamoyl; and a is an integer of 0-4, or 3) a lower alkyl group which optionally has substituent(s) selected from Group α or a 3-10 membered aliphatic ring group represented by the formula [A], provided $R^1$ and $R^2$ are not hydrogen atoms at the same time;

$R^3$ stands for hydrogen or a lower alkyl which optionally has substituents selected from Group α;

$R^4$ stands for hydrogen or a lower alkyl;

W is a divalent group which stands for a mono- or bi-cyclic, 3-8 membered aromatic heterocycle wherein if the heterocycle is a pyrazole ring, the pyrazole ring may be substituted by methyl; and Ar stands for mono- or bi-cyclic, aromatic carbocycle, optionally having one, two or more substitutents selected from Group β;

wherein Group α represents halogen, hydroxyl, amino, mono-lower alkylamino, di-lower alkylamino, optionally fluorine-substituted lower alkyloxy, lower alkyloxycarbonyl, (lower alkyloxycarbonyl)amino, (lower alkyloxycarbonyl)lower alkylamino, lower alkylcarbonyl, lower alkylcarbonyloxy, (lower alkylcarbonyl)amino, (lower alkylcarbonyl) lower alkylamino, carbamoyl, mono-lower alkylcarbamoyl, di-lower alkylcarbamoyl, carbamoylamino, mono-lower alkylcarbamoylamino, di-lower alkylcarbamoylamino, (mono-lower alkylcarbamoyl)lower alkylamino, (di-lower alkylcarbamoyl)lower alkylamino, carbamoyloxy, mono-lower alkylcarbamoyloxy, di-lower alkylcarbamoyloxy, lower alkylsulfonyl, lower alkylsulfonylamino, sulfamoyl, mono-lower alkylsulfamoyl, di-lower alkylsulfamoyl, sulfamoylamino, (mono-lower alkylsulfamoyl)amino, (di-lower alkylsulfamoyl)amino, (mono-lower alkylsufamoyl)lower alkylamino or (di-lower alkylsulfamoyl)lower alkylamino;

wherein Group β represents halogen, hydroxyl, amino, cyano, mono-lower alkylamino, di-lower alkylamino, optionally fluorine-substituted lower alkyl, optionally fluorine-substituted lower alkyloxy, lower alkyloxycarbonyl, (lower alkyloxycarbonyl)amino, (lower alkyloxycarbonyl)lower alkylamino, carboxyl, lower alkylcarbonyl, lower alkylcarbonyloxy, (lower alkylcarbonyl) amino, (lower alkylcarbonyl)lower alkylamino, di-lower alkylcarbamoyl, di-lower alkylcarbamoylamino, (di-lower alkylcarbamoyl)lower alkylamino, di-lower alkylcarbamoyloxy, lower alkylsulfonyl, lower alkylsufonylamino, di-lower alkylsulfamoyl, sulfamoylamino, (di-lower alkylsulfamoyl) amino, (di-lower alkylsulfamoyl)lower alkylamino, or 5-6 membered aliphatic carbocycle or heterocycle which is optionally substituted with a group selected from group γ; and wherein Group γ represents lower alkylcarbonyl, lower alkylsulfonyl or lower alkyloxycarbonyl;

or a pharmaceutically acceptable salt thereof.

2. The antagonist to melanin-concentrating hormone receptor as described in claim 1, wherein R¹ is methyl.

3. The antagonist to melanin-concentrating hormone receptor as described in claim 2, wherein R² is selected from the group consisting of isopropyl, cyclopropyl, cyclobutyl, cyclopentyl, cyclohexyl, N-methylpyrrolidin-3-yl, N-acetylpyrrolidin-3-yl, N-methylpiperidin-4-yl, tetrahydrofuran-2-yl, 1-methanesulfonylpyrrolidin-3-yl and 1-(isopropylcarbonyl)pyrrolidin-3-yl.

4. The antagonist to melanin-concentrating hormone receptor as described in claim 1, wherein all of B¹, B² and B³ are hydrogen atoms.

5. The antagonist to melanin-concentrating hormone receptor as described in claim 1, wherein R³ is hydrogen or methyl.

6. The antagonist to melanin-concentrating hormone receptor as described in claim 1, wherein R⁴ is hydrogen or methyl.

7. The antagonist to melanin-concentrating hormone receptor as described in claim 1, wherein W is a mono- or bi-cyclic, 3-8 membered aromatic nitrogen-containing heterocycle wherein if the heterocycle is a pyrazole ring, the pyrazole ring may be substituted by methyl.

8. The antagonist to melanin-concentrating hormone receptor as described in claim 7, wherein W is selected from the group consisting of the following substituents:

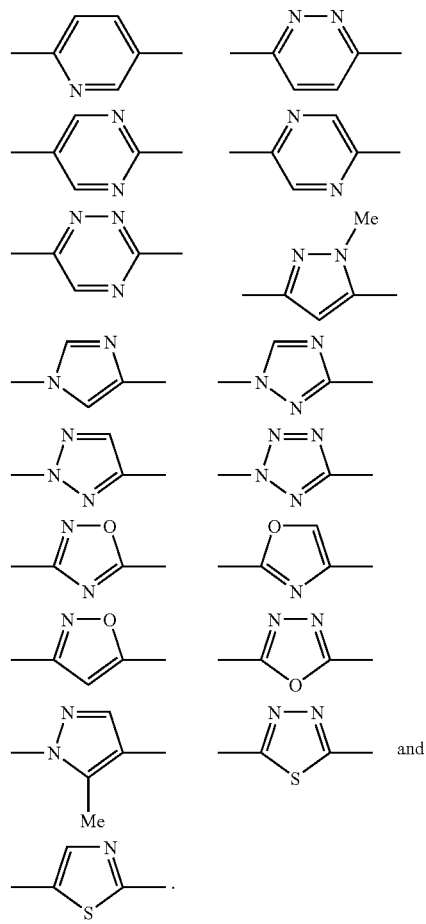

9. The antagonist to melanin-concentrating hormone receptor as described in claim 7, wherein W is selected from the group consisting of the following substituents:

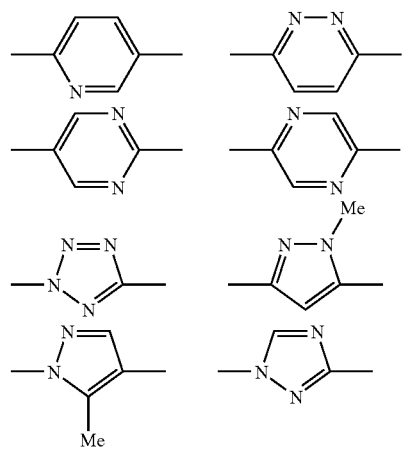

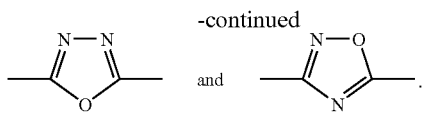 and

10. The antagonist to melanin-concentrating hormone receptor as described in claim 1, wherein Ar is selected from the group consisting of phenyl, 2-fluorophenyl, 3-fluorophenyl, 4-fluorophenyl, 2-trifluoromethylphenyl, 3-trifluoromethylphenyl, 4-trifluoromethylphenyl, 4-methoxyphenyl, 4-methanesulphonylphenyl, 3-fluoro-4-methoxyphenyl, 3,4-difluorophenyl, 2,4-difluorophenyl, 4-chlorophenyl, 4-(piperidin-1-yl)phenyl and 4-(morpholin-1-yl)phenyl.

11. A compound represented by the formula [I-1]

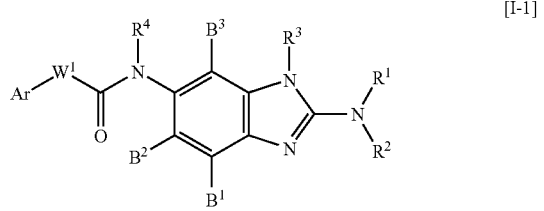

wherein:
$B^1$, $B^2$ and $B^3$ are same or different and each stands for hydrogen, halogen, lower alkyl or lower alkyloxy;
$R^1$ and $R^2$ are same or different and each stands for
1) hydrogen,
2) a 3-10 membered aliphatic ring group of the formula [A]

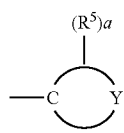

wherein $R^5$ either stands for a substituent selected from later specified Group α, or two $R^5$'s together form oxo group; Y stands for —$CH_2$—, —$NR^6$— or —O—; $R^6$ stands for a substituent selected from the group consisting of hydrogen, optionally fluorine-substituted lower alkyl, lower alkylcarbonyl, lower alkyloxycarbonyl, lower alkylsulfonyl, carbamoyl, mono-lower alkylcarbamoyl and di-lower alkylcarbamoyl; and a is an integer of 0-4, or
3) a lower alkyl group which optionally has substituent(s) selected from Group α or a 3-10 membered aliphatic ring group represented by the formula [A],
provided $R^1$ and $R^2$ are not hydrogen atoms at the same time;
$R^3$ stands for hydrogen or a lower alkyl which optionally has substituents selected from Group α;
$R^4$ stands for hydrogen or a lower alkyl;
$W^1$ is a divalent group which stands for optionally substituted a mono- or bi-cyclic, 3-8 membered aromatic or aromatic heterocycle wherein if the heterocycle is a pyrazole ring, the pyrazole ring may be substituted by methyl; and
Ar stands for, mono- or bi-cyclic, aromatic carbocycle, optionally having one, two or more substitutents selected from Group β;

wherein Group α represents halogen, hydroxyl, amino, mono-lower alkylamino, di-lower alkylamino, optionally fluorine-substituted lower alkyloxy, lower alkyloxycarbonyl, (lower alkyloxycarbonyl)amino, (lower alkyloxycarbonyl)lower alkylamino, lower alkylcarbonyl, lower alkylcarbonyloxy, (lower alkylcarbonyl)amino, (lower alkylcarbonyl) lower alkylamino, carbamoyl, mono-lower alkylcarbamoyl, di-lower alkylcarbamoyl, carbamoylamino, mono-lower alkylcarbamoylamino, di-lower alkylcarbamoylamino, (mono-lower alkylcarbamoyl)lower alkylamino, (di-lower alkylcarbamoyl)lower alkylamino, carbamoyloxy, mono-lower alkylcarbamoyloxy, di-lower alkylcarbamoyloxy, lower alkylsulfonyl, lower alkylsulfonylamino, sulfamoyl, mono-lower alkylsulfamoyl, di-lower alkylsulfamoyl, sulfamoylamino, (mono-lower alkylsulfamoyl)amino, (di-lower alkylsulfamoyl)amino, (mono-lower alkylsufamoyl)lower alkylamino or (di-lower alkylsulfamoyl)lower alkylamino;

wherein Group β represents halogen, hydroxyl, amino, cyano, mono-lower alkylamino, di-lower alkylamino, optionally fluorine-substituted lower alkyl, optionally fluorine-substituted lower alkyloxy, lower alkyloxycarbonyl, (lower alkyloxycarbonyl)amino, (lower alkyloxycarbonyl)lower alkylamino, carboxyl, lower alkylcarbonyl, lower alkylcarbonyloxy, (lower alkylcarbonyl) amino, (lower alkylcarbonyl)lower alkylamino, di-lower alkylcarbamoyl, di-lower alkylcarbamoylamino, (di-lower alkylcarbamoyl)lower alkylamino, di-lower alkylcarbamoyloxy, lower alkylsulfonyl, lower alkylsufonylamino, di-lower alkylsulfamoyl, sulfamoylamino, (di-lower alkylsulfamoyl)amino, (di-lower alkylsulfamoyl)lower alkylamino, or 5-6 membered aliphatic carbocycle or heterocycle which is optionally substituted with a group selected from group γ; and wherein Group γ represents lower alkylsulfonyl or lower alkyloxycarbonyl;
or a pharmaceutically acceptable salt thereof.

12. The compound of claim 11, wherein $R^1$ is methyl.

13. The compound of claim 12, wherein $R^2$ is selected from the group consisting of isopropyl, cyclopropyl, cyclobutyl, cyclopentyl, cyclohexyl, N-methylpyrrolidin-3-yl, N-acetylpyrrolidin-3-yl, N-methylpiperidin-4-yl, tetrahydrofuran-2-yl, 1-methanesulfonyl-pyrrolidin-3-yl and 1-(isopropylcarbonyl)pyrrolidin-3-yl.

14. The compound of claim 11, wherein all of $B^1$, $B^2$, and $B^3$ are hydrogen atoms.

15. The compound of claim 11, wherein $R^3$ is hydrogen or methyl.

16. The compound of claim 11, wherein $R^4$ is hydrogen or methyl.

17. The compound of claim 11, wherein $W^1$ is a mono- or bi-cyclic, 3-8 membered aromatic nitrogen-containing heterocycle wherein if the heterocycle is a pyrazole ring, the pyrazole ring may be substituted by methyl.

18. The compound of claim 17, wherein $W^1$ is selected from the group consisting of the following substitutents:

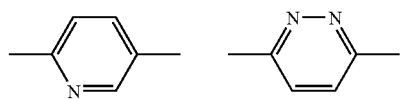

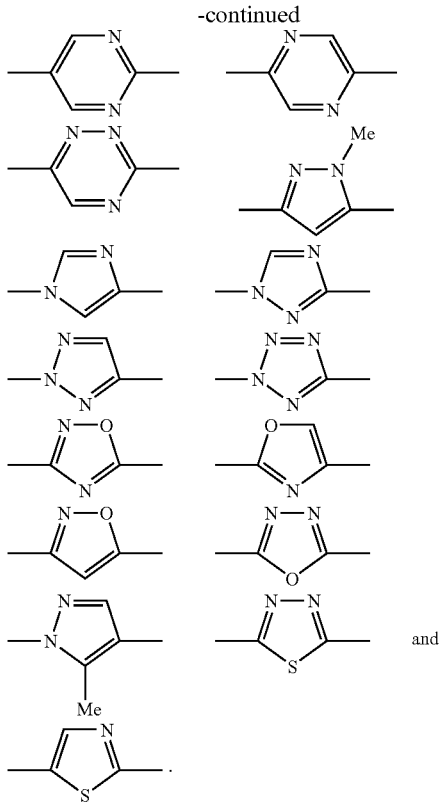

19. The compound of claim 17, wherein $W^1$ is selected from the group consisting of the following substituents:

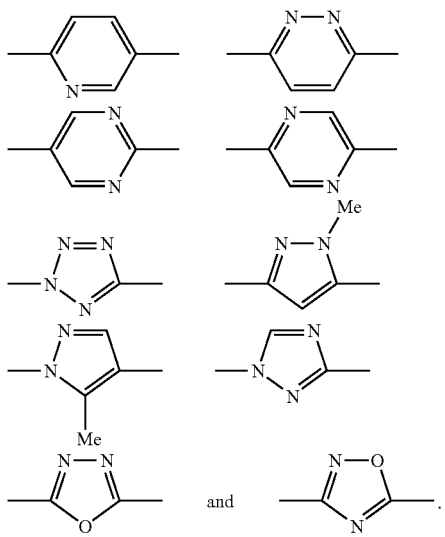

20. The compound of claim 11, wherein Ar is selected from the group consisting of phenyl, 2-fluorophenyl, 3-fluorophenyl, 4-fluorophenyl, 2-trifluoromethylphenyl, 3-trifluoromethylphenyl, 4-trifluoromethylphenyl, 4-methoxyphenyl, 4-methanesulphonylphenyl, 3-fluoro-4-methoxyphenyl, 3,4-difluorophenyl, 2,4-difluorophenyl, 4-chlorophenyl, 4-(piperidin-1-yl)phenyl and 4-(morpholin-1-yl)phenyl.

21. The compound of claim 11, wherein said compound is
  5-(4-fluorophenyl)-N-{2-[isopropyl(methyl)amino]-1H-benzimidazol-6-yl}-2-pyridinecarboxamide,
  5-(4-fluorophenyl)-N-{2-[isopropyl(methyl)amino]-1H-benzimidazol-6-yl}-2-pyrazinecarboxamide,
  N-{2-[isopropyl(methyl)amino]-1H-benzimidazol-6-yl}-N-methyl-5-[4-(trifluoromethyl)phenyl]-1,2,4-oxadiazole-3-carboxamide,
  3-(4-fluorophenyl)-N-{2-[isopropyl(methyl)amino]-1H-benzimidazol-6-yl}-1,2,4-oxadiazole-5-carboxamide,
  6-(4-fluorophenyl)-N-{2-[isopropyl(methyl)amino]-1H-benzimidazol-6-yl}-3-pyridinecarboxamide,
  N-{2-[1-acetyl-3-pyrrolidinyl(methyl)amino]-1-benzimidazol-6-yl}-5-(4-fluorophenyl)-2-pyridinecarboxamide,
  N-{2-[isopropyl(methyl)amino]-1H-benzimidazol-6-yl}-5-phenyl-2-pyrazinecarboxamide,
  N-{2-[1-acetyl-3-pyrrolidinyl(methyl)amino]-1H-benzimidazol-6-yl}-5-(4-fluorophenyl)-2-pyrazinecarboxamide,
  5-(4-fluorophenyl)-N-{2-[isopropyl(methyl)amino]-1H-benzimidazol-6-yl}-2-pyrimidinecarboxamide,
  6-(4-fluorophenyl)-N-{2-[isopropyl(methyl)amino]-1H-benzimidazol-6-yl}-3-pyridazinecarboxamide,
  2-(4-fluorophenyl)-N-{2-[isopropyl(methyl)amino]-1H-benzimidazol-6-yl}-5-pyrimidinecarboxamide,
  N-{2-[isopropyl(methyl)amino]-1H-benzimidazol-6-yl}-3-[4-(trifluoromethyl)phenyl]-1,2,4-oxadiazole-5-carboxamide,
  N-{2-[isopropyl[(methyl)amino]-1H-benzimidazol-6-yl}-1-[4-(trifluoromethyl)phenyl]-1,2,4-triazole-3-carboxamide,
  N-{2-[isopropyl(methyl)amino]-1H-benzimidazol-6-yl}-5-[4-(trifluoromethyl)phenyl]-1,3,4-oxadiazole-2-carboxamide,
  N-{2-[isopropyl(methyl)amino]-1H-benzimidazol-6-yl}-5-methyl-1-[4-(trifluoromethyl)phenyl]-1H-pyrazole-4-carboxamide,
  N-{2-[isopropyl(methyl)amino]-1H-benzimidazol-6-yl}-2-[4-(trifluoromethyl)phenyl]-2H-tetrazole-2-carboxamide,
  6-(3-fluorophenyl)-N-{2-[isopropyl(methyl)amino]-1H-benzimidazol-6-yl}-3-pyridinecarboxamide,
  N-{2-[isopropyl(methyl)amino]-1H-benzimidazol-6-yl}-5-phenyl-5-pyrimidinecarboxamide,
  5-(4-fluorophenyl)-N-{2-[isopropyl(methyl)amino]-1-methyl-1H-benzimidazol-6-yl}-2-pyrimidinecarboxamide, or
  N-{2-[isopropyl(methyl)amino]-1H-benzimidazol-6-yl}-5-phenyl-3-pyridinecarboxamide.

22. A pharmaceutical composition comprising the compound as described in claim 11 and a pharmaceutically acceptable carrier.

* * * * *